United States Patent [19]
Han et al.

[11] Patent Number: 6,034,089
[45] Date of Patent: Mar. 7, 2000

[54] ARYL THIOPHENE DERIVATIVES AS PDE IV INHIBITORS

[75] Inventors: Yongxin Han, Kirkland; Andre Giroux, Ste-Anne-De-Bellevue; Dwight MacDonald, L'Ile Bizard; Robert N. Young, Senneville; Helene Perrier, Ville Ile Perrot; Carole Lepine, La Val, all of Canada

[73] Assignee: Merck & Co., Inc., Rahway, N.J.

[21] Appl. No.: 09/163,033

[22] Filed: Sep. 28, 1998

Related U.S. Application Data

[60] Provisional application No. 60/060,914, Oct. 3, 1997.
[51] Int. Cl.[7] .................. A61K 31/505; A61K 31/44; A61K 31/38; C07D 403/00; C07D 409/00
[52] U.S. Cl. .................. 514/269; 514/336; 514/438; 514/444; 544/296; 544/300; 546/280.4; 549/59; 549/78; 549/79
[58] Field of Search .................. 549/80, 78, 79, 549/59; 514/438, 444, 269, 336; 544/296, 300; 546/280.4

[56] References Cited

U.S. PATENT DOCUMENTS

| | | | |
|---|---|---|---|
| 3,222,290 | 12/1965 | Braus et al. | 549/57 |
| 5,474,995 | 12/1995 | Durcharme et al. | 514/241 |

FOREIGN PATENT DOCUMENTS

| | | |
|---|---|---|
| 91/19708 | 12/1991 | WIPO . |
| 94/15932 | 7/1994 | WIPO . |

OTHER PUBLICATIONS

Takeda et al, "Preparation of 2,5–diphenylpyrrole derivatives as anti–dermatitis drugs", CA126:89251, Feb. 14, 1997.
Porizet et al, "Thiophene S–Oxides . . . ", J. Chem. Soc. Chem. Commun., 1995.
Gotthardt, H. et al. Chem. Ber. 111: 2028–2036 (1978).
Burger, K. et al. Heterocycles 39(2): 819–832 (1994).
Minato, A. et al. Tet. Let. 21: 4017–4020 (1980).
Freeman, F. et al. J. Org. Chem. 59: 4350–4354 (1994).
Bottcher, V. B. et al. Justis Liebigs Annalen Der Chemie 557: 89–107 (1947).

*Primary Examiner*—Deborah C. Lambkin
*Attorney, Agent, or Firm*—Shu Muk Lee; David L. Rose

[57] ABSTRACT

The invention encompasses the novel compound of Formula I useful in the treatment of diseases, including asthma, by raising the level of cyclic adenosine-3',5'-monophosphate (cAMP) through the inhibition of phosphodiesterase IV (PDE IV).

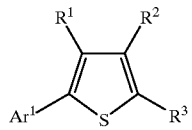

The invention also encompasses certain pharmaceutical compositions and methods for treatment of diseases by inhibition of PDE IV, resulting in an elevation of cAMP, comprising the use of compounds of Formula I.

11 Claims, No Drawings

ARYL THIOPHENE DERIVATIVES AS PDE IV INHIBITORS

CROSS REFERENCE TO RELATED APPLICATIONS

This application is a non-provisional application related to U.S. Application Serial No. 60/060,914, filed on Oct. 3, 1997 priority of which is claimed hereunder.

BACKGROUND OF THE INVENTION

This invention relates to compounds and pharmaceutical compositions for the treatment of diseases by raising the level of cyclic adenosine-3',5'-monophosphate (cAMP) through the inhibition of phosphodiesterase IV (PDE IV).

Many hormones and neurotransmitters modulate tissue function by elevating intra-cellular levels of 3',5'-cyclic adenosine monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I-VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) *J. Immunol.* 148 2503–2510) and eosinophils (Dent G. et al., (1991) *Br. J. Pharmacol.* 103 1339–1346) and that inhibition of this isotype is associated with the inhibition of cell activation. Furthermore, elevation of cAMP in airway smooth muscle has a spasmolytic effect. Consequently PDE IV inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. For PDE IV, it is has been shown that there are four isoforms (A, B, C and D) each coded for by a separate gene in both rodents (Swinnen J. V. et al., (1989) *Proc. Natl. Acad. Sci. USA* 86 5325–5329) and man (Bolger G. et al., (1993) *Mol. Cell Biol.* 13 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al., 1989; Bolger et al., 1993; Obernolte R. et al., (1993) *Gene* 129 239–247, ibid) and the high degree of sequence conservation amongst isoforms of different species.

To date full length cDNAs for human PDE IVA, B and D (Bolger et al., 1993 ibid; Obernolte et al., 1993 ibid; Mclaughlin M. et al., (1993) *J. Biol. Chem.* 268 6470–6476) and rat PDE IVA, B and D (Davis R. et al., (1989) *Proc. Natl. Acad. Sci. USA* 86 3604–3608; Swinnen J. V. et al., (1991) *J. Biol. Chem.* 266 18370–18377), have been reported, enabling functional recombinant enzymes to be produced by expression of the cDNAs in an appropriate host cell. These cDNAs have been isolated by conventional hybridisation methods. However using this approach, only partial cDNAs for both human and rat PDE IVC have been obtained. (Bolger et al., ibid. 1993 and Swinnen et al., ibid. 1989 and International Patent Specification No. WO 91/16457.)

The design of PDE IV inhibitors for the treatment of inflammatory diseases such as asthma, has met with limited success to date. Many of the PDE IV inhibitors which have been synthesised have lacked potency and/or inhibit more than one type of PDE isoenzyme in a non-selective manner. PDE IV inhibitors that are relatively potent and selective for PDE IV, are reported to be emetic as well. Indeed this side effect has been so universal that experts have expressed their belief that the emesis experienced upon administration of a PDE IV inhibitor, may be mechanism based.

We have now found a novel series of aryl thiophene derivatives, members of which compared to known structurally similar compounds are potent inhibitors of PDE IV at concentrations at which they have little or no inhibitory action on other PDE isoenzymes. These compounds inhibit the human recombinant PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyper-responsiveness of airway smooth muscle seen in inflamed lungs. Advantageously, compounds according to the invention have good oral activity and at orally effective doses exhibit little or none of the side-effects associated with known PDE IV inhibitors, such as rolipram. The compounds of the invention are therefore of use in medicine, especially in the prophylaxis and treatment of asthma and other inflammatory conditions.

SUMMARY OF THE INVENTION

The invention encompasses novel compounds of Formula I useful in the treatment of disease by inhibition of PDE IV, resulting in an elevation of cAMP.

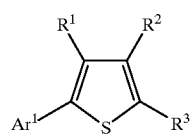

The invention also encompasses certain pharmaceutical compositions and methods for treatment of diseases by inhibition of PDE IV, resulting in an elevation of cAMP, comprising the use of compounds of Formula I.

DETAILED DESCRIPTION OF THE INVENTION

The invention encompasses the novel compound of Formula I useful in the treatment of disease by inhibition of PDE IV, resulting in an elevation of cAMP,

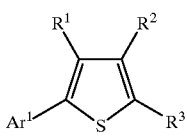

or a pharmaceutically acceptable salt thereof wherein:
$Ar^1$ is an aromatic ring selected from phenyl, quinolinyl, pyridinyl, furyl, thienyl or thiazolyl, optionally substituted with up to two substituents chosen independently from among:
 a) $C_{1-6}$alkyl, optionally substituted with —OH, —$CO_2H$, $CO_2C_{1-3}$alkyl, and CN,
 b) $C_{1-3}$alkoxy,
 c) $C_{1-3}$alkylthio,
 d) $C_{1-3}$alkylsulfinyl,
 e) $C_{1-3}$alkylsulfonyl,
 f) $C_{1-3}$fluoroalkyl, optionally substituted with —OH,
 g) halo,
 h) —OH,
 i) —$CO_2H$,
 j) —$CO_2C_{1-3}$alkyl,
 k) —CH=CH—C(Me)$_2$OH,
 l) —CONR$^4$R$^5$,
 m) —S(O)$_2$NR$^6$R$^7$,
 n) tetrazol-5-yl, or
 o) —CH=N—O—CH$_2$CO$_2$H;

$R^1$ is selected from:
 a) hydrogen,
 b) $C_{1-3}$alkyl, optionally substituted with —OH, or
 c) —X$^1$—Y$^1$—Ar$^2$,
  wherein:
  X$^1$ is
   1) —CH$_2$—, or
   2) a bond;
  Y$^1$ is
   1) —O—
   2) —S—,
   3) —NR$^8$—, or
   4) a bond;
  Ar$^2$ is an aromatic ring selected from phenyl, naphthyl, pyrimidinyl, pyridinyl or thienyl, optionally substituted with up to two substituents chosen independently among:
   1) $C_{1-6}$alkyl,
   2) $C_{1-6}$alkoxy,
   3) —OH,
   4) halo, or
   5) CF$_3$;

$R^2$ is selected from:
 a) hydrogen or
 b) $C_{1-3}$alkyl.

$R^3$ is selected from phenyl, naphthyl, pyridinyl, furyl, thienyl, or ethinyl, optionally substituted with up to two substituents chosen independently among:
 a) $C_{1-3}$alkyl,
 b) $C_{1-3}$fluoroalkyl,
 c) $C_{1-6}$alkoxy,
 d) $C_{1-3}$fluoroalkoxy,
 e) $C_{1-3}$alkylthio,
 f) halo,
 g) —OH,
 h) —NO$_2$,
 i) —CH$_2$OH,
 j) —NHCONR$^9$R$^{10}$,
 k) —S(O)$_2$NR$^{11}$R$^{12}$,
 l) —SCH$_2$(1,1-c-Pr)CH$_2$CO$_2$H,
 m) 1-piperazinyl, optionally substituted with $C_{1-3}$alkyl,
 n) 4-morpholinyl, or
 o) —X$^2$—Y$^2$—Ar$^3$,
  wherein,
  X$^2$ is
   1) —CH$_2$—,
   2) —C(=NOH)—, or
   3) a bond;
  Y$^2$ is
   1) —O—,
   2) —S—, or
   3) a bond;
  Ar$^3$ is phenyl, pyridinyl, pyrimidinyl or pyrazinyl, optionally substituted with up to two substituents chosen independently among:
   1) $C_{1-3}$alkyl, optionally substituted with —OH, or
   2) —CH$_2$CO$_2$H.

$R^4$ and $R^5$ are independently selected from:
 a) hydrogen,
 b) $C_{1-3}$alkyl,
 c) —S(O)$_2$C$_{1-3}$alkyl, or
 d) —S(O)$_2$phenyl, optionally mono-substituted with $C_{1-3}$alkyl, $C_{1-3}$alkoxy, $C_{1-3}$alkylthio or halo.

$R^6$ and $R^7$ are independently chosen from among:
 a) hydrogen,
 b) $C_{14}$alkyl,
 c) —CO—$C_{1-4}$alkyl, or
 d) —CO-phenyl, optionally mono-substituted with $C_{1-3}$alkyl, $C_{1-3}$alkoxy, $C_{1-3}$alkylthio or halo;

$R^8$ is chosen from among:
 a) hydrogen, or
 b) $C_{1-5}$alkyl;

$R^9$ and $R^{10}$ are independently chosen from among:
 a) hydrogen,
 b) $C_{1-4}$alkyl, or
 c) phenyl; and $R^{11}$ and $R^{12}$ are independently chosen from among:
 a) hydrogen or
 b) $C_{1-5}$alkyl.

Within this embodiment there is a preferred genus of compounds wherein
$R^1$ is selected from:
 a) $C_{1-3}$alkyl, optionally substituted with —OH, or
 b) —X$^1$—Y$^1$—Ar$^2$;
$R^2$ is hydrogen;
and the remaining substituents are defined as in Formula I above.

Another preferred genus is that in which —X$^1$—Y$^1$— is —CH$_2$—S— and the remaining substituents are defined as in Formula I above.

Another preferred genus is that in which Ar$^2$ is pyrimidinyl, optionally substituted with up to two substituents chosen independently among:
 1) $C_{1-6}$alkyl,
 2) $C_{1-6}$alkoxy,
 3) —OH, or
 4) halo.

Still another preferred genus is realized when:
$Ar^1$ is an aromatic ring selected from phenyl, quinolinyl, pyridinyl, furyl, thienyl or thiazolyl, optionally substituted with up to two substituents chosen independently from among:

a) $C_{1-6}$alkyl, optionally substituted with —OH, —CO$_2$H, CO$_2$C$_{1-3}$alkyl, and CN,
b) $C_{1-3}$alkoxy,
c) $C_{1-3}$alkylthio,
d) $C_{1-3}$alkylsulfinyl,
e) $C_{1-3}$alkylsulfonyl,
f) $C_{1-3}$fluoroalkyl, optionally substituted with —OH,
g) halo,
h) —OH,
i) —CO$_2$H,
j) —CO$_2$C$_{1-3}$alkyl, $R^1$ is selected from:
b) $C_{1-3}$alkyl, optionally substituted with —OH, or
c) —X$^1$—Y$^1$—Ar$^2$,
  wherein:
  $X^1$ is
    1) —CH$_2$—, or
    2) a bond;
  $Y^1$ is
    —O—
    2) —S—,
    3) —NR$^8$—, or
    4) a bond;
  Ar$^2$ is pyrimidinyl optionally substituted with up to two substituents chosen independently among:
    1) $C_{1-6}$alkyl,
    2) $C_{1-6}$alkoxy,
    3) —OH, or
    4) halo, $R^2$ is selected from:
a) hydrogen or $R^3$ is selected from phenyl, naphthyl, pyridinyl, furyl, or thienyl, optionally substituted with up to two substituents chosen independently among:
a) $C_{1-3}$alkyl,
b) $C_{1-3}$fluoroalkyl,
c) $C_{1-6}$alkoxy,
d) $C_{1-3}$fluoroalkoxy,
e) $C_{1-3}$alkylthio,
f) halo,
g) —OH,
h) —NO$_2$,
i) —CH$_2$OH,
j) —NHCONR$^9$R$^{10}$,
k) —S(O)$_2$NR$^{11}$R$^{12}$,
l) —SCH$_2$(1,1-c-Pr)CH$_2$CO$_2$H or
m) —X$^2$—Y$^2$—Ar$^3$,
  wherein,
  $X^2$ is
    1) —CH$_2$—,
    2) —C(=NOH)—, or
    3) a bond;
  $Y^2$ is
    1) —O—,
    2) —S—, or
    3) a bond;
  Ar$^3$ is phenyl, pyridinyl, or pyrimidinyl optionally substituted with up to two substituents chosen independently among:
    1) $C_{1-3}$alkyl, optionally substituted with —OH, or
    2) —CH$_2$CO$_2$H.

$R^4$ and $R^5$ are independently selected from:
a) hydrogen,
b) $C_{1-3}$alkyl,
c) —S(O)$_2$C$_{1-3}$alkyl, or $R^6$ and $R^7$ are independently chosen from among:
a) hydrogen,
b) $C_{1-4}$alkyl,
c) —CO—C$_{1-4}$alkyl, or $R^8$ is chosen from among:
a) hydrogen, or
b) $C_{1-5}$alkyl;

$R^9$ and $R^{10}$ are independently chosen from among:
a) hydrogen,
b) $C_{1-4}$alkyl, and $R^{11}$ and $R^{12}$ are independently chosen from among:
a) hydrogen or
b) $C_{1-5}$alkyl.

Yet another preferred genus is realized when:

Ar$^1$ is an aromatic ring selected from phenyl, quinolinyl, pyridinyl, furyl, thienyl or thiazolyl, optionally substituted with up to two substituents chosen independently from among:
a) $C_{1-6}$alkyl, optionally substituted with —OH, —CO$_2$H, CO$_2$C$_{1-3}$alkyl, and CN,
b) $C_{1-3}$alkoxy,
c) $C_{1-3}$alkylthio,
d) $C_{1-3}$alkylsulfinyl,
e) $C_{1-3}$alkylsulfonyl,
f) $C_{1-3}$fluoroalkyl, optionally substituted with —OH,
g) halo,
h) —OH,
i) —CO$_2$H,
j) —CO$_2$C$_{1-3}$alkyl, $R^1$ is selected from:
b) $C_{1-3}$alkyl, optionally substituted with —OH, or
c) —X$^1$—Y$^1$—Ar$^2$,
  wherein:
  $X^1$—Y$^1$ is CH$_2$S;
  Ar$^2$ is pyrimidinyl optionally substituted with up to two substituents chosen independently among:
    1) $C_{1-6}$alkyl,
    2) $C_{1-6}$alkoxy,
    3) —OH, or
    4) halo, $R^2$ is hydrogen;

$R^3$ is selected from phenyl, pyridinyl, furyl, or thienyl, optionally substituted with up to two substituents chosen independently among:
a) $C_{1-3}$alkyl,
b) $C_{1-3}$fluoroalkyl,
c) $C_{1-3}$alkoxy,
d) $C_{1-3}$fluoroalkoxy,
e) $C_{1-3}$alkylthio,
f) halo,
g) —OH,
h) —NO$_2$,
i) —CH$_2$OH,
j) —NHCONR$^9$R$^{10}$,
k) —X$^2$—Y$^2$—Ar$^3$,
  wherein,
  $X^2$ is
    1) —CH$_2$—, or
    2) a bond;
  $Y^2$ is
    1) —O—,
    2) —S—, or
    3) a bond;
  Ar$^3$ is phenyl, pyridinyl, or pyrimidinyl optionally substituted with up to two substituents chosen independently among:

1) $C_{1-3}$alkyl, optionally substituted with —OH, or
2) —$CH_2CO_2H$.

$R^4$ and $R^5$ are independently selected from:
 a) hydrogen,
 b) $C_{1-3}$alkyl, $R^6$ and $R^7$ are independently chosen from among:
 a) hydrogen,
 b) $C_{1-4}$alkyl, $R^8$, $R^{11}$ and $R^{12}$ are chosen from among:
 a) hydrogen, or
 b) $C_{1-5}$alkyl; and $R^9$ and $R^{10}$ are independently chosen from among:
 a) hydrogen,
 b) $C_{1-4}$alkyl.

As appreciated by those of skill in the art, halo is intended to include F, Cl, Br, and I.

For purposes of this specification alkyl is defined to include straight, branched, and cyclic structures of the indicated number of carbon atoms. By way of example, $C_{1-6}$alkyl includes methyl, ethyl, propyl, i-propyl, s- and t-butyl, pentyl, hexyl, 1,1-dimethylethyl, cyclopropyl, cyclobutyl, cyclopentyl and cyclohexyl. Similarly, alkoxy, alkylthio, alkylsulfinyl, and alkylsulfonyl mean the corresponding groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like. Examples of alkylthio groups include methylthio, propylthio, isopropylthio, cycloheptylthio, etc. By way of illustration, the propylthio group signifies —$SCH_2CH_2CH_3$. Fluoroalkyl means an alkyl group of the indicated number of carbon atoms, of straight, branched or cyclic structure, in which one or more hydrogen atoms have been replaced by fluorine atoms; fluoroalkoxy, fluoroalkylthio, fluoroalkylsulfinyl, and fluoroalkylsulfonyl have the analogous meanings.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for treatment of disease by inhibition of PDE IV, as disclosed herein comprising a pharmaceutically acceptable carrier and a non-toxic therapeutically effective amount of compound of Formula I as described above.

Within this embodiment the invention encompasses pharmaceutical compositions for treatment of disease by inhibition of PDE IV, resulting in an elevation of cAMP, as disclosed herein comprising a pharmaceutically acceptable carrier and a non-toxic therapeutically effective amount of compound of Formula I as described above.

For purposes of this specification a compound is said to selectively inhibit PDE IV in preference to other PDE's if the ratio of the IC50 concentration for all other PDE inhibition to PDE IV inhibition is 100 or greater.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N_-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes Alzheimer's disease, allergic rhinitis, allergic conjunctivitis, vernal conjunctivitis, arterial restenosis and artherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, multiple sclerosis, ankylosing spondylitis, transplant rejection and graft versus host disease.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteo-arthritis.

Over-production of cytokines such as TNF in bacterial, fungal or viral infections or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of Formula I together with one or more pharmaceutically acceptable carriers, excipients or diluents.

For the treatment of any of these, compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension.

This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Exemplifying the invention are:

EXAMPLE 1

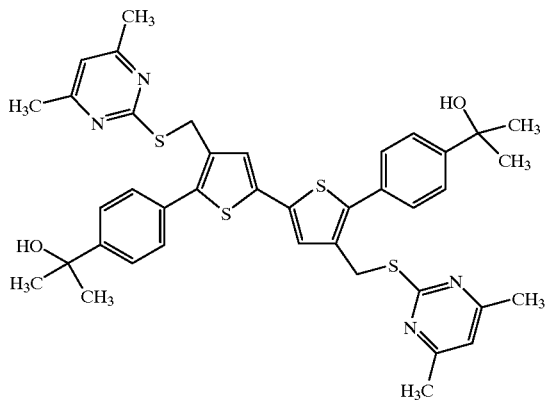

Proton NMR (acetone-d6): 7.66 (d, 4H), 7.55 (d, 4H), 7.41 (s, 2H), 6.90 (s, 2H), 4.46 (s, 4H), 4.39 (s, 2H), 2.35 (s, 12H),1.56 (s, 12H).

EXAMPLE 2

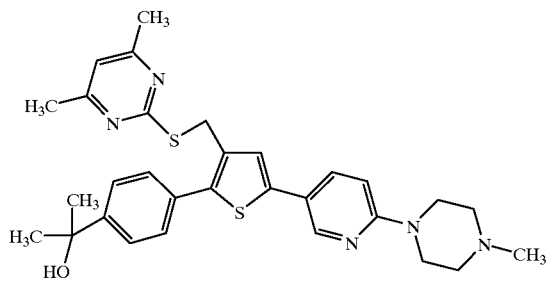

'Proton NMR (acetone-d6): 8.42 (d, 1H), 7.75 (dd, 1H), 7.64 (d, 2H), 7.54 (d, 2H), 7.41 (s, 1H), 6.88 (s, 1H), 6.80 (d, 1H), 4.46 (s, 2H), 2.24 (s, 3H), 1.55 (s, 3H).

EXAMPLE 3

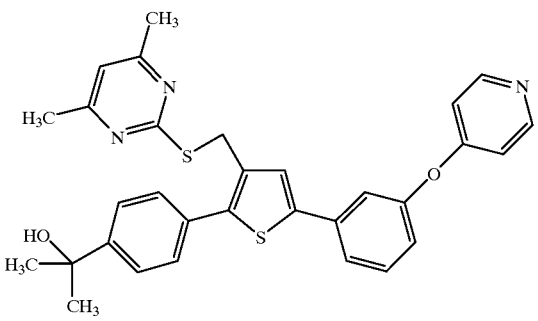

'Proton NMR (acetone-d6): 8.47(dd, 2H), 7.67–7.64 (m, 4H), 7.59–7.52 (m, 5H), 7.45 (t, 1H), 7.10 (dd, 1H), 6.95 (dd, 2H), 6.87 (s, 1H), 4.47 (s, 2H), 4.14 (s, 1H), 2.30 (s, 6H), 1.55 (s, 6H).

EXAMPLE 4

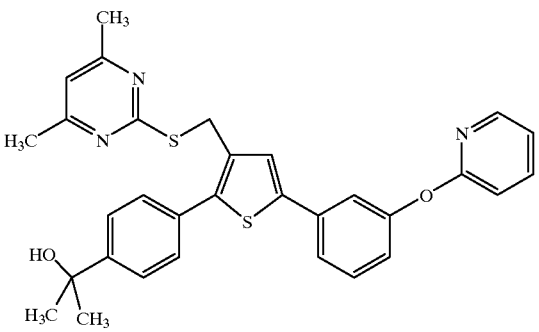

'Proton NMR (acetone-d6): 8.47(dd, 2H), 7.67–7.64 (m, 4H), 7.59–7.52 (m, 5H), 7.45 (t, 1H), 7.10 (dd, 1H), 6.95 (dd, 2H), 6.87 (s, 1H), 4.47 (s, 2H), 4.14 (s, 1H), 2.30 (s, 6H), 1.55 (s, 6H).

EXAMPLE 5

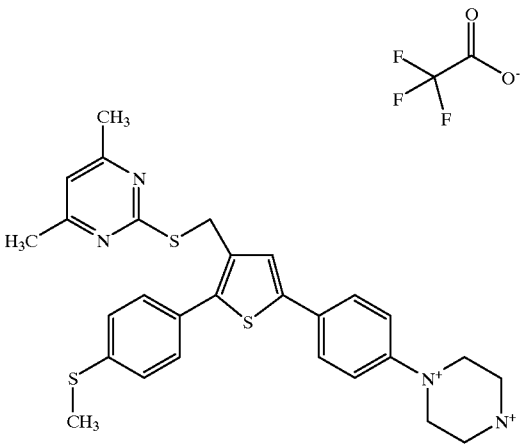

'Proton NMR (CDCl3): 9.85 (bs, 2H), 7.50–7.47 (m, 4H), 7.31 (s, 1H), 7.28 (d, 1H), 6.90 (d, 2H), 6.69 (s, 1H), 4.42 (s, 2H), 3.45 (bs, 4H), 3.34 (bs, 4H), 2.50 (s, 3H), 2.37 (s, 6H).

EXAMPLE 6
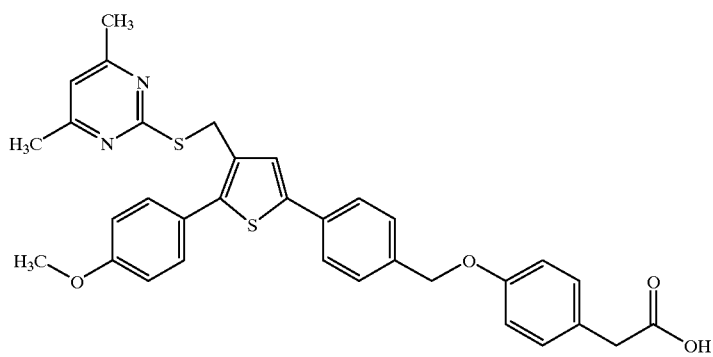
'Proton NMR (acetone-d6): 7.66 (d, 2H), 7.56–7.50 (m, 5H), 7.24 (d, 2H), 7.07 (d, 2H), 6.97 (d, 2H), 6.89 (s, 1H), 5.12 (s, 2H), 4.44 (s, 2H), 3.85 (s, 3H), 3.53 (s, 2H), 2.34 (s, 6H).
EXAMPLE 7
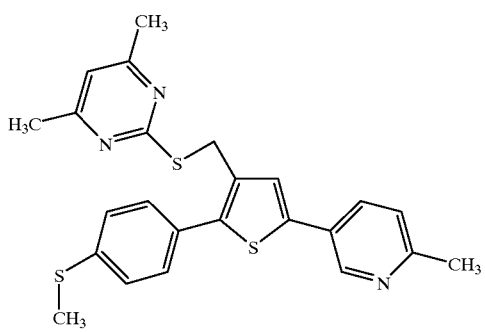
'Proton NMR (acetone-d6): 8.72 (d, 1H), 7.84 (dd, 1H), 7.59 (s, 1H), 7.55 (d, 2H), 7.37 (d, 2H), 7.24 (d, 1H), 6.87 (s, 1H), 4.45 (s, 2H), 2.52 (s, 3H), 2.48 (s, 3H), 2.32 (s, 6H).
EXAMPLE 8
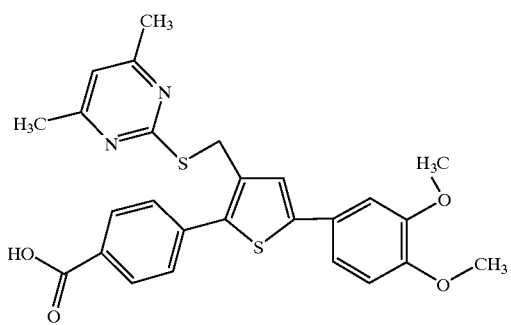
'M.P.: 238.8° C. (decomposed).
EXAMPLE 9
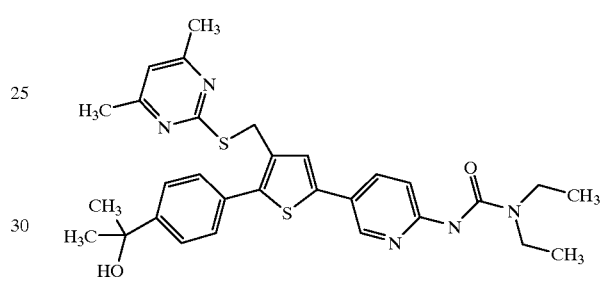
'Proton NMR (acetone-d6): 8.48 (d, 1H), 8.12 (d, 1H), 7.90 (dd, 1H), 7.89 (s, 1H), 7.66 (d, 2H), 7.55 (d, 2H), 7.54 (s, 1H), 6.88 (s, 1H), 4.47 (s, 2H), 4.18 (s, 1H), 3.49 (q, 4H), 2.32 (s, 6H), 1.55 (s, 1H), 3.49 (q, 4H), 2.32 (s, 6H), 1.55 (s, 6H).
EXAMPLE 10
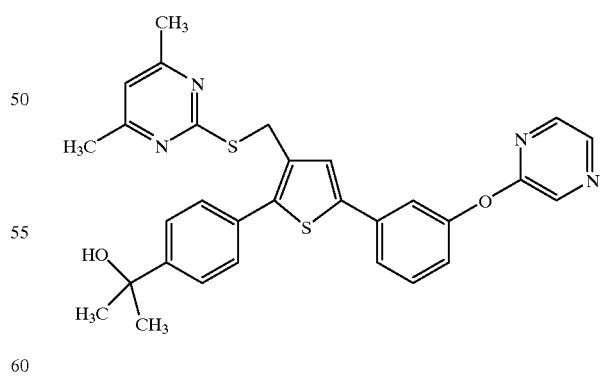
'Proton NMR (acetone-d6): 8.48 (d, 1H), 8.33 (d, 1H), 8.41 (d, 1H), 7.65 (m, 3H), 7.57–7.47 (m, 5H), 7.15 (dd, 1H), 6.87 (s, 1H), 4.47 (s, 1H), 4.11 (s, 1H), 2.31 (s, 6H), 1.55 (s, 6H).

EXAMPLE 11
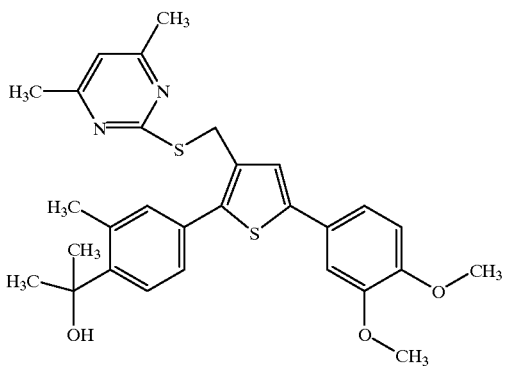
Proton NMR (acetone-d6):7.58 (d, 1H), 7.47 (s, 1H), 7.37 (dd, 1HO, 7.35 (s, 1H),7.22 (d, 2H), 7.18 (dd, 1H), 6.97 (d, 1H), 6.89 (s, 1H)4.46 (s, 2H), 4.09 (s, 1H, OH), 3.88 (s, 3H), 3.83 (s, 3H), 2.61 (s, 3H), 2.34 (s, 6H), 1.623 (s, 6H).
EXAMPLE 12
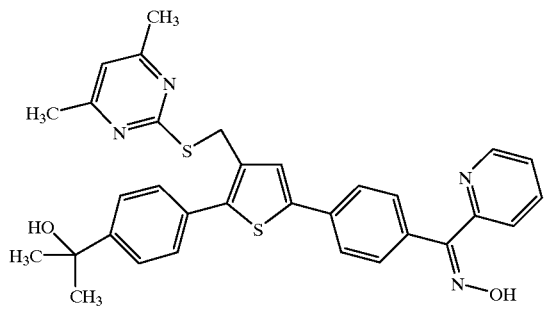
Proton NMR (acetone-d6):11.21 (s, 1H), 8.61 (dd, 1H), 8.68 (dd, 1H), 8.64 (dd, 1H), 7.94 (m, 1H), 7.71–7.56 (m, 6H), 7.49 (d, 2H), 7.46 (m, 1H), 6.89 (s, 1H), 4.48 (s, 2H), 4.17 (s, 1H), 2.33 (s, 6H), 1.58 (s, 6H).
EXAMPLE 13
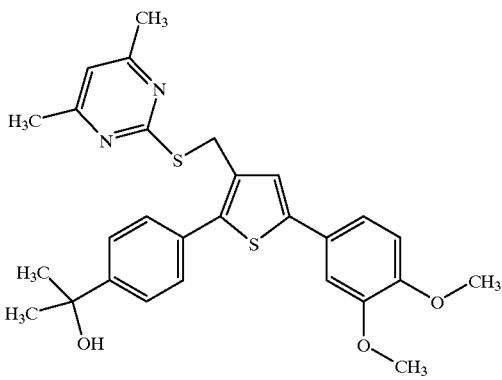
m.p.: 71.5° C.
EXAMPLE 14
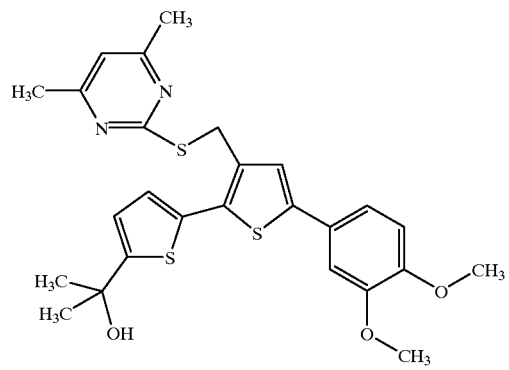
Proton NMR (acetone-d6)7.47 (s, 1H), 7.20 (d, 1H), 7.15 (dd, 1H), 7.13 (d, 1H),6.98–6.96 (m, 2H), 6.90 (s, 1H), 4.54 (s, 2H), 3.88 (s, 3H),3.82 (s, 3H), 2.36 (s, 6H), 1.62 (s, 6H).
EXAMPLE 15
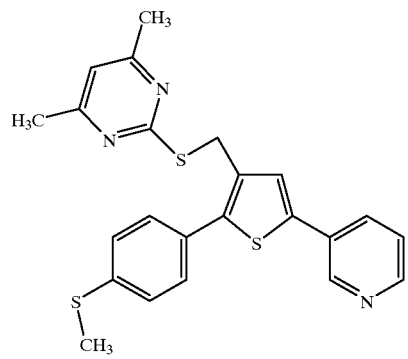
'Proton NMR (acetone-d6): 8.88 (dd, 1H), 8.50 (dd, 1H), 8.02 (ddd, 1H), 7.68 (s, 1H), 7.58 (d, 2H), 7.41 (m, 1H), 7.40 (d, 2H), 6.90 (s, 1H), 4.48 (s, 2H), 2.55 (s, 3H), 2.34 (s, 6H).
EXAMPLE 16
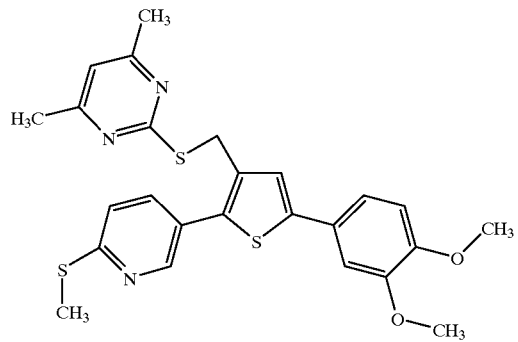
Proton NMR (acetone-d6):8.68 (dd, 1H), 7.82 (dd, 1H), 7.50 (s, 1H), 7.36 (d, 1H), 7.23 (d, 1H), 7.18 (dd, 1H), 6.98 (m, 1H), 6.89 (s, 1H), 4.45 (s, 2H), 3.89 (s, 3H), 3.83 (s, 3H), 2.58 (s, 3H), 2.34 (s, 6H).

EXAMPLE 17
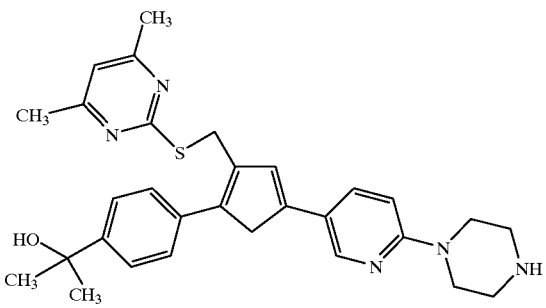
Proton NMR (acetone-d6:8.42 (dd, 1H), 7.75 (dd, 1H), 7.65 (d, 2H), 7.54 (d, 2H), 7.42 (d, 1H), 6.89 (s, 1H), 6.80 (d, 1H), 4.46 (s, 2H),3.59 (t, 4H), 2.93 (t, 4H), 2.33 (s, 6H), 1.54 (s, 6H).
EXAMPLE 18
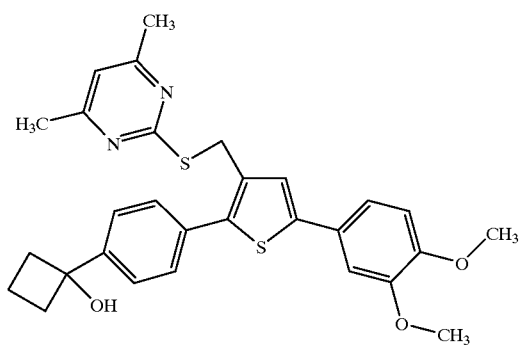
Proton NMR (CDCl3):7.61 (dd, 2H), 7.57 (dd, 2H), 7.35 (s, 1H), 7.16 (dd, 1H), 7.08 (d, 1H), 6.86 (d, 1H), 6.69 (s, 1H), 4.47 (s, 2H), 3.93 (s, 3H), 3.90 (s, 3H), 2.63–2.56 (m, 2H), 2.44–2.36 (m, 2H), 2.38 (s, 6H), 2.08 (s, 1H), 2.07–2.04 (m, 1H), 1.76–1.73 (m, 1H).
EXAMPLE 19
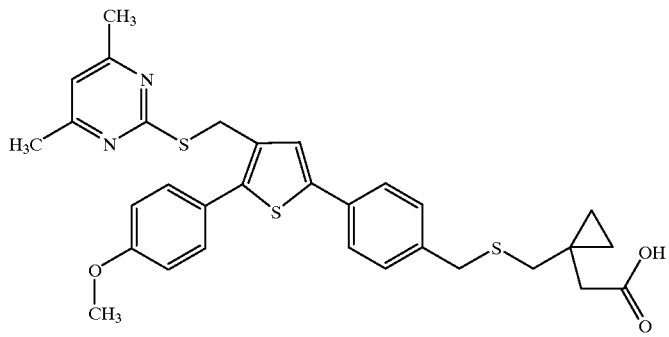
Proton NMR (acetone-d6):7.57 (d, 2H), 7.55 (d, 2H), 7.54 (s, 1H), 7.37 (d, 2H), 7.06 (d, 2H), 6.88 (s, 1H), 4.43 (s, 2H), 3.84 (s, 3H), 3.78 (s, 2H), 2.66 (s, 2H), 2.44 (s, 2H), 2.34 (s, 6H), 0.52 (dd, 2H), 0.45 (dd, 2H).
EXAMPLE 20
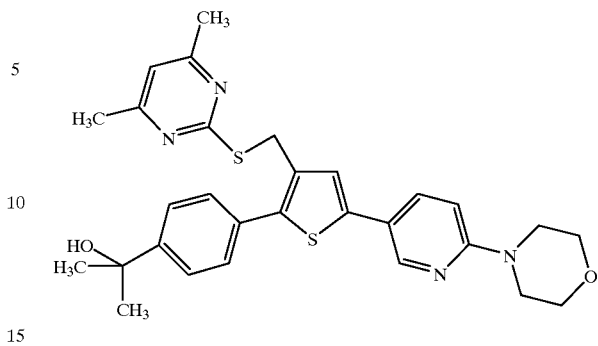
Proton NMR (acetone-d6):8.45 (d, 1H), 7.80 (dd, 1H), 7.65 (dd, 2H), 7.55 (dd, 2H), 7.44 (s, 1H), 6.90 (s, 1H), 6.84 (s, 1H), 4.47 (s, 2H), 3.74 (t, 4H), 3.53 (t, 4H), 2.34 (s, 6H), 1.55 (s, 6H).
EXAMPLE 21
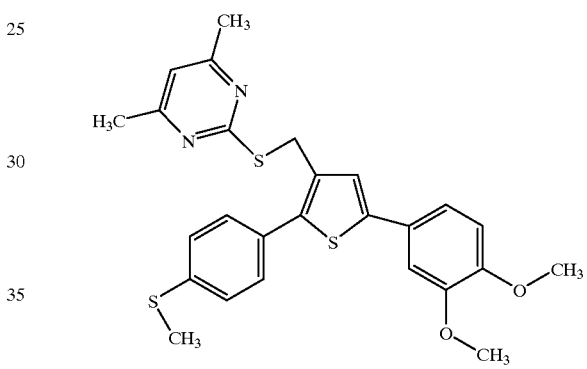
'Proton NMR (acetone-d6): 7.55 (d, 2H), 7.49 (s, 1H), 7.39 (d, 2H), 7.22 (d, 1H), 7.18 (dd, 1H), 6.98 (d, 1H), 6.89 (s, 1H), 4.45 (s, 2H), 3.88 (s, 3H), 3.83 (s, 3H), 2.53 (s, 3H), 2.34 (s, 6H).

EXAMPLE 22
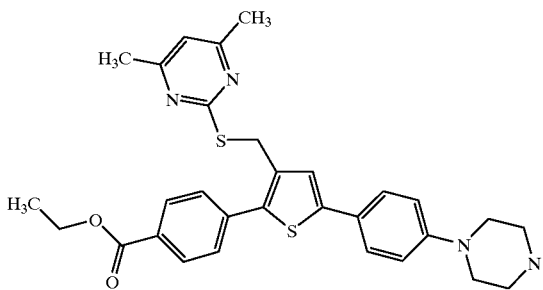
Proton NMR (acetone-d6):8.10 (d, 2H), 7.74 (d, 2H), 7.54 (d, 2H), 7.45 (s, 1H), 6.97 (d, 2H), 6.89 (s, 1H), 4.50 (s, 2H), 4.36 (q, 2H), 3.16 (dd, 4H), 2.93 (dd, 4H), 2.32 (s, 6H), 1.39 (t, 3H).
EXAMPLE 23
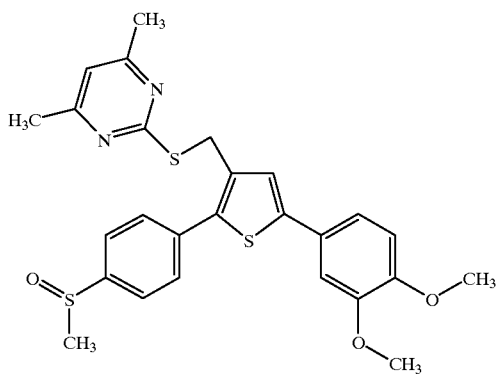
Proton NMR (acetone-d6):8.87 (dd, 1H), 8.28 (dd, 1H), 8.05 (dd, 1H), 7.56 (s, 1H), 7.25 (d, 1H), 7.19 (dd, 1H), 6.98 (d, 1H), 6.87 (s, 1H), 4.48 (s, 2H), 3.38 (s, 3H), 3.83 (s, 3H), 2.81 (s, 3H), 2.29 (s, 3H).
EXAMPLE 24
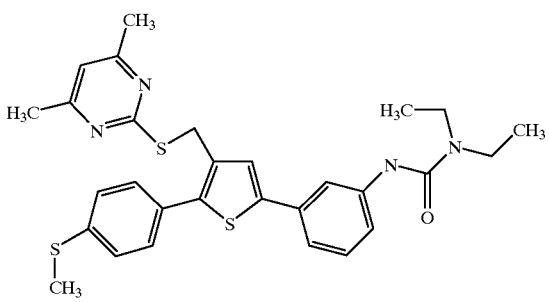
Proton NMR (CDCl3):7.71 (d, 2H), 7.48–7.46 (m, 2H), 7.44 (s, 1H), 7.43 (t, 1H), 7.30 (d, 2H), 7.12 (d, 1H), 6.74 (s, 1H), 4.47 (s, 1H), 3.33 (q, 4H), 2.50 (s, 3H), 2.43 (s, 6H), 1.02 (t, 6H).
EXAMPLE 25
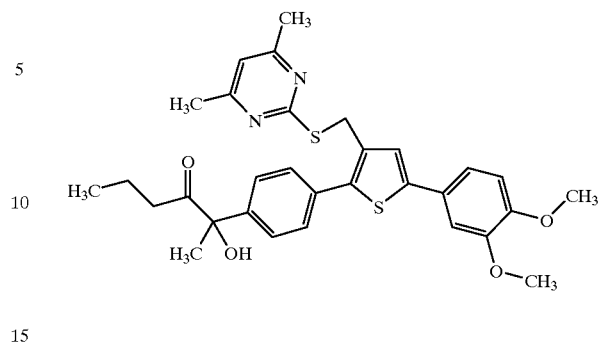
Proton NMR (CDCl3):7.63 (d, 2H), 7.58 (d, 2H), 7.34 (s, 1H), 7.16 (dd, 1H), 7.09 (dd, 1H), 6.85 (d, 1H), 6.69 (s, 1H), 4.45 (s, 2H), 4.31–4.21 (m, 2H), 3.93 (s, 3H), 3.90 (s, 3H), 3.81 (s, 1H), 2.37 (s, 6H), 1.80 (s, 3H), 1.28 (t, 3H).
EXAMPLE 26
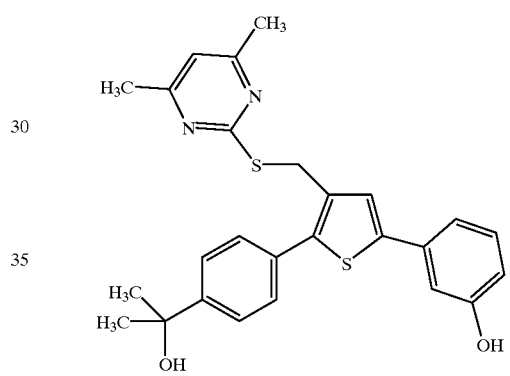
Proton NMR (acetone-d6):8.48 (s, 1H), 7.65 (d, 2H), 7.55 (d, 2H), 7.53 (s, 1H), 7.24 (t, 1H), 7.15–7.11 (m, 2H), 6.90 (s, 1H),6.80 (dd, 1H), 4.47 (s, 2H), 4.04 (s, 1H), 2.34 (s, 6H) 1.55 (s, 6H).
EXAMPLE 27
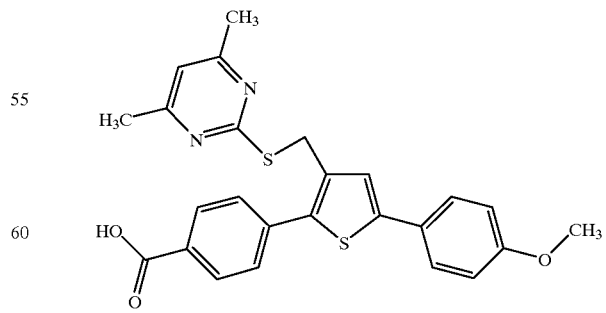
M.P.: 187.7° C. (decomposed).

EXAMPLE 28
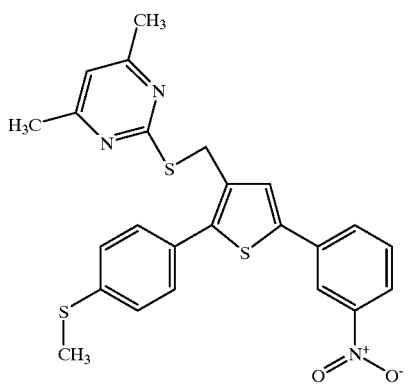
Proton nMR (acetone-d6):8.45 (t, 1H), 8.16 (ddd, 1H), 8.08 (ddd, 1H), 7.83 (s, 1H),7.72 (t, 1H), 7.59 (d, 2H), 7.42 (d, 2H), 4.49 (s, 2H),2.55 (s, 3H), 2.35 (s, 6H).
EXAMPLE 29
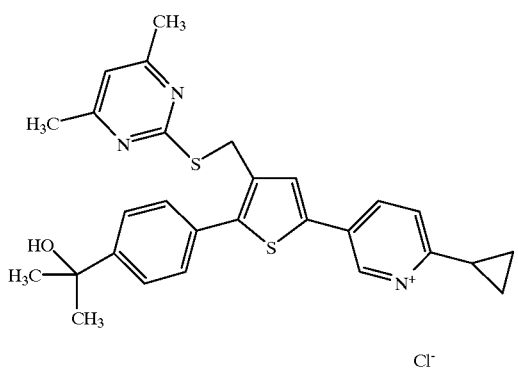
Proton NMR (acetone-d6):8.69 (dd, 1H), 7.84 (dd, 1H), 7.66 (d, 2H), 7.58 (s, 1H), 7.56 (d, 2H), 7.31 (d, 1H), 4.48 (s, 2H), 4.09 (s, 1H), 2.33 (s, 6H), 2.13–2.04 (m, 1H), 1.55 (s, 6H), 1.10–0.97 (m, 4H).
EXAMPLE 30
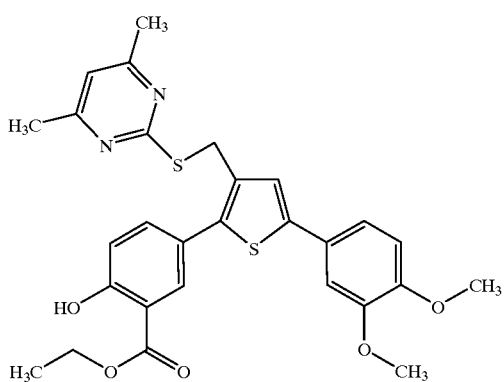
Proton NMR (CDCl3):10.88 (s, 1H), 8.05 (dd, 1H), 7.69 (dd, 1H), 7.32 (s, 1H), 7.13 (dd, 1H), 7.08 (d, 1H), 7.02 (d, 1H), 6.88 (d, 1H), 6.69 (s, 1H), 4.40 (q, 2H), 3.93 (s, 3H), 3.90 (s, 3H), 2.37 (s, 6H), 1.38 (t, 3H).
EXAMPLE 31
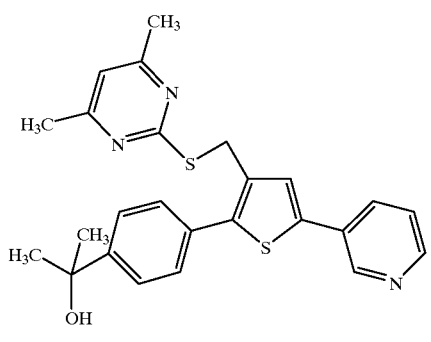
Proton NMR (CDCl3): 8.83 (d, 1H), 8.49 (dd, 1H), 7.82 (dd, 1H), 7.51 (s, 1H), 7.28 (dd, 1H), 6.67 (s, 1H), 4.47 (s, 2H), 2.38 (s, 6H),1.62 (s, 6H).
EXAMPLE 32
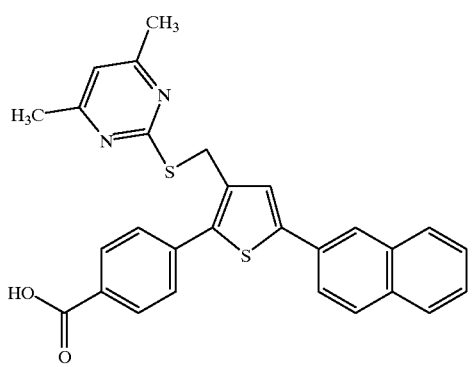
Proton NMR (CDCl3):8.29 (m, 1H), 8.18 (d, 2H), 7.89–7.84 (m, 2H), 7.76 (d, 2H), 7.58 (d, 1H), 7.52–7.46 (m, 3H), 7.40 (s, 1H),6.70 (s, 1H), 4.55 (s, 2H), 2.36 (s, 6H).
EXAMPLE 33
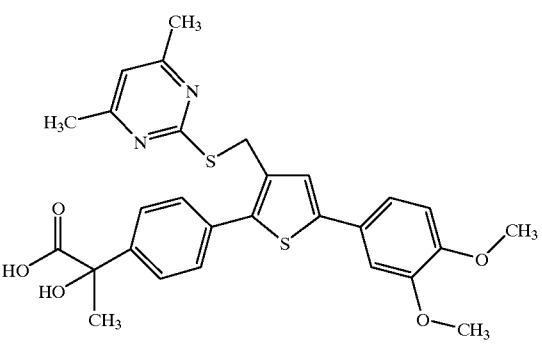
Proton NMR (CDCl3):7.64 (d, 2H), 7.54 (d, 2H), 7.30 (s, 1H), 7.10 (dd, 1H), 7.05 (d, 1H), 6.85 (d, 1H), 6.67 (s, 1H), 4.43 (s, 2H), 3.90 (s, 3H), 3.88 (s, 3H), 3.69 (s, 1H), 2.35 (s, 6H), 1.84 (s, 3H).

EXAMPLE 34
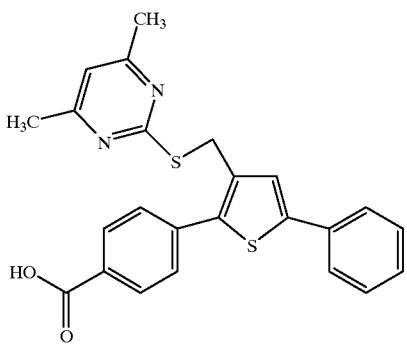
Proton NMR (acetone-d6):8.15 (d, 2H), 7.78 (d, 2H), 7.68 (d, 2H), 7.63 (s, 1H),7.42 (t, 2H), 7.32 (t, 1H), 6.88 (s, 1H), 4.53 (s, 2H),2.32 (s, 6H).
EXAMPLE 35
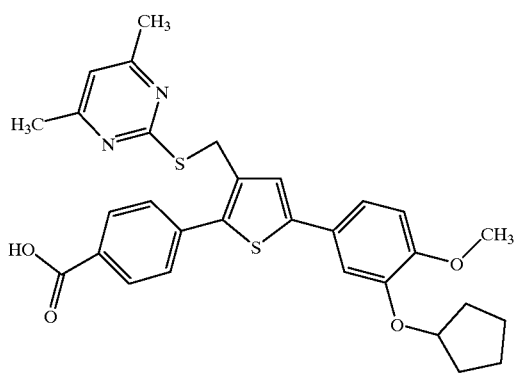
Proton NMR (acetone-d6):11.30 (bs, 1H), 8.14 (d, 2H), 7.76 (d, 2H), 7.51 (s, 1H),7.23–7.18 (m, 2H), 6.99 (d, 1H), 6.90 (s, 1H), 4.90 (m, 1H), 4.50 (s, 2H), 3.82 (s, 3H), 2.32 (s, 6H), 1.95–1.60 (m, 8H).
EXAMPLE 36
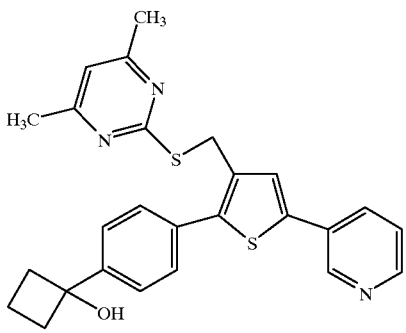
Proton NMR (CDCl3):8.80 (dd, 1H), 8.48 (dd, 1H), 7.83 (dd, 1H), 7.60 (dd, 2H), 7.57 (dd, 2H), 7.50 (s, 1H), 7.29 (dd, 1H), 6.71 (s, 1H), 4.47 (s, 2H), 2.64–2.57 (m, 2H), 2.45–2.40 (m, 3H), 2.39 (s, 6H), 2.07–2.04 (m, 1H), 1.75–1.70 (m, 1H).
EXAMPLE 37
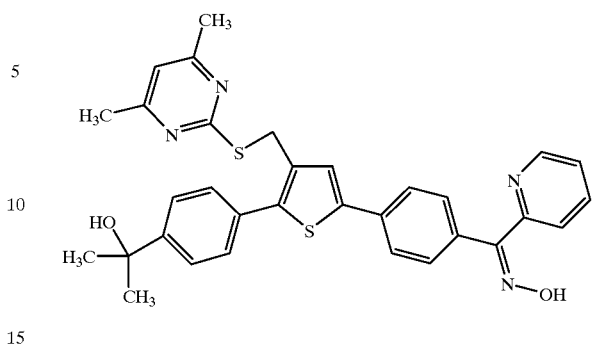
Proton NMR (acetone-d6):10.81 (s, 1H), 8.48 (dd, 1H), 7.93 (dd, 1H), 7.80 (m, 1H), 7.71 (d, 2H), 7.65 (d, 2H), 7.63 (s, 1H), 7.57 (d, 2H), 7.48 (d, 2H), 7.33 (m, 1H), 6.88 (s, 1H), 4.50 (s, 2H), 4.15 (s, 1H), 2.33 (s, 6H), 1.57 (s, 6H).
EXAMPLE 38
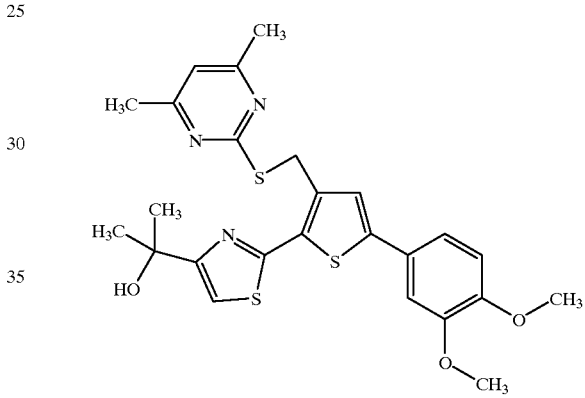
M.P.: 152.7° C.
EXAMPLE 39
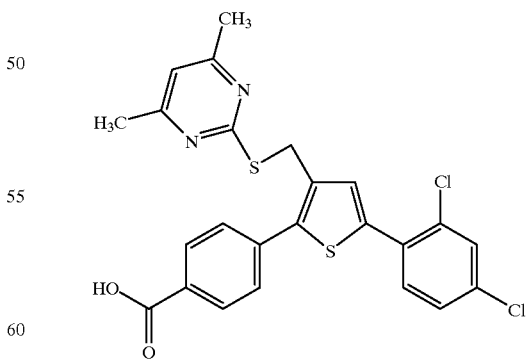
Proton NMR (CDCl3):8.15 (d, 2H), 7.70 (d, 2H), 7.52 (s, 1H), 7.47–7.45 (m, 2H),7.25 (m, 1H), 6.70 (s, 1H), 4.48 (s, 2H), 2.37 (s, 6H).

EXAMPLE 40
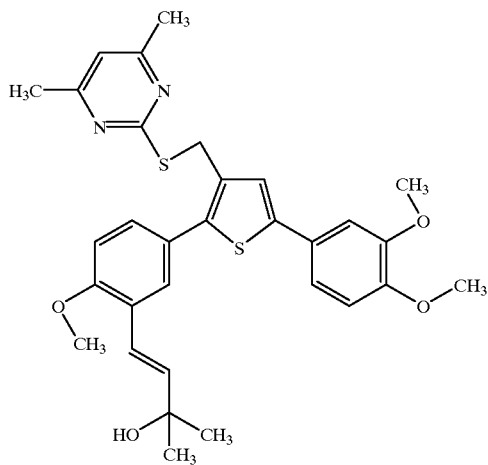
Proton NMR: 7.74 (d, 1H), 7.46 (s, 1H), 7.40 (dd, 1H), 7.23 (d, 1H), 7.18 (dd, 1H), 7.08 (d, 1H), 6.98 (d, 1H), 6.95 (d, 1H) 6.91 (s, 1H), 6.40 (d, 1H), 4.43 (s, 2H), 3.90 (s, 3H) 3.88 (s, 3H), 3.83 (s, 3H), 2.35 (s, 6H), 1.28 (s, 6H).
EXAMPLE 41
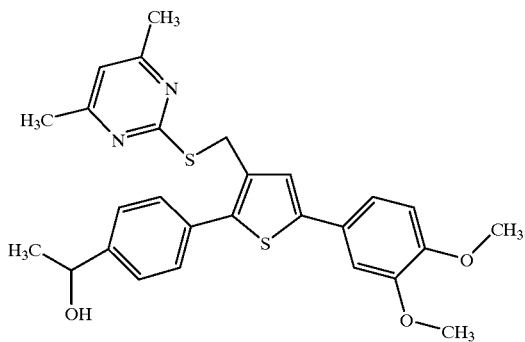
Proton NMR (acetone-d6) 7.56 (d, 2H), 7.50 (d, 2H), 2H), 7.48 (s, 1H), 7.23 (d, 1H), 7.18 (dd, 1H), 6.98 (d, 1H), 6.90 (s, 1H), 4.91 (m, 1H), 4.45 (s, 2H), 4.25 (d, OH), 3.88 (s, 3H), 3.83 (s, 3H) 2.34 (s, 6H), 1.44 (d, 3H).
EXAMPLE 42
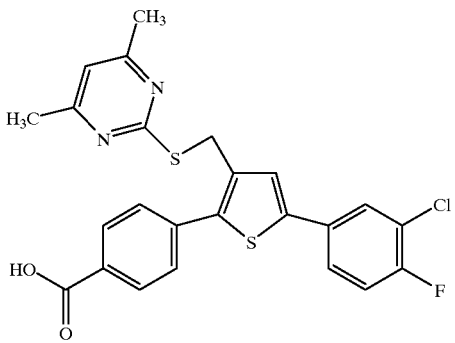
Proton NMR (CDCl3): 8.15 (d, 2H), 7.69 (d, 2H), 7.60 (m, 1H), 7.43 (m, 1H), 7.40 (s, 1H), 7.14 (t, 1H), 6.71 (s, 1H), 4.46 (s, 2H), 2.37 (s, 6H).
EXAMPLE 43
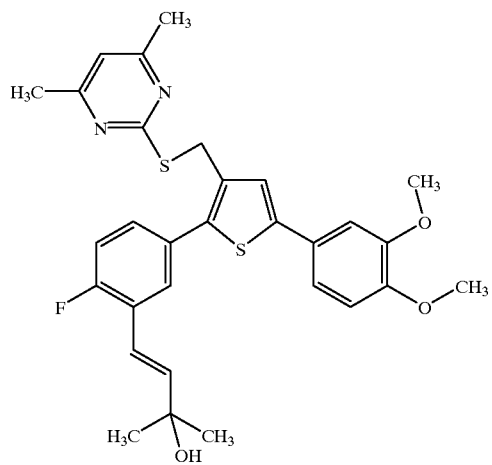
Proton NMR: (acetone-d6) 7.83 (dd, 1H), 7.49 (s, 1H), 7.48 (m, 1H), 7.26–7.18 (m, 3H), 6.99 (d, H), 6.91 (s, 1H), 6.82 (d, 1H), 6.56 (d, 1H), 4.43 (s, 2H), 3.88 (s, 3H) 3.83 (s, 3H), 2.34 (s, 6H), 1.26 (s, 6H).
EXAMPLE 44
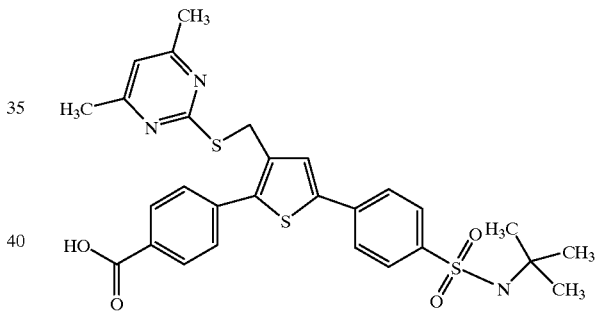
HRMS: 568.1398 (calc.: 568.1400).
EXAMPLE 45
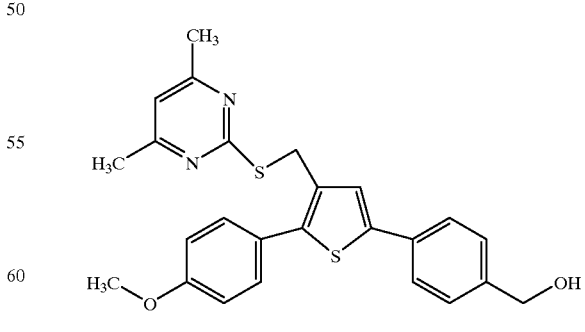
Proton NMR (acetone-d6): 7.60 (d, 2H), 7.56 (d, 2H), 7.53 (s, 1H), 7.39 (d, 2H), 7.04 (d, 2H), 6.89 (s, 1H), 4.64 (d, 2H), 4.44 (s, 2H), 4.21 (t, 1H), 3.85 (s, 3H), 2.35 (s, 6H).

EXAMPLE 46
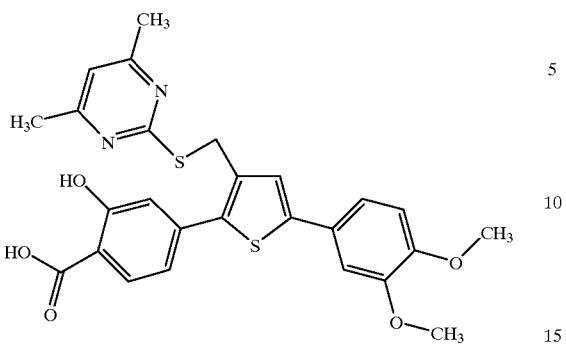
Proton NMR (acetone-d6/DMSO-d6): 7.92 (d, 1H), 7.52 (s, 1H), 7.25–7.16 (m, 4H), 7.00 (d, 1H), 6.91 (s, 1H), 4.52 (s, 2H), 3.88 (s, 3H), 3.83 (s, 3H), 2.36 (s, 6H).
EXAMPLE 47
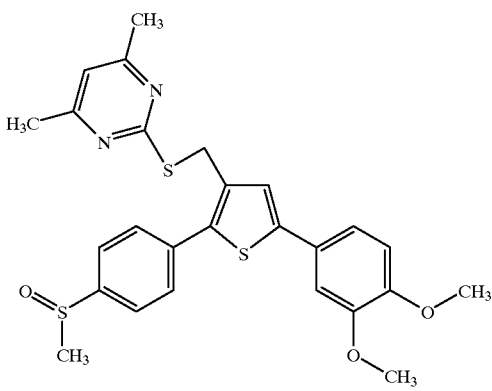
Proton NMR (acetone-d6): 7.80 (s, 4H), 7.51 (s, 1H), 7.24 (d, 1H), 7.20 (dd, 1H), 6.98 (d, 1H), 6.88 (s, 1H), 4.48 (s, 2H), 3.88 (s, 3H), 3.84 (s, 3H), 2.75 (s, 3H), 2.32 (s, 6H).
EXAMPLE 48
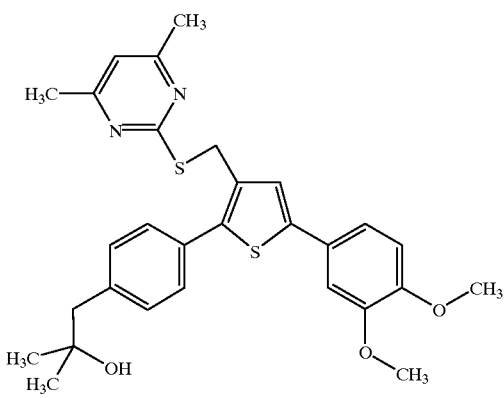
Proton NMR (acetone-d6): 7.52 (d, 2H), 7.47 (s, 1H), 7.37 (d, 1H), 7.23 (d, 1H), 7.17 (dd, 1H), 6.97 (d, 1H), 6.89 (s, 1H), 4.46 (s, 2H), 3.88 (s, 3H), 2.75 (s, (s, 3H), 3.40 (s, 1H, OH), 2.79 (s, 2H), 2.34 (s, 6H), 1.18 (s, 6H).
EXAMPLE 49
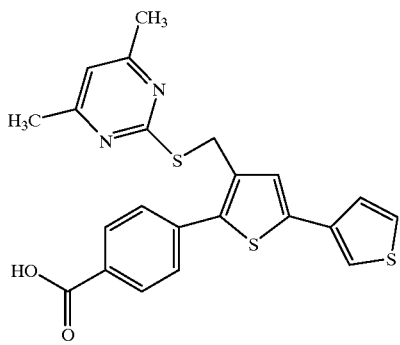
HRMS: 439.0609 (calc.: 439.0610).
EXAMPLE 50
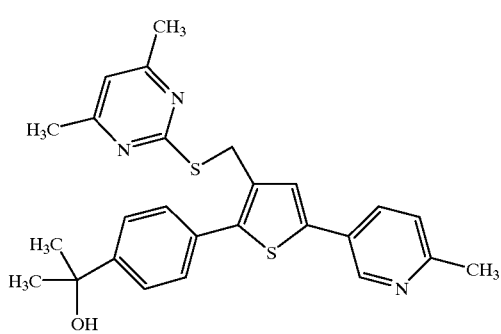
Proton NMR (acetone-d6): 8.74 (d, 1H), 7.88 (dd, 1H), 7.66 (d, 2H), 7.61 (s, 1H), 7.56 (d, 2H), 7.27 (d, 1H), 6.89 (s, 1H), 4.49 (s, 2H), 4.10 (bs, 1H, OH), 2.50 (s, 3H), 2.33 (s, 6H), 1.55 (s, 6H).
EXAMPLE 51
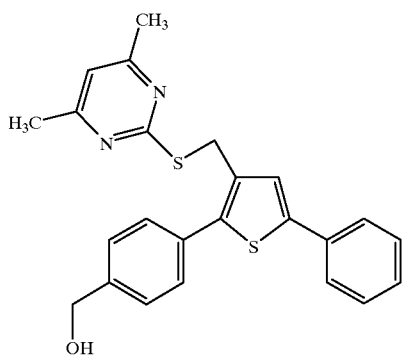
Proton NMR (acetone-d6): 7.66 (d, 2H), 7.60 (d, 2H), 7.58 (s, 1H), 7.50 (d, 2H), 7.48 (t, 2H), 7.30 (t, 1H), 6.89 (s, 1H), 4.70 (d, 2H), 4.47 (s, 2H), 4.32 (t, 1H, OH), 2.34 (s, 6H).

EXAMPLE 52
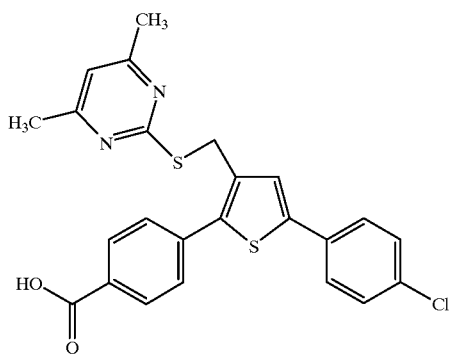
HRMS: 467.0655 (calc.: 467.0654).
EXAMPLE 53
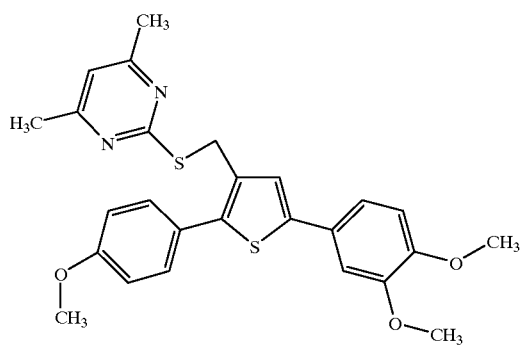
Proton NMR (acetone-d6): 7.54 (d, 2H), 7.44 (s, 1H), 7.21 (d, 1H), 7.15 (dd, 1H), 7.00 (d, 2H), 6.95 (d, 1H), 6.87 (s, 1H), 4.41 (s, 2H), 3.87 (s, 3H), 3.84 (s, 3H), 3.82 (s, 3H), 2.33 (s, 6H).
EXAMPLE 54
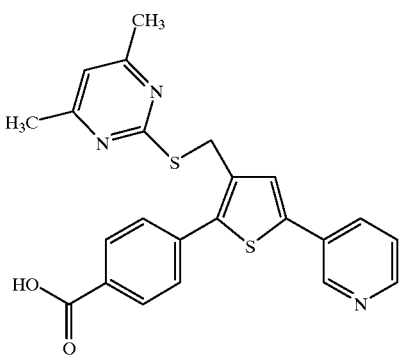
Proton NMR (CDCl3): 8.85 (s, 1H), 8.50 (d, 1H), 8.15 (d, 2H), 7.83 (dm, 1H), 7.68 (d, 2H), 7.50 (s, 1H), 7.30 (dd, 1H), 6.65 (s, 1H), 4.47 (s, 2H), 2.37 (s, 6H).
EXAMPLE 55
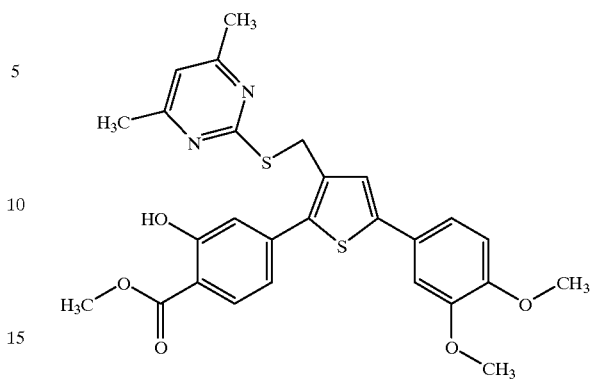
Proton NMR (acetone-d6): 10.83 (s, 1H, OH), 7.93 (d, 1H), 7.52 (s, 1H), 7.25–7.19 (m, 4H), 6.99 (d, 1H), 6.90 (s, 1H), 4.52 (s, 2H), 3.99 (s, 3H), 3.89 (s, 3H), 3.84 (s, 3H), 2.34 (s, 6H).
EXAMPLE 56
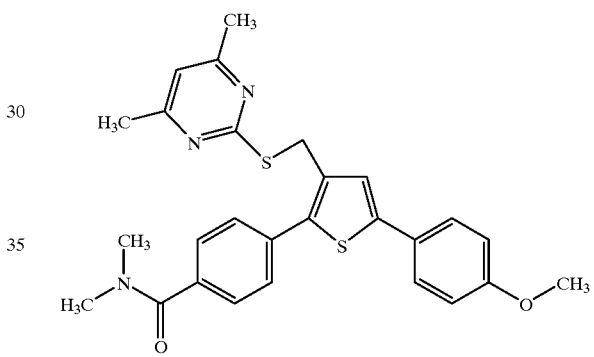
Proton NMR (acetone-d6): 7.68 (d, 2H), 7.60 (d, 2H), 7.54 (d, 2H), 7.47 (s, 1H), 4.50 (s, 2H), 3.83 (s, 3H), 3.02 (s, 6H), 2.33 (s, 6H).
EXAMPLE 57
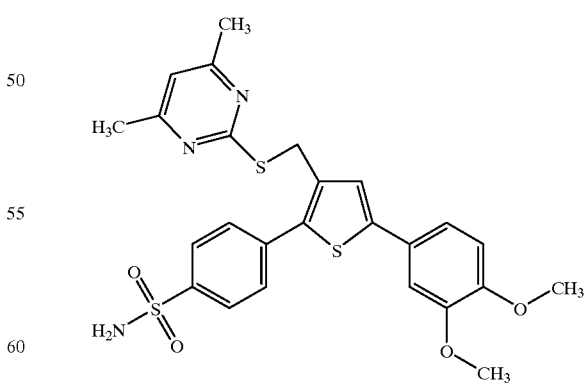
Proton NMR (acetone-d6): 8.00 (d, 2H), 7.80 (d, 2H), 7.53 (s, 1H), 7.25 (d, 1H), 7.21 (dd, 1H), 7.00 (d, 1H), 6.90 (s, 1H), 6.64 (bs, 2H, NH2), 4.50 (s, 2H), 3.89 (s, 3H), 3.84 (s, 3H), 2.33 (s, 6H).

EXAMPLE 58
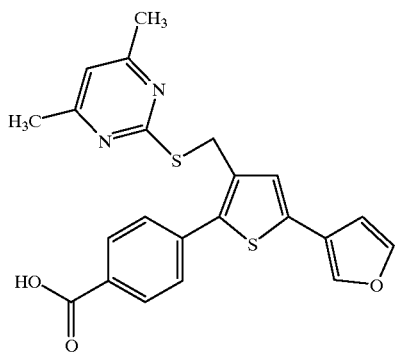
Proton NMR (acetone-d6): 8.12 (d, 2H), 7.97 (bs, 1H), 7.72 (d, 2H), 7.63 (m, 1H), 7.40 (s, 1H), 6.88 (s, 1H), 6.79 (m, 1H), 4.48 (s, 2H), 2.30 (s, 6H).
EXAMPLE 59
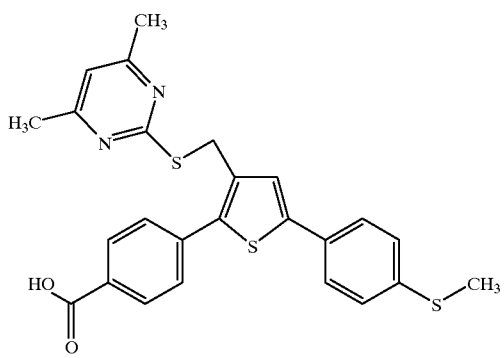
HRMS: 479.0921 (calc.: 479.0919).
EXAMPLE 60
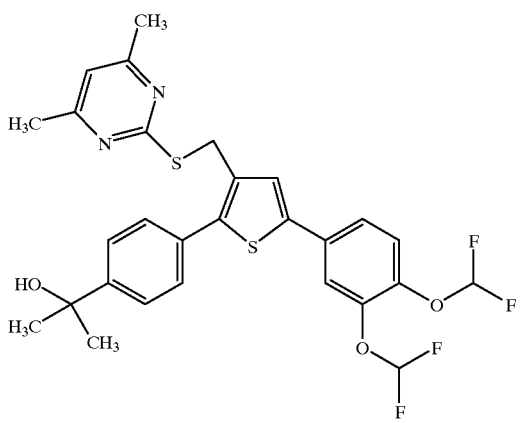
'Proton NMR (acetone-d6): 7.67 (d, 2H), 7.62 (d, 2H), 7.60–7.51 (m, 3H), 7.39 (m, 1H), 7.09 (t, 1H), 7.00 (t, 1H), 6.89 (s, 1H), 4.47 (s, 2H), 4.09 (s, 1H), 2.31 (s, 6H), 1.52 (s, 6H).
EXAMPLE 61
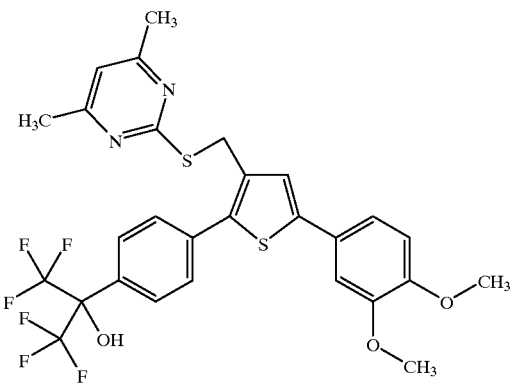
'Proton NMR (acetone-d6): 7.90 (d, 2H), 7.80 (d, 2H), 7.61 (s, 1H), 7.52 (s, 1H), 7.20 (dd, 1H), 7.00 (d, 1H), 6.89 (s, 1H), 4.50 (s, 2H), 3.88 (s, 3H), 3.83 (s, 3H), 2.35 (s, 6H).
EXAMPLE 62
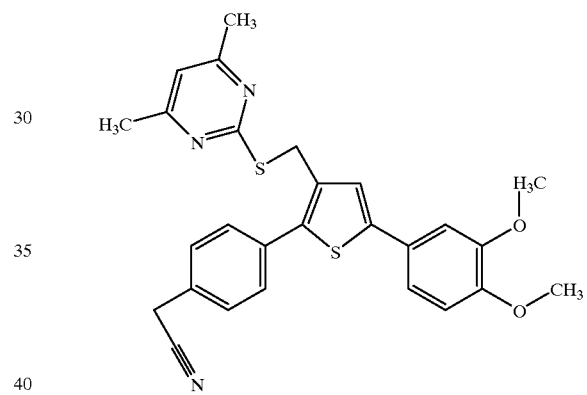
'Proton NMR (acetone-d6): 7.66 (d, 2H), 7.53 (d, 2H), 7.49 (s, 1H), 7.24 (d, 1H), 7.19 (dd, 1H), 6.99 (d, 1H), 6.90 (s, 1H), 4.46 (s, 2H), 4.04 (s, 2H), 3.88 (s, 3H), 2.34 (s, 6H).
EXAMPLE 63
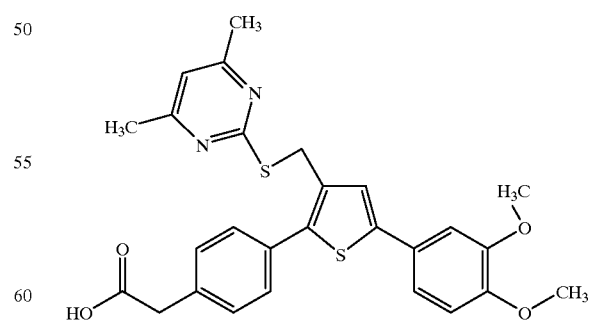
'Proton NMR (acetone-d6): 7.58 (d, 2H), 7.48 (s, 1H), 7.45 (d, 2H), 7.21 (d, 1H), 7.18 (dd, 1H), 6.98 (d, 1H), 6.89 (s, 1H), 4.46 (s, 2H), 3.88 (s, 3H), 3.83 (s, 3H), 3.70 (s, 2H), 2.34 (s, 6H).

EXAMPLE 64
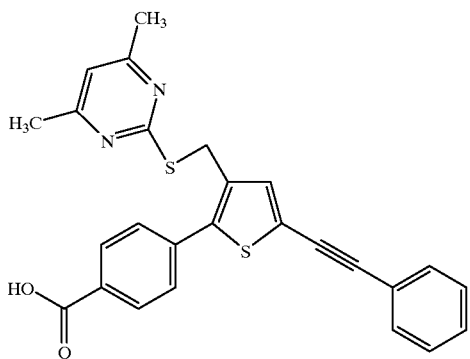
'Proton NMR (acetone-d6): 8.16 (d, 2H), 7.77 (d, 2H), 7.55–7.53 (m, 2H), 7.50 (s, 1H), 7.43–7.41 (m, 3H), 6.90 (s, 1H), 4.50 (s, 2H), 2.32 (s, 6H).
EXAMPLE 65
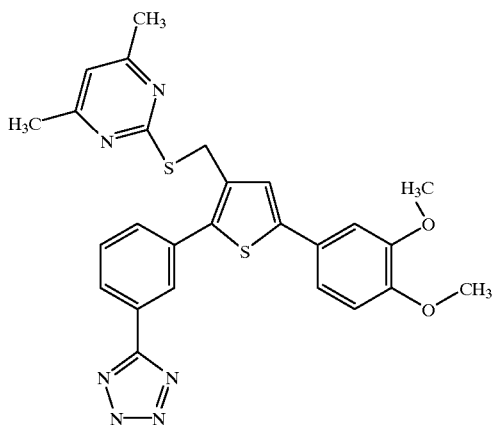
'CIMS: MH+: 517.2.
EXAMPLE 66
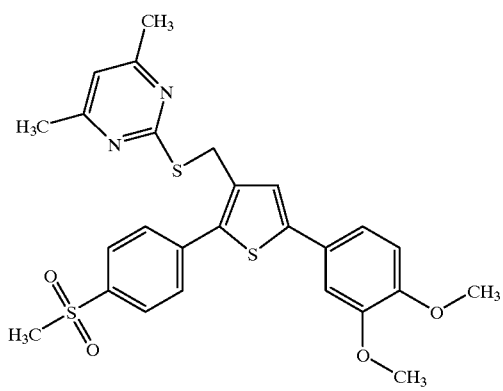
'Proton NMR (acetone-d6): 8.05 (d, 2H), 7.88 (d, 2H), 7.54 (s, 1H), 7.25 (d, 1H), 7.20 (dd, 1H), 7.00 (d, 1H), 6.89 (s, 1H), 4.51 (s, 2H), 3.88 (s, 3H), 3.84 (s, 3H), 3.17 (s, 3H), 2.32 (s, 6H).
EXAMPLE 67
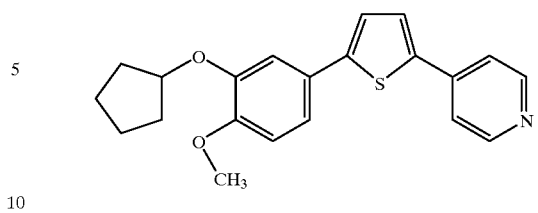
Proton NMR (acetone-d6): 8.55 (d, 2H), 7.71 (d, 1H), 7.59 (d, 2H), 7.41 (d, 1H), 7.28 (s, 1H), 7.26 (d, 1H), 7.00 (d, 1H), 4.92 (m, 1H), 3.85 (s, 3H), 1.95–1.60 (m, 8H).
EXAMPLE 68
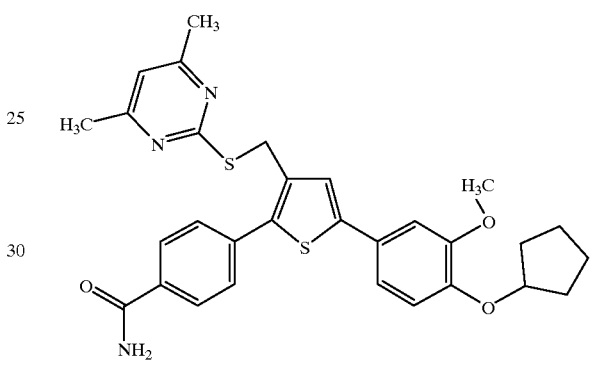
'Proton NMR (acetone-d6): 8.04 (d, 2H), 7.71 (d, 2H), 7.49 (s, 1H), 7.22–7.18 (m, 2H), 6.99 (d, 1H), 6.90 (s, 1H), 4.92 (m, 1H), 4.49 (s, 2H), 3.83 (s, 3H), 2.33 (s, 6H), 2.00–1.60 (m, 8H).
EXAMPLE 69
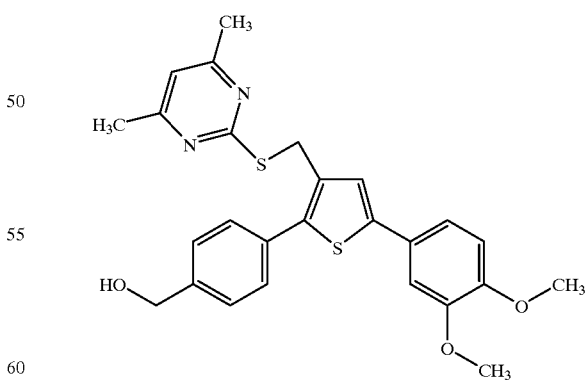
'Proton NMR (CDCl3): 7.58 (d, 2H), 7.40 (d, 2H), 7.33 (s, 1H), 7.14 (dd, 1H), 7.08 (d, 1H), 6.85 (d, 1H), 6.67 (s, 1H), 4.73 (s, 2H), 4.42 (s, 2H), 3.90 (s, 3H), 3.87 (s, 3H).

EXAMPLE 70
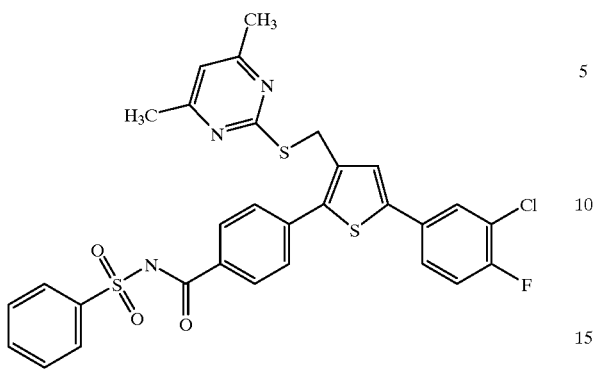
'Proton NMR (acetone-d6): 8.11 (d, 2H), 8.05 (d, 2H), 7.70 (m, 1H), 7.57–7.42 (m, 7H), 7.27 (t, 1H), 6.83 (s, 1H), 4.44 (s, 2H), 2.28 (s, 6H).
EXAMPLE 71
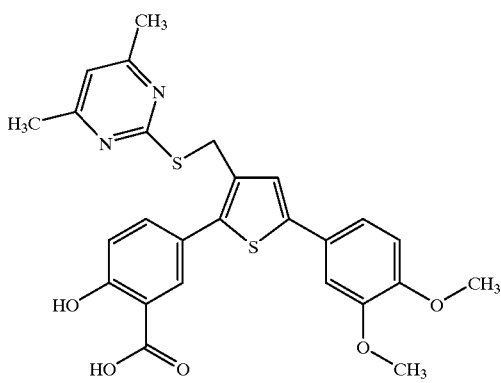
'Proton NMR (acetone-d6): 11.18 (s, 1H), 8.11 (d, 1H), 7.78 (dd, 1H), 7.47 (s, 1H), 7.23 (d, 1H), 7.17 (dd, 1H), 7.08 (d, 1H), 6.96 (d, 1H), 6.87 (s, 1H), 4.42 (s, 2H), 3.88 (s, 3H), 3.83 (s, 3H), 2.33 (s, 6H).
EXAMPLE 72
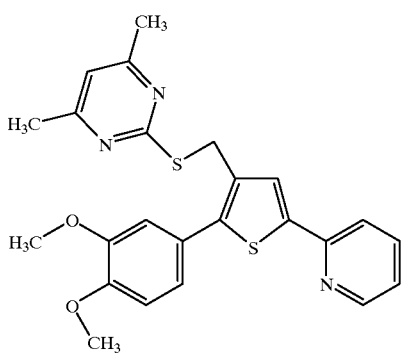
'Proton NMR (acetone-d6): 8.51 (m, 1H), 7.83–7.76 (m, 3H), 7.25–7.16 (m, 3H), 7.07 (d, 1H), 6.91 (s, 1H), 4.48 (s, 2H), 3.86 (s, 3H), 3.83 (s, 3H), 2.36 (s, 6H).
EXAMPLE 73
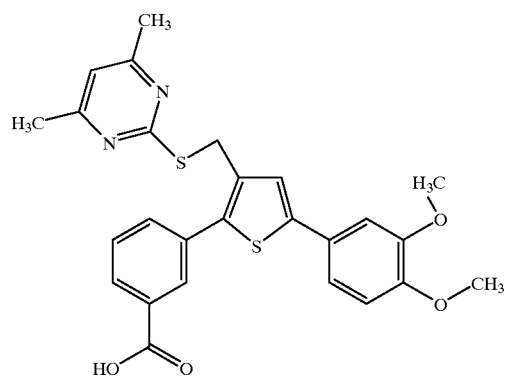
'Anal.: C 63.07, H 4.92, N 5.69, S 12.60; (calc.: C 63.4, H 4.92, N 5.69, S 12.99).
EXAMPLE 74
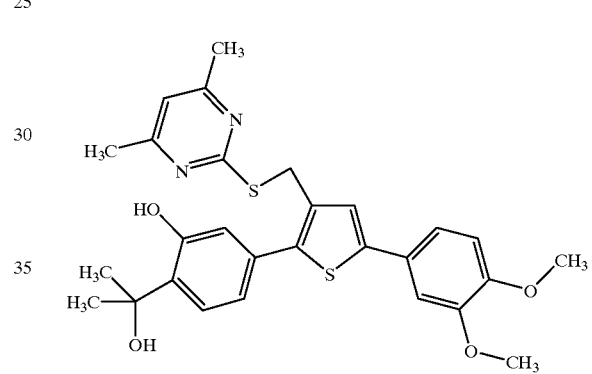
'M.P.: 135.3° C.
EXAMPLE 75
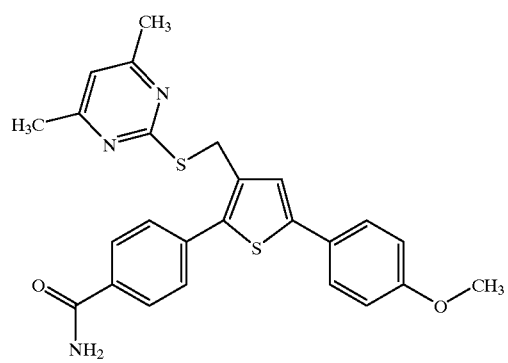
'Proton NMR (CDCl3): 7.88 (d, 2H), 7.69 (d, 2H), 7.50 (d, 2H), 7.36 (s, 1H), 6.90 (d, 2H), 6.70 (s, 1H), 4.46 (s, 2H), 3.85 (s, 3H), 2.36 (s, 6H).

EXAMPLE 76
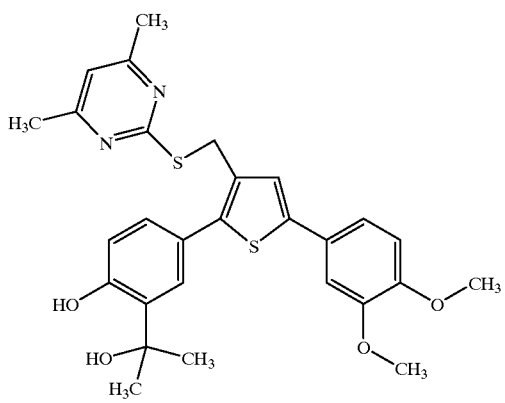
Proton NMR (CDCl3): 9.12 (s, 1H), 7.39 (dd, 1H), 7.32 (d, 1H), 7.31 (s, 1H), 7.13 (dd, 1H), 7.07 (d, 1H), 6.92 (d, 1H), 6.85 (s, 1H), 6.71 (s, 1H), 4.40 (s, 2H), 3.93 (s, 3H), 3.90 (s, 3H), 2.55 (s, 1H), 2.40 (s, 6H), 1.69 (s, 6H).
EXAMPLE 77
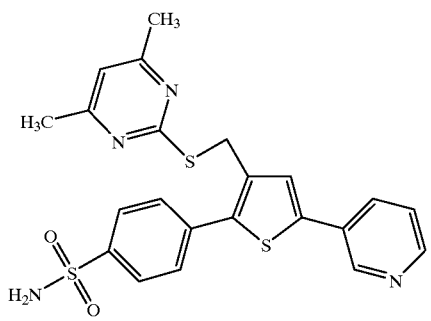
'Proton NMR (acetone d-6): 8.90 (dd, 1H), 8.52 (dd, 1H), 8.05–8.01 (m, 3H), 7.83 (d, 2H), 7.74 (s, 1H), 7.43 (ddd, 1H), 6.90 (s, 1H), 6.67 (bs, 2H, NH2), 4.53 (s, 2H), 2.32 (s, 6H).
EXAMPLE 78
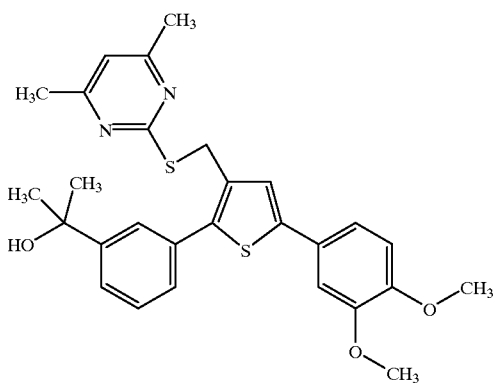
'M.P.: 146.1° C.
EXAMPLE 79
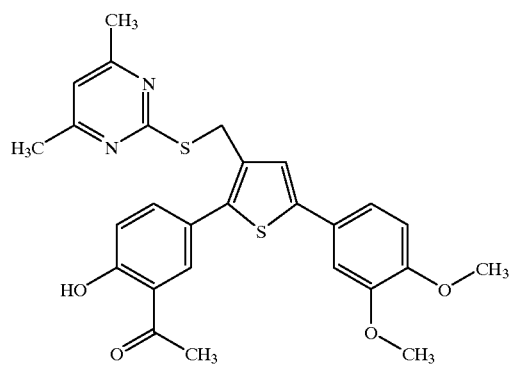
'Proton NMR (acetone-d6): 12.33 (s, 1H), 8.08 (d, 1H), 7.71 (dd, 1H), 7.44 (s, 1H), 7.20 (d, 1H), 7.13 (dd, 1H), 7.02 (d, 1H), 6.93 (d, 1H), 6.86 (s, 1H), 4.42 (s, 2H), 3.87 (s, 3H), 3.81 (s, 3H), 2.63 (s, 3H), 2.32 (s, 6H).
EXAMPLE 80
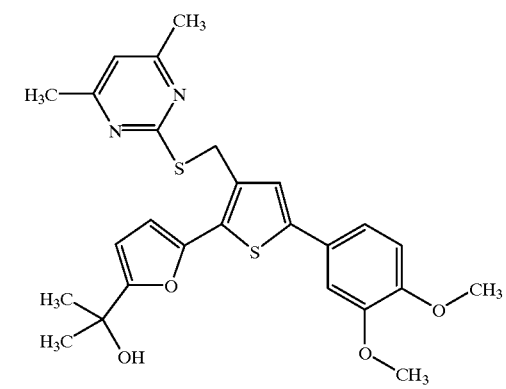
'Proton NMR (acetone-d6): 7.45 (s, 1H), 7.19 (d, 1H), 7.15 (dd, 1H), 6.97 (d, 1H), 6.89 (s, 1H), 6.575 (d, 1H), 6.36 (d, 1H), 4.60 (s, 2H), 4.32 (s, 1H, OH), 3.88 (s, 3H), 3.82 (s, 3H), 2.37 (s, 6H), 1.57 (s, 6H).
EXAMPLE 81
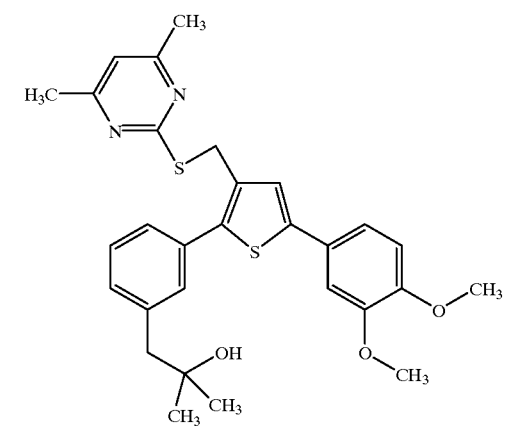
Proton NMR (acetone-d6): 7.51 (t, 1H), 7.48 (s, 1H), 7.45 (dt, 1H), 7.37 (t, 1H) 7.29 (dt, 1H), 7.22 (d, 1H), 7.17 (dd, 1H), 6.97 (d, 1H), 6.89 (s, 1H), 4.45 (s, 2H), 3.88 (s, 3H), 3.82 (s, 3H), 3.40 (s, 1H, OH), 2.80 (s, 2H), 2.34 (s, 6H), 1.16 (s,.6H).

EXAMPLE 82

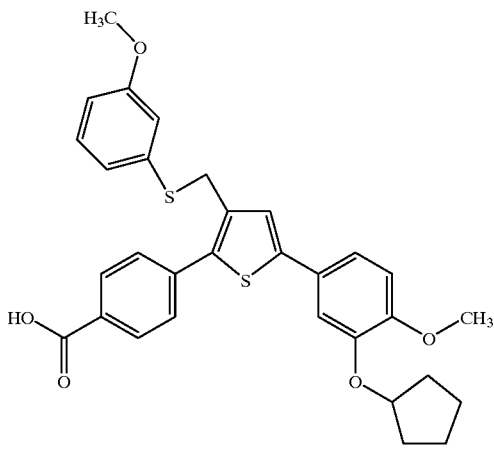

'Proton NMR (CDCl3): 8.11 (d, 2H), 7.56 (d, 2H), 7.18–7.06 (m, 4H), 6.91–6.82 (m, 3H), 6.75 (m, 1H), 4.83 (m, 1H), 4.14 (s, 2H), 3.86 (s, 3H), 3.72 (s, 3H), 2.00–1.60 (m, 8H).

EXAMPLE 83

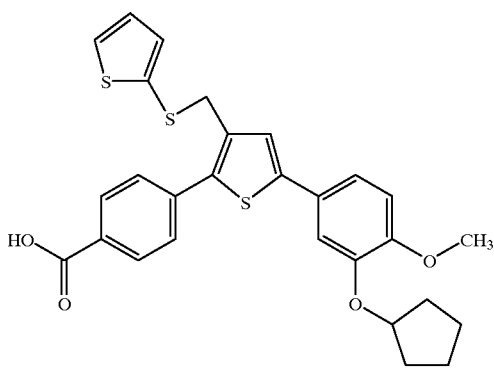

'Proton NMR (acetone-d6): 8.07 (d, 2H), 7.55 (dd, 1H), 7.52 (d, 2H), 7.25 (s, 1H), 7.20 (m, 2H), 7.08 (dd, 1H), 7.03–6.99 (m, 2H), 4.12 (s, 2H), 3.85 (s, 3H), 2.00–1.60 (m, 8H).

EXAMPLE 84

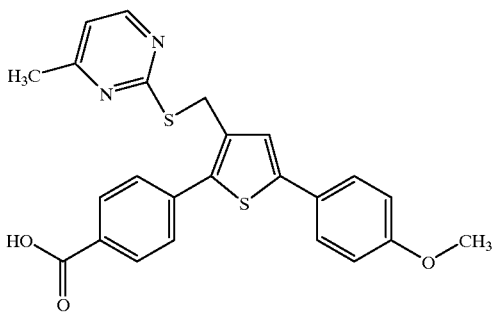

'Proton NMR (DMSO-d6): 8.43 (d, 1H), 8.01 (d, 2H), 7.67 (d, 2H), 7.58 (d, 2H), 7.49 (s, 1H), 7.09 (d, 1H), 6.99 (d, 2H), 4.46 (s, 2H), 3.78 (s, 3H), 2.30 (s, 3H).

EXAMPLE 85

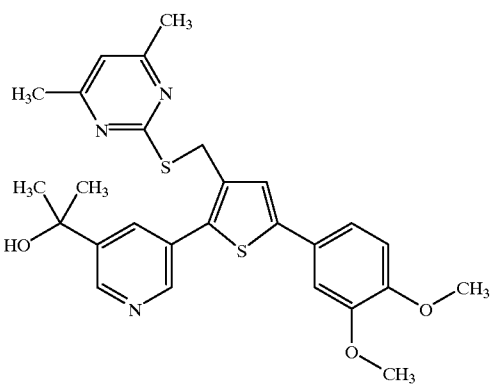

Proton NMR (acetone-d6): 8.76 (d, 1H), 8.68 (d. 1H), 8.09 (t, 1H), 7.52 (s, 1H) 7.24 (d, 1H), 7.20 (dd, 1H), 7.00 (d, 1H), 6.88 (s, 1H) 4.46 (s, 2H), 3.88 (s, 3H), 3.83 (s, 3H), 2.32 (s, 6H), 1.58 (s, 6H).

EXAMPLE 86

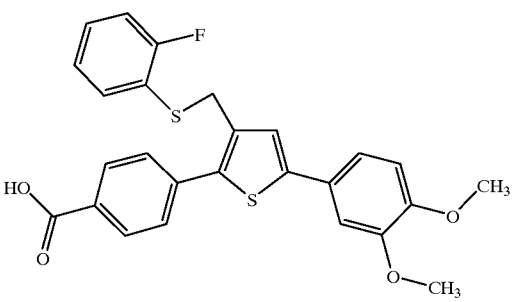

'Proton NMR (acetone d-6): 8.10 (d, 2H), 7.67 (d, 2H), 7.43–7.30 (m, 3H), 7.21 (d, 1H), 7.20 (dd, 1H), 7.13 (d, 1H), 7.12 (m, 1H), 7.00 (d, 2H), 4.27 (s, 2H), 3.89 (s, 3H), 3.84 (s, 3H).

EXAMPLE 87

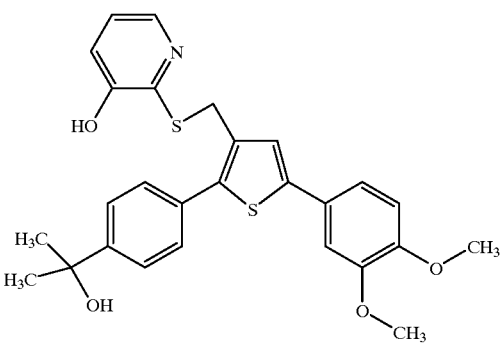

'Proton NMR (acetone d-6): 9.22 (bs, 1H, OH), 8.01 (dd, 1H), 7.62 (d, 2H), 7.53 (d, 2 h), 7.44 (s, 1H), 7.23 (d, 1H), 7.17 (dd, 1H), 7.12 (dd, 1H), 7.00–6.96 (m, 2H), 4.47 (s, 2H), 4.13 (s, 1H, OH), 3.88 (s, 3H), 3.83 (s, 3H), 1.56 (s, 6H).

EXAMPLE 88
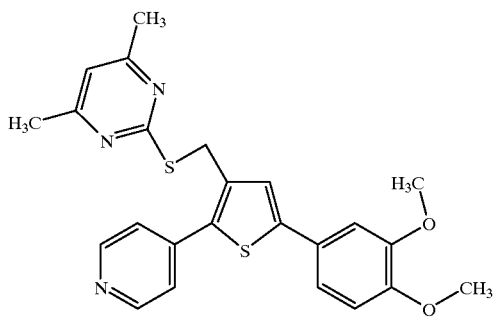
'Proton NMR (CDCl3): 8.62 (m, 2H), 7.50 (m, 2H), 7.34 (s, 1H), 7.14 (dd, 1H), 7.07 (d, 1H), 6.86 (d, 1H), 6.69 (s, 1H), 4.50 (s, 2H), 3.93 (s, 3H), 3.88 (s, 3H), 2.35 (s, 6H).
EXAMPLE 89
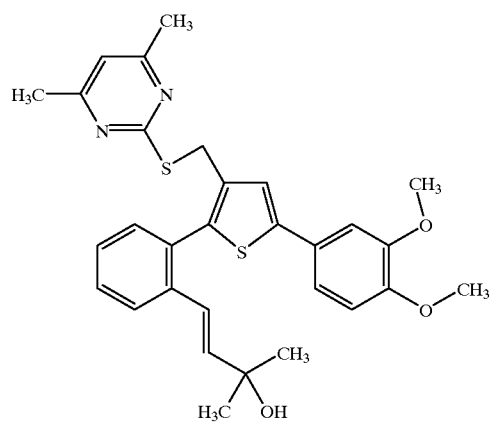
'Proton NMR (acetone-d6): 7.70 (dd, 1H), 7.46 (s, 1H), 7.45–7.30 (m, 3H) 7.23 (d, 1H), 7.17 (dd, 1H), 6.97 (d, 1H), 6.85 (s, 1H) 6.66 (d, 2H), 6.45 (d, 1H), 4.18 (s, 2H), 3.88 (s, 3H), 3.83 (s, 3H), 2.31 (s, 6H), 1.31 (s, 6H).
EXAMPLE 90
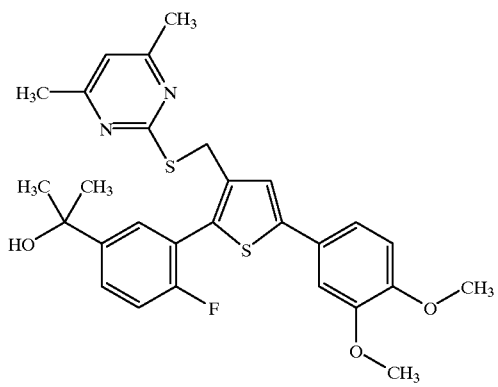
Proton NMR (acetone-d6): 7.71 (dd, 1H), 7.62 (m, 1H), 7.50 (s, 1H), 7.25–7.17 (m, 3H), 6.98 (d, 1H), 6.87 (s, 1H), 4.35 (s, 2H), 3.88 (s, 3H), 3.83 (s, 3H), 2.31 (s, 6H), 1.54 (s, 6H).
EXAMPLE 91
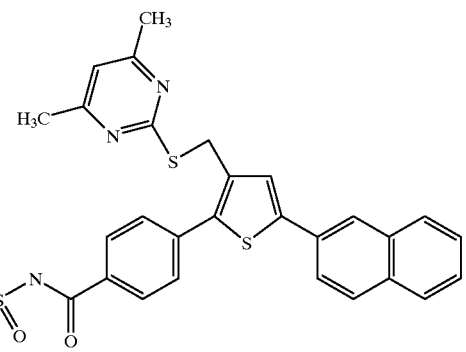
'Proton NMR (acetone-d6): 8.28 (m, 1H), 8.16 (d, 2H), 8.00 (m, 2H), 7.85 (d, 2H), 7.64 (m, 1H), 7.57–7.53 (m, 3H), 7.51 (s, 1H), 6.90 (s, 1H), 4.60 (s, 2H), 3.42 (s, 3H), 2.32 (s, 6H).
EXAMPLE 92
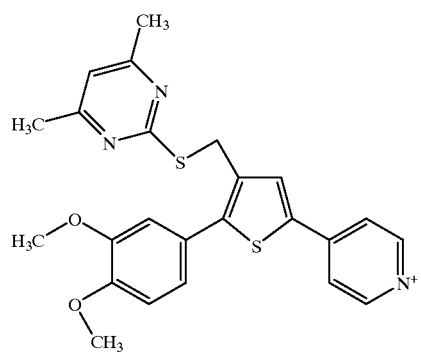
'Proton NMR (acetone-d6): 8.83 (d, 2H), 8.29 (s, 1H), 8.27 (d, 2H), 7.25–7.20 (m, 2H), 7.11 (d, 1H), 6.93 (s, 1H), 4.55 (s, 2H), 3.88 (s, 3H), 3.84 (s, 3H), 2.35 (s, 6H).
EXAMPLE 93
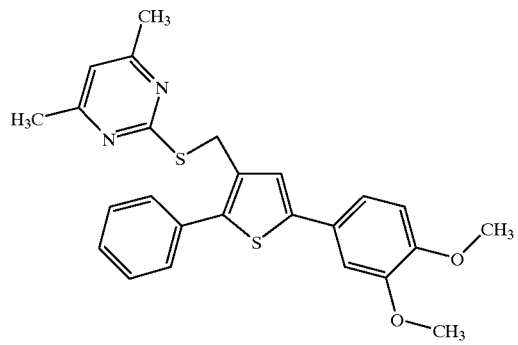
'Proton NMR (CDCl3): 7.60 (dd, 2H), 7.44 (t, 2H), 7.44–7.40 (m, 2H), 7.14 (dd, 1H), 7.08 (d, 1H), 6.86 (d, 1H), 6.68 (s, 1H), 4.46 (s, 2H), 3.93 (s, 3H), 3.90 (s, 3H), 2.37 (s, 6H).

EXAMPLE 94
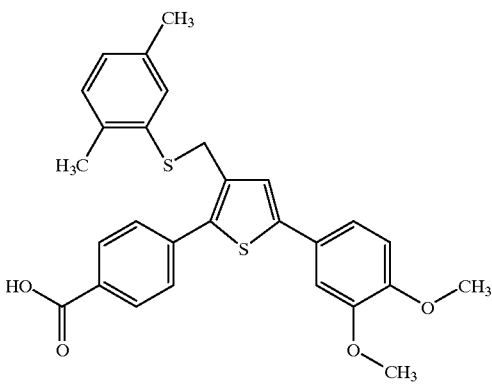
'Proton NMR (acetone d-6): 8.09 (d, 2H), 7.64 (d, 2H), 7.33 (s, 1H), 7.21–7.18 (m, 2H), 7.11 (bs, 1H), 7.06 (d, 1H), 7.00 (d, 1H), 6.95 (bd, 1H), 4.19 (s, 2H), 3.89 (s, 3H), 3.85 (s, 3H).
EXAMPLE 95
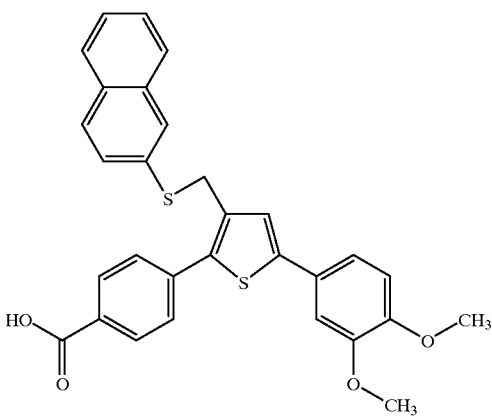
Proton NMR (acetone d-6): 8.07 (d, 2H), 7.87–7.73 (m, 4H), 7.65 (d, 2H), 7.51–7.42 (m, 3H), 7.41 (s, 1H), 7.18–7.16 (m, 2H), 6.98 (d, 1H), 4.40 (s, 2H), 3.84 (s, 3H), 3.83 (s, 3H).
EXAMPLE 96
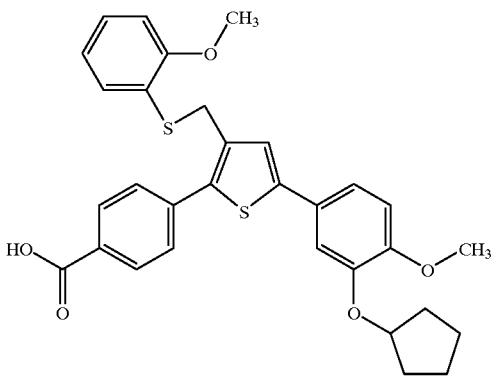
'Proton NMR (CDCl3): 8.11 (d, 2H), 7.59 (d, 2H), 7.26–7.20 (m, 2H), 7.17 (s, 1H), 7.10 (dd, 1H), 7.07 (d, 1H), 6.88–6.79 (m, 3H), 4.83 (m, 1H), 4.12 (s, 2H), 3.86 (s, 3H), 3.80 (s, 3H), 2.00–1.60 (m, 8H).
EXAMPLE 97
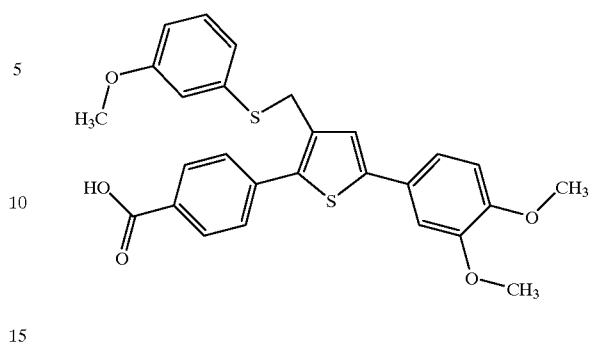
'Proton NMR (acetone d-6): 8.09 (d, 2H), 7.65 (d, 2H), 7.39 (s, 1H), 7.23–7.17 (m, 3H), 7.00 (d, 1H), 6.91 (dm, 1H), 6.88 (t, 1H), 6.79 (ddd, 1H), 4.28 (s, 2H), 3.89 (s, 3H), 3.85 (s, 3H), 3.73 (s, 3H).
EXAMPLE 98
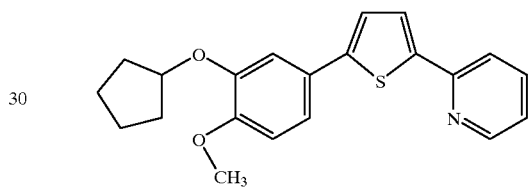
Proton NMR (acetone-d6): 8.52 (d, 1H), 7.83 (m, 2H), 7.71 (d, 1H), 7.38 (d, 1H), 7.25 (m, 3H), 7.00 (d, 1H), 4.95 (m, 1H), 3.82 (s, 3H), 1.95–1.60 (m, 8H).
EXAMPLE 99
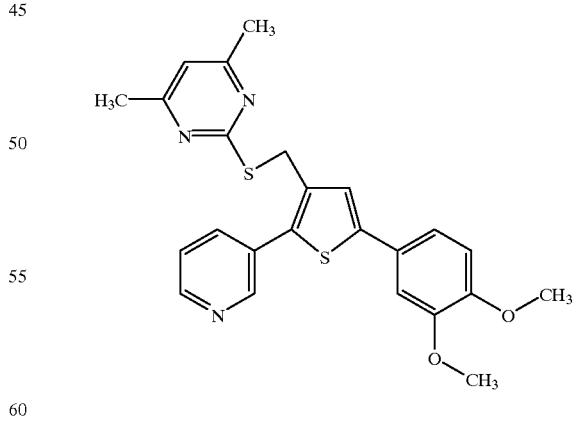
'Proton NMR (acetone-d6): 8.81 (m, 1H), 8.59 (dd, 1H), 7.99 (dm, 1H), 7.52 (s, 1H), 7.50 (m, 1H), 7.25 (d, 1H), 7.20 (dd, 1H), 7.00 (d, 1H), 6.89 (s, 1H), 4.47 (s, 2H), 3.88 (s, 3H), 3.85 (s, 3H), 2.33 (s, 6H).

EXAMPLE 100
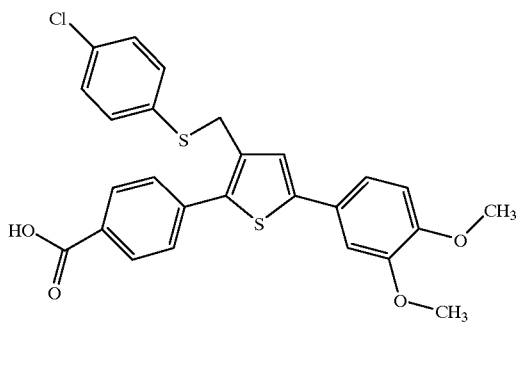
'Proton NMR (acetone d-6): 810 (d, 2H), 7.64 (d, 2H), 7.38 (s, 1H), 7.34–7.28 (m, 4H), 7.23–7.19 (m, 2H), 7.00 (d, 1H), 4.29 (s, 2H), 3.90 (s, 3H), 3.85 (s, 3H).
EXAMPLE 101
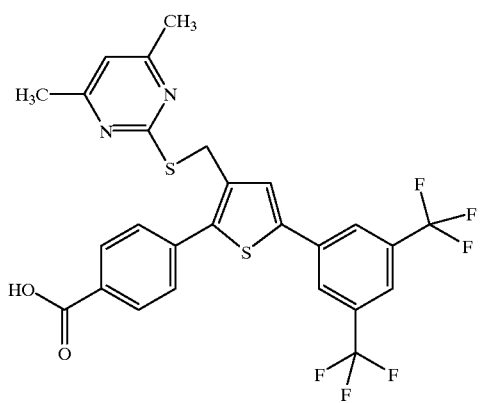
'Anal.: C 54.04, H 3.16, N 4.71.
EXAMPLE 102
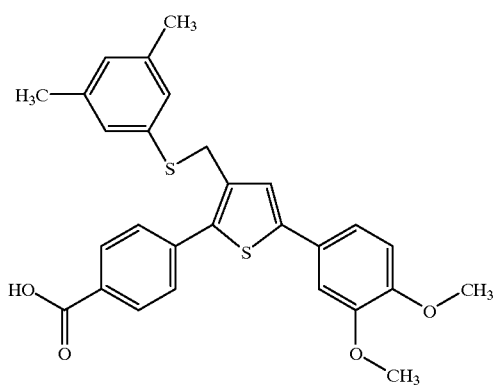
Proton NMR (acetone-d6): 8.10 (d, 2H), 7.64 (d, 2H), 7.37 (s, 1H), 7.23–7.18 (m, 2H), 7.00 (d, 1H), 6.92 (s, 2H), 6.85 (s, 1H), 4.23 (s, 2H), 3.89 (s, 3H), 3.84 (s, 3H), 2.18 (s, 6H).
EXAMPLE 103
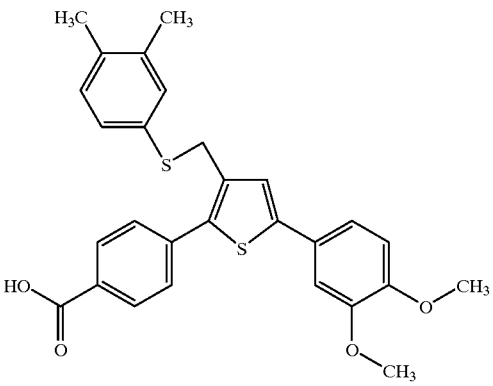
'Proton NMR (acetone-d6): 8.08 (d, 2H), 7.60 (d, 2H), 7.35 (s, 1H), 7.22 (d, 1H), 7.20 (dd, 1H), 7.09 (bs, 1H), 7.06–6.99 (m, 3H), 4.19 (s, 2H), 3.89 (s, 3H), 3.85 (s, 3H), 2.20 (s, 3H), 2.15 (s, 3H).
EXAMPLE 104
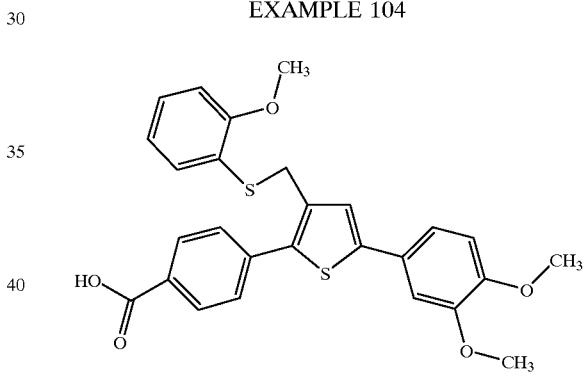
'Proton NMR (acetone-d6): 8.11 (d, 2H), 7.70 (d, 2H), 7.36 (s, 1H), 7.29–7.18 (m, 4H), 7.00 (d, 1H), 6.95 (dd, 1H), 6.87 (td, 1H), 4.20 (s, 2H), 3.90 (s, 3H), 3.84 (s, 3H), 3.80 (s, 3H).
EXAMPLE 105
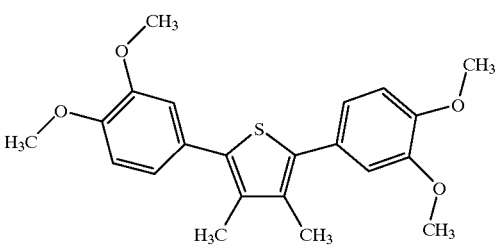

EXAMPLE 106
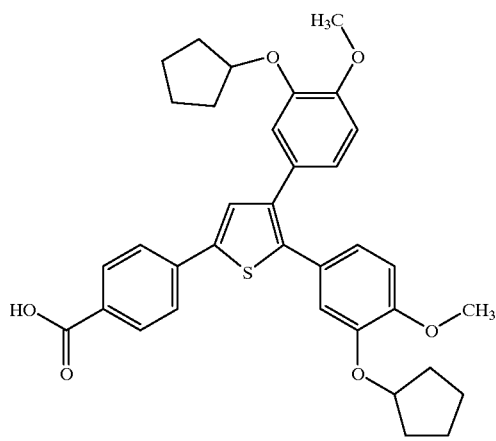
'M.P.: 113.9° C.
EXAMPLE 107
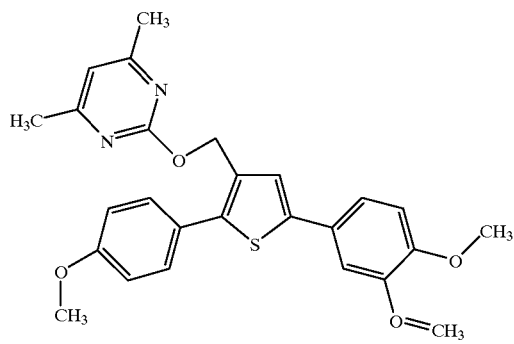
Proton NMR (acetone-d6): 7.56 (dd, 2H), 7.51 (s, 1H), 7.25 (d, 1H), 7.19 (dd, 1H), 7.05 (dd, 2H), 6.98 (d, 1H), 6.83(s, 1H), 5.32 (s, 2H), 3.89 (s, 3H), 3.85 (s, 3H), 3.83 (s, 3H), 2.35 (s, 6H).
EXAMPLE 108
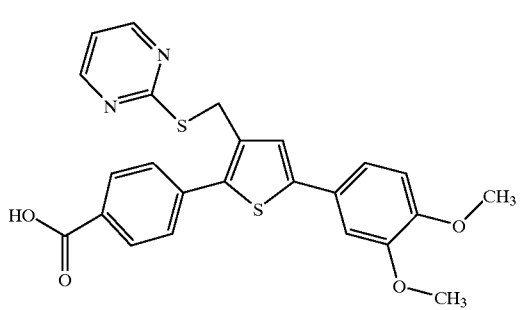
Proton NMR (acetone-d6): 8.57 (d, 2H), 8.14 (d, 2H), 7.75 (d, 2H), 7.52 (s, 1H), 7.26 (d, 1H), 7.21 (dd, 1H), 7.17 (t, 1H), 7.00 (d, 1H), 4.52 (s, 2H), 3.89 (s, 3H), 3.84 (s, 3H).
EXAMPLE 109
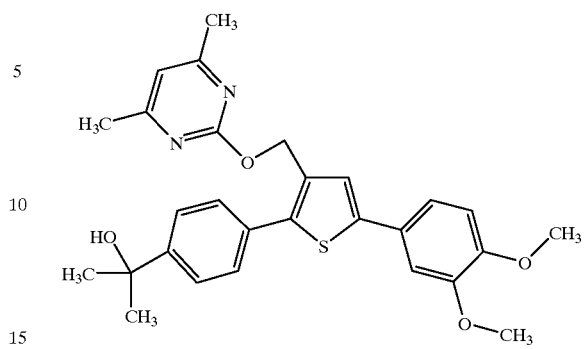
'Proton NMR (acetone-d6): 7.64 (dd, 2H), 7.58 (dd, 2H), 7.55 (s, 1H), 7.27 (d, 1H), 7.20 (dd, 1H), 6.99 (d, 1H), 6.83 (s, 1H), 5.36 (s, 2H), 3.90 (s, 3H), 3.84 (s, 3H), 2.35 (s, 6H), 1.55 (s, 6H).
EXAMPLE 110
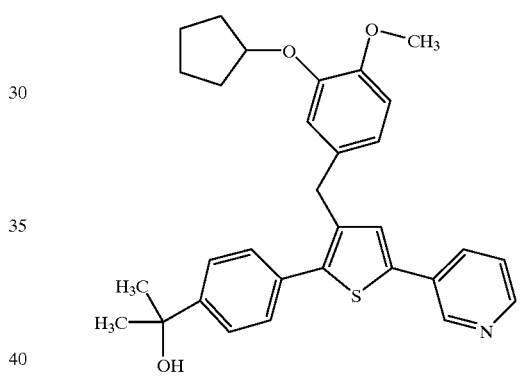
'Proton NMR (acetone-d6): 8.87 (d, 1H), 8.48 (dd, 1H), 7.99 (dt, 1H), 7.64 (d, 2H), 7.49 (d, 2H), 7.42 (s, 1H), 7.40 (m, 1H), 6.85 (d, 1H), 6.75–6.70 (m, 2H), 4.70 (m, 1H), 4.15 (s, 1H, OH), 4.01 (s, 2H), 3.74 (s, 3H), 1.70–1.50 (m, 14H).
EXAMPLE 111
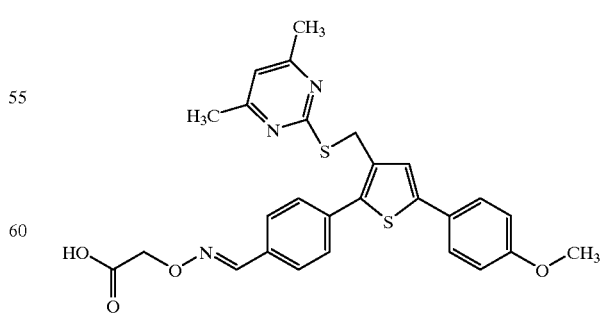
'M.P.: 171.9° C. (decomposed).

EXAMPLE 112

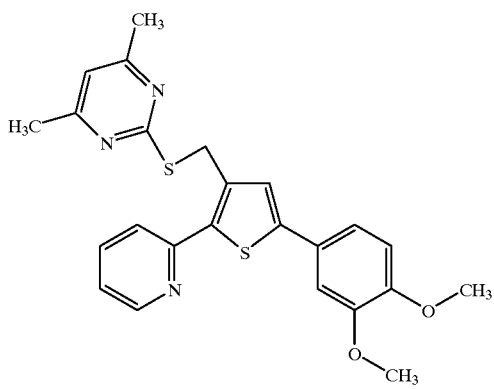

Proton NMR (acetone d-6): 8.63 (dm, 1H), 7.86 (td, 1H), 7.78 (dm, 1H), 7.53 (s, 1H), 7.30–7.20 (m, 3H), 6.99 (d, 1H), 6.88 (s, 1H), 4.81 (s, 2H), 3.90 (s, 3H), 3.83 (s, 3H), 2.36 (s, 6H).

EXAMPLE 113

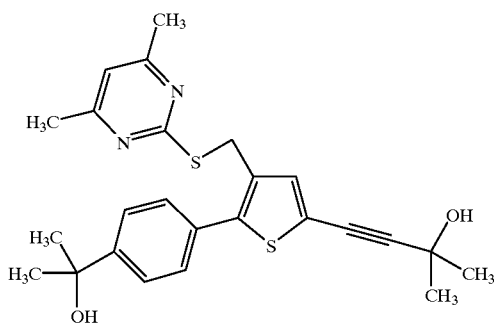

'Proton NMR (acetone-d6): 7.63 (d, 2H), 7.50 (d, 2H), 7.26 (s, 1H), 6.88 (s, 1H), 4.48 (s, 1H), 4.41 (s, 2H), 4.06 (s, 1H), 2.31 (s, 6H), 1.52 (s, 6H), 1.50 (s, 6H).

EXAMPLE 114

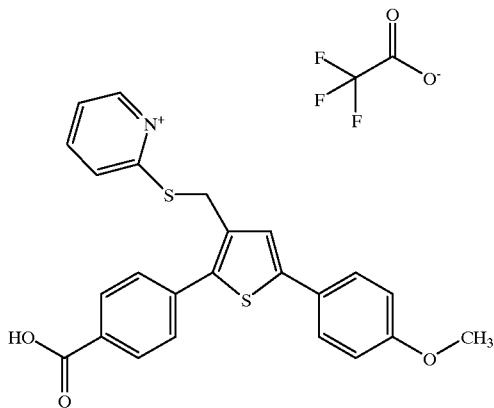

'Proton NMR (acetone d-6): 8.45 (m, 1H), 8.12 (d, 2H), 7.73 (d, 2H), 7.71 (m, 1H), 7.59 (d, 2H), 7.44 (s, 1H), 7.30 (d, 1H), 7.14 (m, 1H), 6.98 (d,2H), 4.56 (s, 2H), 3.83 (s, 3H).

EXAMPLE 115

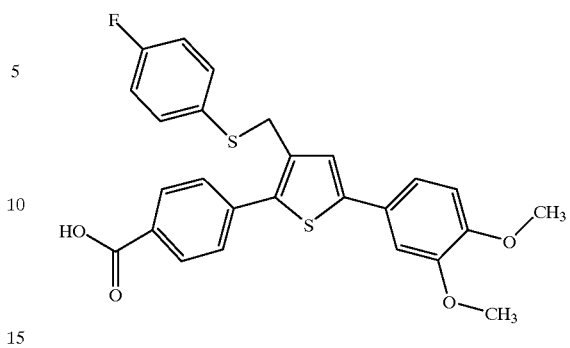

Proton NMR (acetone-d6): 8.09 (d, 2H), 7.61 (d, 2H), 7.41–7.38 (m, 2H), 7.33 (s, 1H), 7.22–7.19 (m, 2H), 7.08–7.04 (m, 2H), 7.01 (d, 1H), 4.23 (s, 2H), 3.89 (s, 3H), 3.85 (s, 3H).

EXAMPLE 116

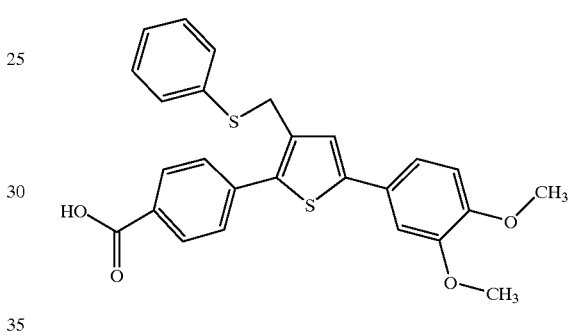

Proton NMR (acetone-d6): 8.10 (d, 2H), 7.66 (d, 2H), 7.36–7.34 (m, 2H), 7.31–7.18 (m, 5H), 7.00 (d, 1H), 4.27 (s, 2H), 3.89 (s, 3H), 3.84 (s, 3H).

EXAMPLE 117

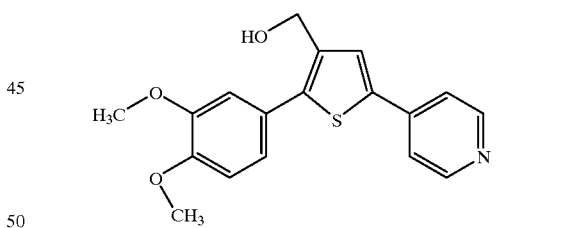

'Proton NMR (acetone-d6): 8.57 (m, 2H), 7.76 (s, 1H), 7.59 (m, 2H), 7.26 (d, 1H), 7.15 (dd, 1H), 7.04 (d, 1H), 4.64 (d, 2H), 4.38 (t, 1H, OH), 3.87 (s, 3H), 3.86 (s, 3H).

Methods of Synthesis

The compounds of the present invention can be prepared by the methods described below. It will be apparent to one skilled in the art that similar methodology could be used to prepare the enantiomers or the racemates of the illustrated compounds.

Method 1

A variety of organic acids (bromobenzoic acids, bromophenylacetic acids, bromophenylpropionic acids, bromocinnamic acids, bromonicotinic acids, bromothiophenecarboxylic acids and bromofuroic acid, etc.) was loaded onto a Merrifield resin or a Wang resin according to known prior art [see: a) Gisin B. F. (1973) *Helv. Chim. Acta* 56, 1476; b)

Wang S.-W. (1973) *J. Am. Chem. Soc.* 95, 1382; c) Lu G. et al (1981) *J. Org. Chem.* 46, 3433]. The palladium catalyzed cross-coupling reactions of these resin bound arylbromides with boronic acid 1 (the Suzuki reaction) were carried out according to the standard procedure described in the experimental to yield intermediates II (for a review of the Suzuki coupling reactions, see: Miyaura N. and Suzuki A. (1995) *Chem. Rev.* 95, 2457–2483; for an example of the Suzuki reaction on solid support, see: Frenette R. and Friesen R. (1994) *Tetrahedron Lett.* 35, 9177). Bromination of II with NBS (for an example of bromination of thiophene with NBS, see: Kellogg R. K. et al (1968) *J. Org. Chem.* 33, 1902) in THF in the presence of water afforded the corresponding bromothiophene which was then subjected to another Suzuki reaction with arylboronic acids to furnish resins III. Reacting III with $Br_2PPh_3$ gave the corresponding bromo resin IV (see: (1964) *J. Am. Chem. Soc.* 86, 964); IV were then treated with nucleophiles (thiols, amines, phenols, and boronic acids, etc.) to give resins V which were cleaved with TFA to furnish the corresponding carboxylic acids Ia (Wang resin) or with MeMgBr to yield the corresponding dimethylcarbinols Ib.

Method 1: General Method for Solid Phase Synthesis

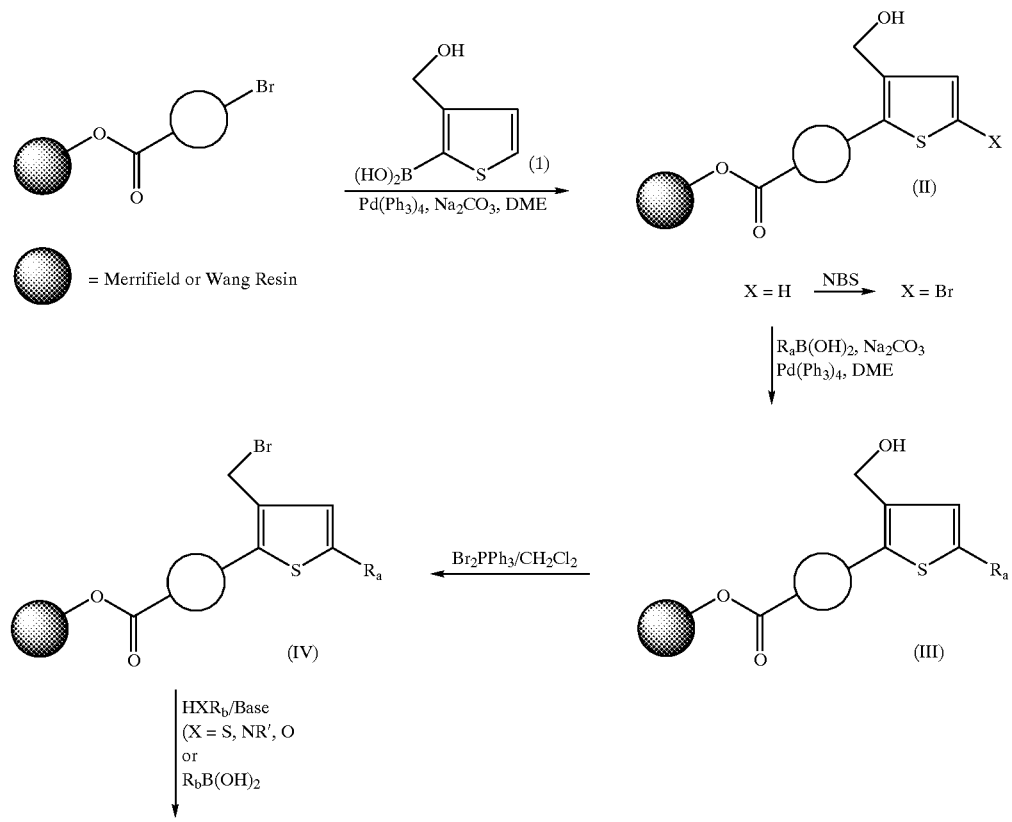

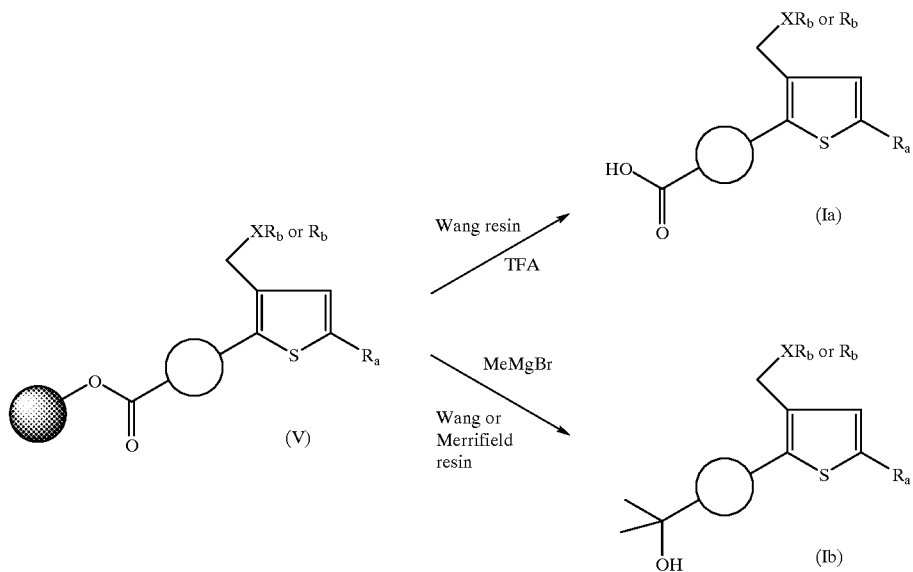

Method 2

The procedures for solution synthesis were similar to that described for the solid phase synthesis except that every intermediate was purified and characterized. Additionally, the Heck coupling reactions (from intermediates VI to VII) were performed according to known literature procedures (for a review of the Heck reaction, see: de Meijere A. and Meyer F. E. (1994) *Angew. Chem. Int. Ed. Engl.* 33, 2379). Intermediates VII were reacted either with $Br_2PPh_3$ to give the corresponding bromides or with MsCl and diisopropylethylamine in THF to afford the corresponding mesylates which were then reacted with nucleophiles to furnish products Ic. alternatively, VII were reacted with compounds bearing an acidic OH group under the Mitsunobo reaction conditions (for a review, see: Hughes D. L. (1996) *Organic Preparations and Procedures Int.* 28, 127–164) to yield products ID.

Method 2: General Method for Solution Synthesis

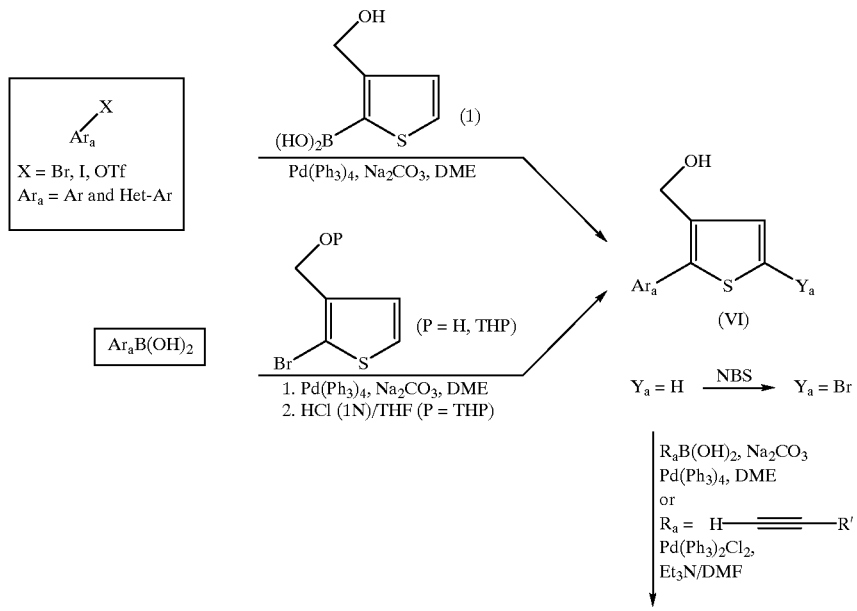

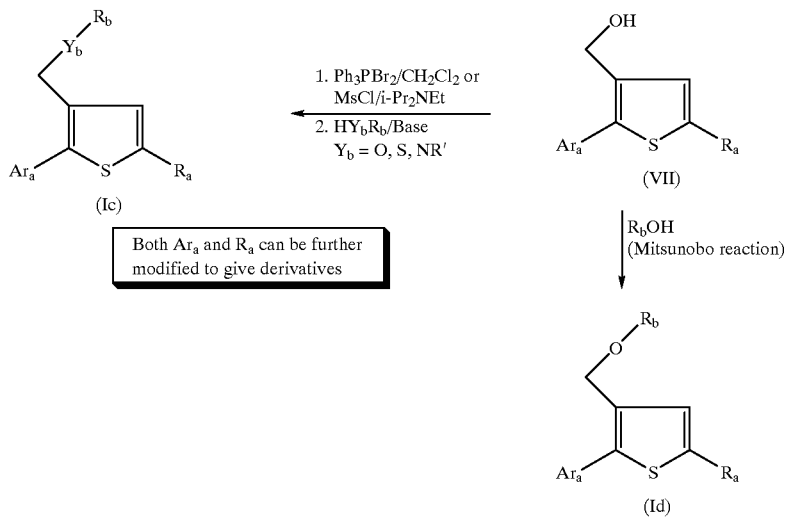

The invention will now be illustrated by the following non-limiting examples in which, unless stated otherwise, all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The example numbers below correspond to the example numbers (1–117) described above. Any examples listed above that are not mentioned or described below can be made by the combination of literature described methods and/or methods disclosed herein.

The following abbreviations have the indicated meanings:
Ac=acetyl
Bn=benzyl
BSA bovine serum albumin
cAMP cyclic adenosine-3',5'-monophosphate
DBU 1,8-diazabicyclo[5.4.0]undec-7-ene
DIBAL=diisobutylaluminum hydride
DMAP=4-(dimethylamino)pyridine
DMF=N,N-dimethylformamide
Et$_3$N=triethylamine
GST=glutathione transferase
LDA=lithium diisopropylamide
m-CPBA=metachloroperbenzoic acid
MMPP=monoperoxyphtalic acid
MPPM=monoperoxyphthalic acid, magnesium salt 6H$_2$O
Ms=methanesulfonyl=mesyl=SO$_2$Me
MsO=methanesulfonate=mesylate
NSAID=non-steroidal anti-inflammatory drug
o-Tol=ortho-tolyl
OXONE®=2KHSO$_5$.KHSO$_4$.K$_2$SO$_4$
PBS=phosphate buffer saline
PCC=pyridinium chlorochromate
PDC=pyridinium dichromate
PDE=phosphodiesterase
Ph=phenyl
Phe=benzenediyl
PMB=para-methoxybenzyl
Pye=pyridinediyl
r.t.=room temperature
rac.=racemic
SAM=aminosulfonyl or sulfonamide or SO$_2$NH$_2$
SPA=scintillation proximity assay
TBAF=tetra-n-butylammonium fluoride
Th=2- or 3-thienyl
TFA=trifluoroacetic acid
TFAA=trifluoroacetic acid anhydride
THF=tetrahydrofuran
Thi=thiophenediyl
TLC=thin layer chromatography
TMS-CN=trimethylsilyl cyanide
TNF=tumor necrosis factor
Tz=1H (or 2H)-tetrazol-5-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl c-Bu=cyclobutyl
c-Pen=cyclopentyl
c-Hex=cyclohexyl

| Dose Abbreviations | | |
|---|---|---|
| bid = | bis in die = | twice daily |
| qid = | quater in die = | four times a day |
| tid = | ter in die = | three times a day |

The following schemes illustrate intermediates to which reference is made in the description of the Examples.

Scheme 1:
Resin Intermediates

Resin A

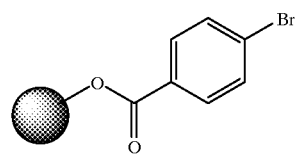

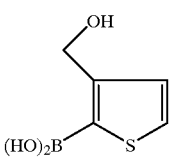 = Wang Resin

Resin B

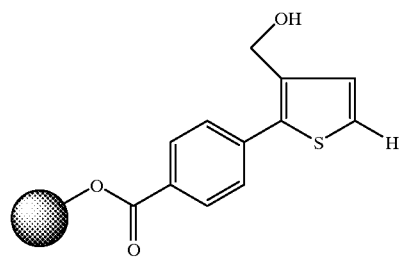

Resin C

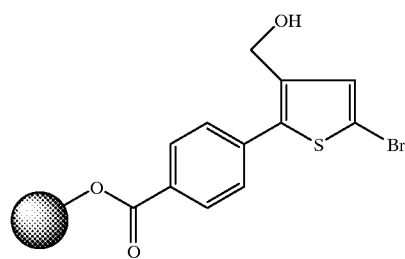

Resin D

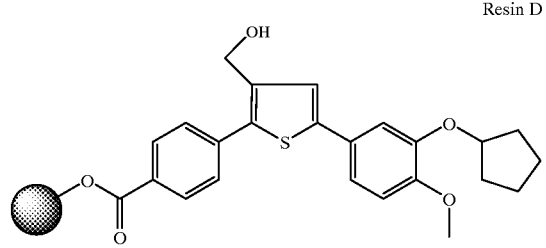

Resin E

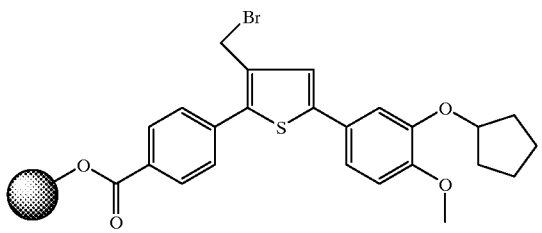

Resin F

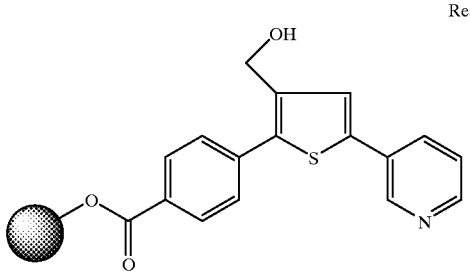

Resin G

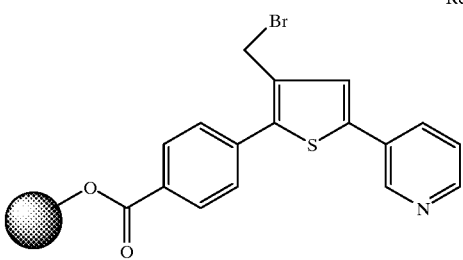

Scheme 2:
Chemical Intermediates

1

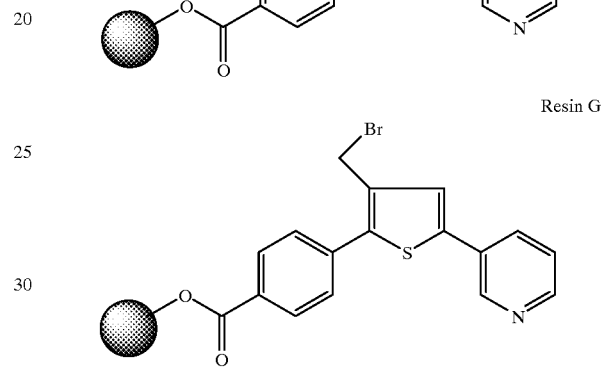

2

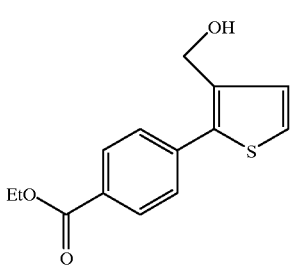

3

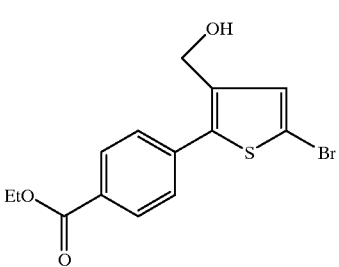

-continued
4
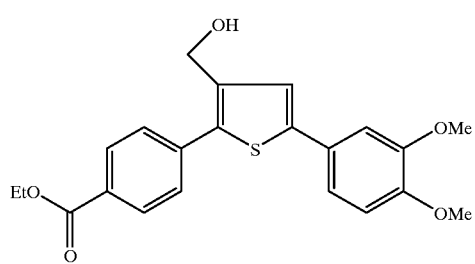
5
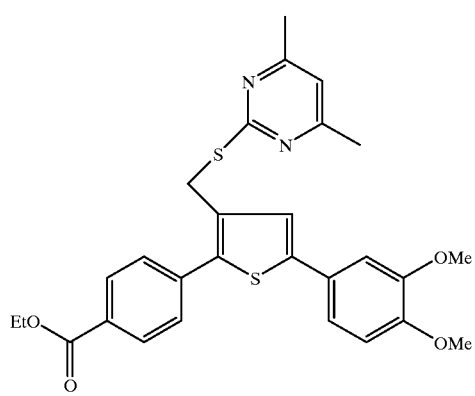
6
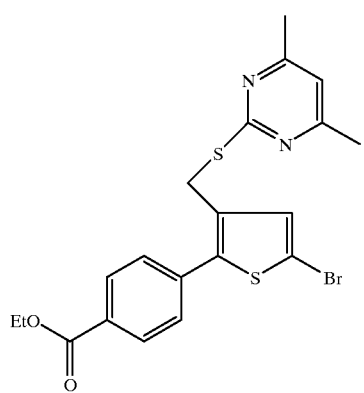
7
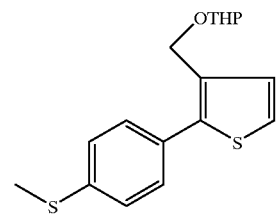
8
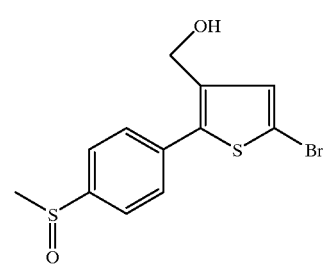
-continued
9
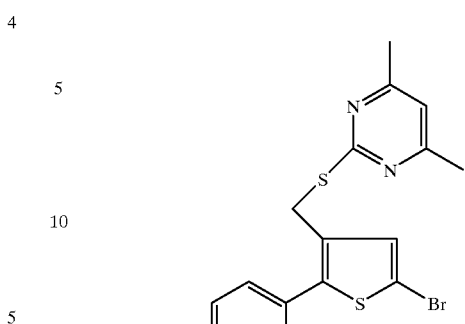
10
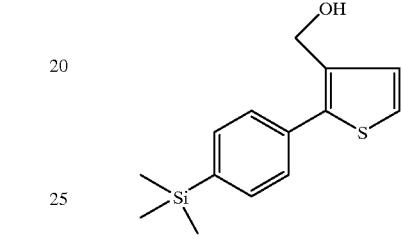
11
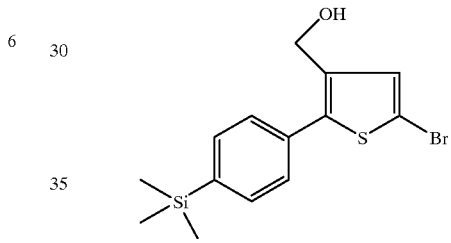
12
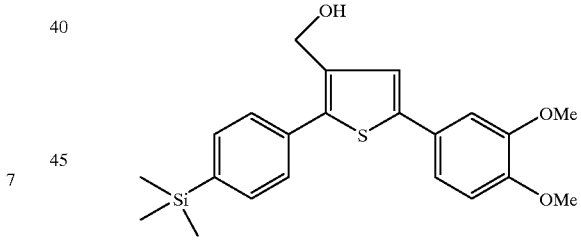
13
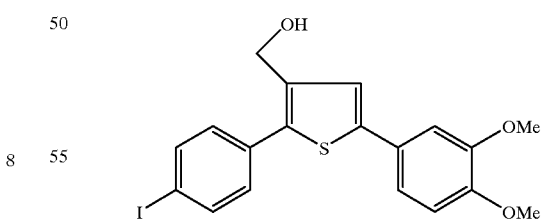

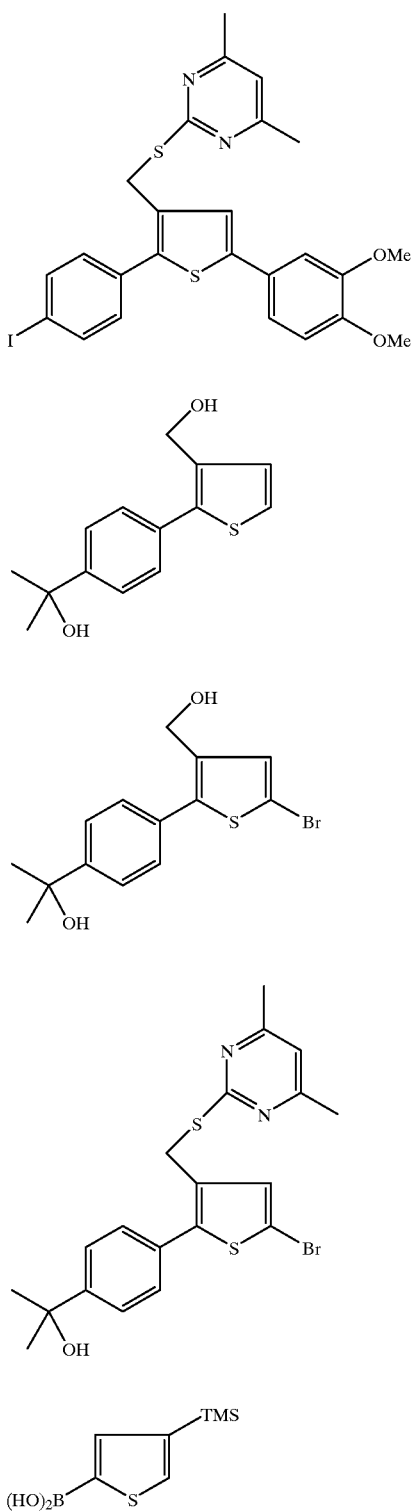

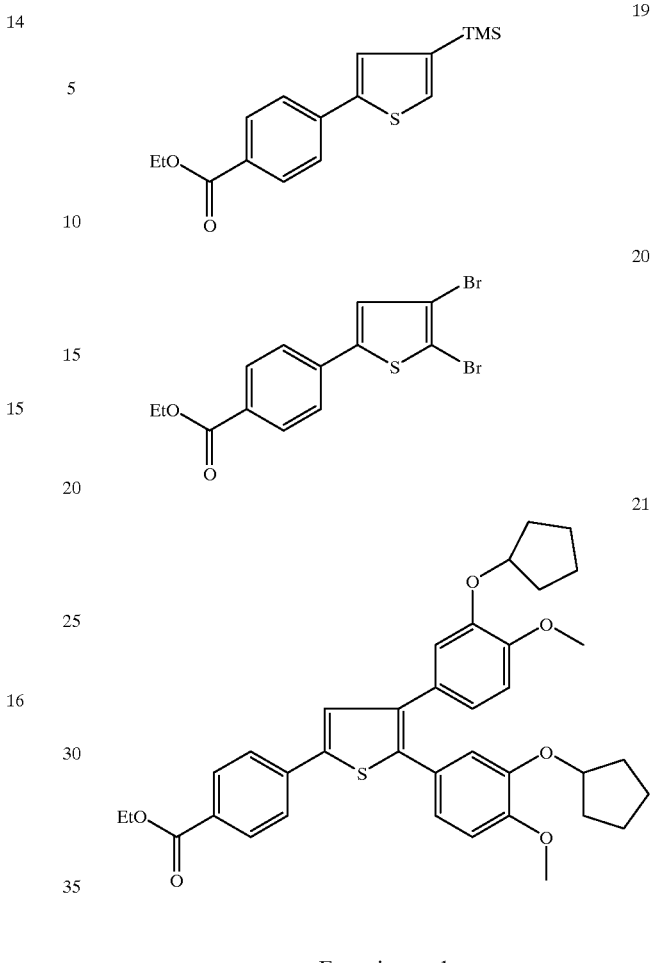

Experimental

Example 2

3-(4,6-Dimethylpyrimidin-2-yl)thiomethyl-2-[4-(1-hydroxy-1-methylethyl)phenyl]-5-[2-(4-methylpiperazin-1-yl)pyridin-5-yl]thiophene A mixture of bromide 16 (257 mg), lithium 2-(4-N-methylpiperazino)pyridine-5-trimethylboronate salt (657 mg), Pd(PPh$_3$)$_4$ (20 mg) in DME/H$_2$O was heated to 80 C. overnight and worked up as usual. The crude product was purified by flash chromatography. Eluting with 5% MeOH in CH$_2$Cl$_2$ afforded the title compound (80 mg) as a white solid. $^1$H NMR: see Table 1.

Examples 9, 17, 20 and 24 were prepared similarly.

Example 3

3-(4,6-Dimethylpyrimidin-2-yl)thiomethyl-2-[4-(1-hydroxy-1-methylethyl)phenyl]-5-[3-(4-pyridyloxy)phenyl]thiophene A mixture of Example 26 (48 mg), 4-chloropyridine (31 mg) and K$_2$CO$_3$ (45 mg) in DMAC was heated to reflux for 3 h and cooled to rt. The mixture was diluted with water and extracted with ethyl acetate. The extract was washed with brine dried over $MgSO_4$, filtered and concentrated. The residue was purified by flash chromatography. Eluting with 4:1 ethyl acetate in hexanes afforded the title compound (36 mg, 64% yield) as a white solid. $^1H$ NMR: see Table 1.

Examples 4 and 10 were prepared similarly.

Example 8

2-(4-Carboxyphenyl)-5-(-3,4-dimethoxyphenyl)-3-(4,6-dimethylpyrimidin-2-yl)thiomethylthiophene

Step 1. Preparation of Intermediate 2: To a solution of ethyl 4-bromobenzoate (2.29 g, 10 mmol) in DME (40 mL) was added boronic acid 1 (2.37 g, 15 mmol), $Pd(PPh_3)_4$ (346 mg, 0.3 mmol) and $Na_2CO_3$ (2M, 7.5 mL) and the mixture was deoxygenated under a stream of $N_2$ for 5 min and then heated to 80° C. for 50 min. After cooling to rt, the mixture was diluted with $H_2O$ and extracted with ethyl acetate (3×50 mL). The extracts were combined, washed with water, brine, dried over $Mg_2SO_4$ and then filtered through a sintered funnel. The filtrate was concentrated in vacuo and the residue purified by flash chromatography (eluting with 40% ethyl acetate in hexanes) to afford intermediate 2 (2.7 g, 100%) a yellow powder. $^1H$ NMR (400 MHz, $CDCl_3$): $\delta 8.07$ (d, 2H), 7.56 (d, 2H), 7.33 (d, 1H), 7.20 (d, 1H), 4.69 (d, 2H), 4.28 (q, 2H), 1.62 (t, 1H, OH), 1.40 (t, 3H). This procedure will be referred to as the standard Suzuki coupling reaction conditions in solution.

Step 2. Bromination to Intermediate 3: To a solution of intermediate 2 (2.7 g, 10 mmol) in THF (50 mL) at 0° C. was added NBS (3.56 g, 20 mmol) and water (5 mL) and the mixture was stirred at 0° C. for 30 min and quenched with excess 5% $Na_2S_2O_3$ aqueous solution. The mixture was then extracted with ethyl acetate (3×50 mL) and the extracts combined, washed with water, brine, dried over $Mg_2SO_4$ and filtered. The filtrate was concentrated in vacuo and the residue was purified by flash chromatography (eluting with 40% ethyl acetate in hexanes) to afford 3.24 g (95% yield) of bromide 3 as a white crystalline solid after recrystallization from ether and hexanes. $^1H$ NMR (400 MHz, $CDCl_3$): $\delta 8.06$ (d, 2H), 7.48 (d, 2H), 7.16 (s, 1H), 4.61 (d, 2H), 4.38 (q, 2H), 1.75 (t, 1H, OH), 1.39 (t, 3H).

Step 3. Preparation of Intermediate 4: To a solution of bromide 3 (610 mg, 1.79 mmol) in DME (8 mL) was added 3,4-dimethoxyphenylboronic acid (391 mg, 2.15 mmol) (see: Yokoe, I. et al, (1989) *Chem. Pharm. Bull.* 37, 529), $Pd(PPh_3)_4$ (62 mg, 0.054 mmol) and $Na_2CO_3$ (1 mL, 2M) and the mixture was deoxygenated under a stream of nitrogen for 5 min, heated to reflux for 4 h, and then cooled to rt and diluted with water. The mixture was then extracted with ethyl acetate (3×) and the extracts combined, washed with water, brine, dried over $MgSO_4$, filtered and concentrated to give the crude product which was purified by flash chromatography (50% ethyl acetate in hexanes) to yield compound 4 (0.65 mg, 91% yield) as a yellow solid after recrystallization from ethyl acetate and hexanes. $^1H$ NMR (400 MHz, Acetone-$d_6$): $\delta 8.08$ (d, 2H), 7.73 (d, 2H), 7.48 (s, 1H), 7.25 (d, 1H), 7.21 (dd, 2H), 7.00 (d, 1H), 4.65 (d, 2H), 4.38 (t, 1H, OH), 4.37 (q, 2H), 3.90 (s, 3H), 3.85 (s, 3H), 1.38 (t, 3H).

Step 4. Preparation of Intermediate 5: To a solution of compound 4 (461 mg, 1.16 mmol) in $CH_2Cl_2$ (6 mL) at 0° C. was added $Br_2PPh_3$ (586 mg, 1.39 mmol) and the solution was allowed to warm to rt and stirred for 30 min under $N_2$. Then to the solution was added 4,6-dimethyl-2-mercaptopyrimidine (325 mg, 2.32 mmol) and diisopropylethylamine (0.8 mL) and the resultant solution was stirred at rt for 1 h and concentrated. The residue was purified by flash chromatography (40–50% ethyl acetate in hexanes) to afford compound 5 (663 mg, 91% yield) as a light yellow solid. $^1H$ NMR (400 MHz, acetone-$d_6$): $\delta 8.11$ (d, 2H), 7.76 (d, 2H), 7.53 (s, 1H), 7.25 (d, 1H), 7.20 (dd, 1H), 6.99 (d, 1H), 6.90 (s, 1H), 4.50 (s, 2H), 4.37 (q, 2H), 3.90 (s, 3H), 3.84 (s, 3H), 2.33 (s, 6H), 1.38 (t, 3H).

Step 5. Hydrolysis: A mixture of compound 5 (213 mg, 0.41 mmol) and LiOH (1.23 mL, 1M) in dioxane (5 mL) was heated to 80° C. for 2 h and cooled to rt, diluted with water and acetic acid and then extracted with ethyl acetate. The extract was washed with water, brine, dried over $MgSO_4$, filtered and concentrated. The crude was crystallized from ethyl acetate and hexanes to give the title compound as a white powdery solid (189 mg, 94% yield). MP 238.8° C.

Alternative Method

Step 1. Preparation of Intermediate 6: To a solution of bromide 3 (111 mg, 0.36 mmol) dissolved in $CH_2Cl_2$ (2 mL) was added $Br_2PPh_3$ (227 mg, 0.54 mmol) at 0° C. and the mixture was stirred at 0° C. under $N_2$ for 1 h. To the solution was; added a solution of 4,6-dimethyl-2-mercaptopyrimidine in DMF (1M, 0.54 mL) and diisopropylethylamine (93 uL) and the mixture stirred at rt for 30 min, diluted with water and extracted with ethyl acetate. The extract was washed with brine, dried over $MgSO_4$, filtered and concentrated. The residue was purified by flash chromatograph (30% ethyl acetate in hexanes) to give compound 6. $^1H$ NMR (400 MHz, acetone-$d_6$): $\delta 8.11$ ((d, 2H), 7.70 (d, 2H), 7.33 (s, 1H), 6.89 (s, 1H), 4.45 (s, 2H), 4.39 (q, 2H), 2.31 (s, 6H), 1.36 (t, 3H).

Step 2. Preparation of Intermediate 5: Bromide 6 from above was reacted with 3,4-dimethoxyphenylboronic acid in a similar manner to that used to prepare compound 4, to yield compound 5.

Examples 27, 32, 34, 39, 42, 44, 49, 52, 54, 58, 59, 63, 73, 84, and 101 were prepared using technology similar to that described above.

Example 13

5-(3,4-Dimethoxyphenyl)-3-(4,6-dimethylpyrimidin-2-yl)thiomethyl-2-[4-(1-hydroxy-1-methylethyl)phenyl]thiophene

To a solution of compound 5 (1.3 g) in THF (10 mL) was added MeMgBr (10.3 mL, 1.4M in THF/Toluene) at 0° C. and the solution was stirred at rt for 30 min and quenched with $NH_4Cl$ (sat'd aq) and extracted with ethyl acetate (2×50 mL). The extracts were combined, washed with brine, dried over $MgSO_4$ and filtered. Concentration of the filtrate gave a yellow residue which was purified by flash chromatography, eluting with 60% ethyl acetate in hexanes. The title compound was crystallized from $CH_2Cl_2$ and hexanes as a light yellow flaky solid (1.2 g, 95% yield). M.P.: 71.5° C.; $^1H$ NMR (400 MHz, acetone-$d_6$): $\delta 7.64$ (d, 2H), 7.55 (d, 2H), 0.47 (s, 1H), 7.22 (d, 1H), 7.18 (dd, 1H), 6.97 (d, 1H), 6.88 (s, 1H), 4.46 (s, 2H), 4.09 (s, 1H, OH), 3.88 (s, 3H), 3.83 (s, 3H), 2.33 (s, 6H), 1.55 (s, 6H).

Examples 38, 74, and 76 were prepared in a similar manner.

Example 18

5-(3,4-Dimethoxyphenyl)-3-(4,6-dimethylpyrimidin-2-yl)thiomethyl-2-[4-(1-hydroxycyclobutyl)phenyl]thiophene

Step 1. One pot preparation of 4-trimethylsilylphenylboronic acid (see: Kaufmann et al, (1987) *Chem. Ber.* 120, 901): To a solution of p-dibromobenzene (11.8 g, 50 mmol) in THF (250 mL) at −78° C. was added n-BuLi (20 mL, 2.5M: in hexanes) over 2 min and the mixture was stirred at −78° C. for 2 min.

TMSCl (6.3 mL, 50 mmol) was added in one portion and the resultant mixture was stirred at −78° C. for 10 min. n-BuLi (20 mL) was added again over 2 min and stirring was continued for 10 min at −78° C. followed by the addition of triisopropylborate (13 mL, 55 mmol) quickly and the mixture was stirred at −78° C. for 30 min, allowed to warm to rt, quenched with water, AcOH (2.5 eq) and then extracted with ethyl acetate (3×10 mL). The extracts were combined, washed with water and concentrated to afford 9 g of the title boronic acid as a white solid which was further recrystallized from hexanes to give a grey white powder. $^1$H NMR (400 MHz, acetone-$d_6$): δ7.85 (d, 2H), 7.53 (d, 2H), 7.11 [s, 2H, B(OH)$_2$], 0.25 (s, 9H).

Step 2. Preparation of Intermediate 10: The boronic acid (4.96 g, 25.5 mmol) from Step 1 was reacted with 2-bromo-3-hydroxymethylthiophene (4.7 g, 24.3 mmol) (prepared from 3-thiophenemethanol with NBS in THF) under the standard Suzuki coupling conditions to yield intermediate 10 in 73% yield. $^1$H NMR (400 MHz, acetone-$d_6$): δ7.62 (d, 2H), 7.54 (d, 2H), 7.39 (d, 1H), 7.21 (d, 1H), 4.62 (d, 2H), 4.17 (t, 1H, OH), 0.29 (s, 9H).

Step 3. Preparation of Intermediate 11: Compound 10 (4.6 g, 17.5 mmol) in THF (80 mL) was treated with NBS (6.25 g) at rt for 2 h and quenched with 10% Na$_2$S$_2$O$_3$ and then extracted with ethyl acetate. The extract was washed with water, brine, dried over MgSO$_4$, filtered and concentrated. The residue was purified by flash chromatography (eluting with 20% ethyl acetate in hexanes) to furnish 5.42 g (90% yield) of bromide 11. $^1$H NMR (400 MHz, acetone-$d_6$): δ7.62 (d, 2H), 7.49 (d, 2H), 7.23 (s, 1H), 4.57 (d, 2H), 4.31 (t, 1H, OH), 0.29 (s, 9H).

Step 4. Preparation of Intermediate 12: Bromide 11 (2 g, 5.86 mmol) was reacted with 3,4-dimethoxyphenylboronic acid (1.28 g, 7 mmol) under the standard Suzuki coupling reaction conditions to afford intermediate 12 (2.2 g, 94% yield) as a white solid. $^1$H NMR (400 MHz, acetone-$d_6$): δ7.63 (d, 2H), 7.57 (d, 2H), 7.44 (s, 1H), 7.25 (d, 1H), 7.20 (dd, 1H), 6.99 (d, 1H), 4.63 (d, 2H), 4.23 (t, 1H, OH), 3.90 (s, 3H), 3.84 (s, 3H), 0.30 (s, 9H).

Step 5. Preparation of Intermediate 13: Compound 12 (1.41 g, 3.54 mmol) was treated with a solution of ICl (8.85 mL, 1M in CH$_2$Cl$_2$) at rt for 1 h and quenched with 10% Na$_2$S$_2$O$_3$. The mixture was extracted with CH$_2$Cl$_2$ and the extract was concentrated. The residue was purified by flash chromatography (40% ethyl acetate, 10% CH$_2$Cl$_2$ in hexanes) to give iodide 13 (1.3 g, 81% yield) as a light brown solid. $^1$H NMR (400 MHz, acetone-$d_6$): δ7.83 (d, 2H), 7.43 (s, 1H), 7.41 (d, 2H), 7.24 (d, 1H), 7.20 (dd, 1 h), 6.99 (d, 1H), 4.59 (d, 2H), 4.32 (t, 1H, OH), 3.89 (s, 3H), 3.83 (s, 3H).

Step 6. Preparation of Intermediate 14: To a solution of iodide 13 (1 g, 2.21 mmol) in CH$_2$Cl$_2$ was added Br$_2$PPh$_3$ (1.12 g, 2.65 mmol) and the mixture stirred at rt for 30 min. 4,6-Dimethyl-2-mercaptopyrimidine (619 mg, 4.42 mmol) and diisopropylethylamine (1.54 mL) were introduced and the mixture was stirred at rt for 1 h, concentrated and the residue purified by flash chromatography (40% ethyl acetate in hexanes) to give compound 14 (1.28 g, 100% yield) as a light yellow solid. $^1$H NMR (400 MHz, acetone-$d_6$): δ7.86 (d, 2H), 7.49 (s, 1H), 7.42 (d, 2H), 7.23 (d, 1H), 7.18 (dd, 1H), 6.98 (d, 1H), 6.90 (s, 1H), 4.45 (s, 2H), 3.88 (s, 3H), 3.83 (s, 3H), 2.33 (s, 6H).

Step 7. To a solution of iodide 14 (68 mg) and cyclobutanone (20 μL) in ether (2 mL) and THF (2 mL) cooled to −100° C. was added n-BuLi (0.11 mL) and the mixture was allowed to warm to −70° C., quenched with water and extracted with ethyl acetate. The extract was washed with brine, dried over MgSO$_4$, filtered, concentrated and the crude was purified by flash chromatography (2:1 hexanes/ethyl acetate) to yield the title compound (52 mg, 85% yield) as a white solid. $^1$H NMR: see Table 1.

Examples 25, 33, and 61 were prepared similarly.

Example 21

5-(3,4-Dimethoxyphenyl)-3-(4,6-dimethylpyrimidin-2-yl)thiomethyl-2-(4-methylthiophenyl)thiophene Step 1. Preparation of Intermediate 7: A mixture of thioanisolyl-4-boronic acid (2.2 g, 13 mmol) (see: Santucci et al, (1958) *J. Am. Chem. Soc.* 80, 193), 2-bromo-3-hydroxymethylthiophene THP ether (3 g, 10.83 nmol), Pd(PPh$_3$)$_4$ (374 mg, 0.324 nmol) and Na$_2$CO$_3$ (6.5 mL, 2M) in DME (33 mL) was deoxygenated under a stream of N$_2$ and heated to reflux overnight and worked up as usual. The crude product was purified by flash chromatography (10% ethyl acetate in hexanes) to afford 3.26 g of coupling product 7. $^1$H NMR (400 MHz, acetone-$d_6$) δ7.49 (d, 2H), 7.40 (d, 1H), 7.35 (d, 2H), 7.17 (d, 1H), 4.70 (t, 1H), 4.69 (d, 1H), 4.46 (d, 1H), 3.81 (m, 1H), 3.48 (m, 1H), 2.53 (s, 3H), 1.90–1.40 (m, 6H).

Step 2. Preparation of Intermediate 8: The product from Step 1 was dissolved in 50 mL of THF/1N HCl (4/1) and heated to reflux for 3 h and cooled to rt. To the mixture was then added NBS (4.53 g) and the resultant solution stirred at rt for 2 h and quenched with 5% Na$_2$S$_2$O$_3$ and then extracted with ethyl acetate (3×50 mL). The extracts were combined, washed with water, brine, dried over MgSO$_4$, filtered and concentrated. The crude was purified by flash chromatography (5% ethanol in ethyl acetate) to yield 1.8 g of sulfoxide 8. $^1$H NMR (acetone-$d_6$, 400 MHz): δ7.78 (d, 2H), 7.71 (d, 2H), 7.28 (s, 1H), 4.59 (d, 2H), 4.43 (bt, 1H, OH), 2.90 (s, 3H). Alternatively, the same compound was prepared from the reaction of boronic acid 1 and 4-bromothioanisole under the Suzuki coupling reaction conditions and the resultant product brominated in a similar manner as described.

Step 3. Preparation of Intermediate 9: To a solution of sulfoxide 8 (1.8 g, 6 mmol) in CH$_2$Cl$_2$ (40 mL) was added Br$_2$PPh$_3$ (5.08 g, 12 mmol) at rt and the mixture stirred at rt for 1 h. To the mixture was then added 4,6-dimethyl-2-mercaptopyrimidine (2.52 g, 18 mmol) and diisopropylethylamine (5.2 mL, 30 mmol) and the mixture stirred at rt for 1 h and concentrated. The residue was purified by flash chromatography to yield compound 9 as a white solid (2.3 g, 88% yield). $^1$H NMR (400 MHz, acetone-$d_6$): δ7.48 (d, 2H), 7.37 (d, 2H), 7.27 (s, 1H), 6.89 (s, 1H), 4.40 (s, 2H), 2.54 (s, 3H0, 2.33 (s, 6H).

Step 4. A mixture of 9 (700 mg, 1.6 mmol), 3,4-dimethoxyphenylboronic acid (350 mg, 1.92 mmol), Pd(PPh$_3$)$_4$ (55 mg, 0.048 mmol) and Na$_2$CO$_3$ (1 mL, 2M) in DME (5 mL) was heated to reflux for 2 h and worked up as usual. The crude product was purified by flash chromatography (40% ethyl acetate in hexanes) to yield the title compound (711 mg, 90% yield) as a yellowish solid after crystallization from CH$_2$Cl$_2$/hexanes. $^1$H NMR: see Table 1.

Examples 4, 7, 15, 24, and 28 were prepared similarly by reacting intermediate 9 with the appropriate boronic acids and further modifications.

Example 26

3-(4,6-Dimethylpyrimidin-2-yl)thiomethyl-2-[4-(1-hydroxy-1-methylethyl)phenyl]-5-(3-hydroxyphenyl)thiophene Step 1. Preparation of Intermediate 15: To a solution of compound 2 (4 g) in THF (80 mL) was added MeMgBr (51 mL, 3M in THF) in THF (80 mL) at 0° C. under N$_2$ and the resulting mixture was stirred at that temperature for 1 h, quenched with 1N HCl and extracted with ethyl acetate. The crude was purified by flash chromatography (2:1 hexanes/ ethyl acetate) to give 3 g (79%) of product 15. $^1$H NMR (400 MHz, acetone-d$_6$): δ7.60 (d, 2H), 7.49 (d, 2H), 7.36 (d, 1H), 7.20 (d, 1H), 4.61 (d, 2H), 4.15 (t, 1H, OH), 4.05 (s, 1H, OH), 1.54 (s, 6H).

Step 2. Preparation of Intermediate 16: Compound 15 (3.0 g) was dissolved in THF (100 mL) and cooled to 0° C. To the solution was added NBS (4.3 g) and H$_2$O (1 mL) and the mixture stirred at 0° C. for 1 h, quenched with Na$_2$S$_2$O$_3$ and NaHCO$_3$ and extracted with ethyl acetate. The crude product was purified by flash chromatography (2:1 hexanes/ethyl acetate) to yield bromide 16. $^1$H NMR (400 MHz, acetone-d$_6$): δ7.62 (d, 2H), 7.44 (d, 2H), 7.20 (s, 1H), 4.58 (d, 2H), 4.30 (t, 1H, OH), 4.10 (s, 1H, OH), 1.55 (s, 6H).

Step 3. Preparation of Intermediate 17: To a solution of bromide 16 (2.6 g) in THF (10 mL) and CH$_2$Cl$_2$ (10 mL) at 0° C. was added MsCl (0.54 mL) and diisopropylethylamine (1.33 mL) and the mixture was stirred at 0° C. for 2 h. 4,6-Dimethyl-2-mercaptopyrimidine (1.36 g) was added followed by diisopropylethylamine (3.63 mL) and the mixture was stirred for an additional 15 min at 0° C. and then at rt for 20 min. Concentration in vacuo afforded the crude product which was purified by flash chromatography (2:1 hexanes/ethyl acetate). Compound 17 (2.8 g, 82% yield) thus obtained exists as a white solid. $^1$H NMR (300 MHz, acetone-d$_6$): δ7.64 (d, 2H), 7.48 (d, 2H), 7.26 (s, 1H), 6.86 (s, 1H), 4.41 (s, 2H), 4.10 (s, 1H, OH), 2.31 (s, 6H), 1.54 (s, 6H).

Step 4. Example 26: A mixture of the bromide 17 (983 mg), 3-allyloxyphenylboronic acid (623 mg, prepared by reacting 3-bromophenol allyl ether with n-BuLi and triisopropylborate), Pd(PPh$_3$)$_4$ (81 mg) and Na$_2$CO, (2.3 mL, 2M) in DME was deoxygenated under nitrogen and then heated to reflux overnight. The mixture was cooled to rt and worked up as usual. To the crude product dissolved in THF (10 mL) was added Pd(PPh$_3$)$_4$ (85 mg) and pyrrolidine and the mixture was degassed under nitrogen and heated to reflux for 1 h, cooled to rt, acidified with 1N HCl and extracted with ethyl acetate. The crude product thus obtained was purified by flash chromatography (1:1 hexanes/ethyl acetate) to yield the title compound as a white solid. $^1$H NMR: see Table 1.

Example 35

2-(4-Carboxyphenyl)-5-(3-cyclopentyloxy-4-methoxyphenyl)-3-(4,6-dimethylpyrimidin-2-yl)thiomethylthiophene Step 1. Preparation of 3-hydroxymethylthiophene-2-boronic acid (1): To a solution of 2-(dihydroxyboranyl)thiophene-3-carboxaldehyde (prepared from thiophene-3-carboxaldehyde dimethyl acetal by a modified literature procedure, see: Gronowitz, S. et al, (1967) *Acta Chem. Scand.* 21, 2151) (3.34 g, 0.214 mol) in ethanol (20 mL) at 0° C. under nitrogen was added NaBH$_4$ (0.81 g, 0.21 mol) in portions in 10 min. After stirring for 30 min at 0° C., the mixture was quenched with water and NH$_4$Cl (sat'd aq.). The pH was adjusted with 1N HCl ~5–6 and the mixture was extracted with ethyl acetate (5×30 mL). Evaporation of the extracts afforded the title compound as a white powdery solid (3.5 g, 100%): $^1$H NMR (400 MHz, Acetone-d$_6$+1 drop D$_2$O): δ7.52 (d, 1H), 7.03 (d, 1H), 4.78 (s, 2H). The product was kept under nitrogen at -20° C. to avoid decomposition.

Step 2. Preparation of Resin B: Reaction of 1 with polymer bound (Wang resin) 4-bromobenzoate (resin A): To a suspension of the resin (6.16 g, 5.3 mmol, 0.86 mmol/g loading) in DME (30 mL) was added boronic acid 1 (1.67 g, 10.6 mmol), Pd(PPh$_3$)$_4$ (184 mg, 0.16 mmol) and Na$_2$CO$_3$ (2M solution, 5.3 mL) and the mixture was deoxygenated under a stream of nitrogen for 5 min. under gentle stirring and then heated to 85° C. under nitrogen overnight. The mixture was filtered when hot and the resin washed sequentially with DMF (3×), DMF/H$_2$O (3×), DMF (2×), THF (2×) and then MeOH (3×) and dried under nitrogen flow for 48 h to yield resin B.

Step 3. Preparation of Resin C: Resin B was suspended in 60 mL of THF and cooled to 0° C. NBS (1.9 g, 10.6 mmol) was added followed by 1 mL H$_2$O and the mixture was allowed to warm to rt for 11/2 h and filtered. The resin was then washed with THF (3×), DMF (3×), THF (2×) and MeOH (3×) and dried under nitrogen and then under vacuum to give resin C.

Step 4. Preparation of 3-Cyclopentyloxy-4-methoxyphenylboronic acid: To a solution of 4-bromo-2-cyclopentyloxy-1-methoxybenzene (3.4 g, 12.5 mmol) (see: Meyer, A. I. et al, (1993) *J. Org. Chem.* 58, 36) in THF (60 mL) at -78° C. was added n-BuLi (5.2 mL, 2.4M in hexanes) over 2 min and the resultant solution stirred at -78° C. for 5 min. Triisopropylborate (3 mL) was added in one portion and the mixture was stirred at -78° C. for 20 min, allowed to warm to rt, and quenched with water and acetic acid (0.75 mL). Concentration in vacuo afforded a white solid which was filtered. The white solid was washed twice with water and dried under reduced pressure to give the title compound (2.64 g, 89% yield) as a white powder. $^1$H NMR (400 MHz, acetone-d$_6$+1 drop D$_2$O): δ7.44–7.41 (m, 2H), 6.90 (d, 1H), 4.80 (m, 1H), 3.77 (s, 3H), 1.90–1.50 (m, 8H).

Step 5. Preparation of Resin D. General procedure for the Suzuki coupling reaction on solid support: A suspension o f resin C (2.76 g), 3-cyclopentyloxy-4-methoxyphenylboronic acid (1.56 g, 6.6 mmol), Pd(PPh$_3$)$_4$ (77 mg, 0.066 mmol) and Na$_2$CO$_3$ (2M, 3 mL) in DME (27 mL) was deoxygenated under a stream of nitrogen for 5 min and then heated to reflux for 7 h and poured into a 70 mL flitted polypropylene tube. The solvents were flushed out with a stream of nitrogen and the resin washed sequentially with DMF (3×) DMF/H$_2$O (3×), DMF (2×), THF (2×) and MeOH (3×) and then dried under nitrogen overnight to afford 2.9 g of resin D.

Step 6. Preparation of Resin E: Converting CH$_2$OH to CH$_2$Br: To a suspension of resin D (2.9 g) in dichloromethane (30 mL) under N$_2$ at 0° C. was added Br$_2$PPh$_3$ (1.5 g, 3.48 mmol) and the mixture was allowed to warm to rt with gentle stirring and then filtered. The residual resin was washed with CH$_2$Cl$_2$ (3×), THF (3×), ethyl acetate (2×) and ether (3×), and dried under reduced pressure to give resin E.

Step 7. Final product: To a suspension of resin E (50 mg) in DMF (0.5 mL) in a 5-mL fritted polypropylene tube equipped with a Teflon™ stopcock was added a solution of 4,6-dimethyl-2-mercaptopyrimidine in DMF(200 μL, 1M) and diisopropylethylamine (50 μL) and the mixture was shaken for 1 h at rt. The solvent was drained and the residue washed with DMF (3×), THF (3×), MeOH (3×) and CH$_2$Cl$_2$ (3×) and the resultant resin was then treated with 1 mL 20% TFA in CH$_2$Cl$_2$ (containing 5% dimethyl sulfide) for 30 min. The liquid was drained to a round bottom flask and the residual resin washed with CH$_2$Cl$_2$ (3×) and again drained to the flask. Evaporation of volatiles afforded the title compound as a yellow solid. $^1$H NMR: see Table 1.

Examples 27, 82, 83, 86, 94, 95, 96, 97, 100, 102, 103, 104, 108, 114, 115, and 116 were prepared similarly.

Examples 14, 40, 43, 48, 50, 78, 80, 81, 85, 87, 89, and 90 were synthesized from the corresponding polymer (Merrifield or Wang resins) bound bromides according to similar procedures as described for Example 35 except for the cleavage. The Cleavage were carried out using MeMgBr (1.4M in THF/toluene, 20 eq) in THF at room temperature for 2–12 h and filtered through fritted polypropylene reservoirs. The filtrates were quenched with NH$_4$Cl (saturated aq.) and extracted with ethyl acetate. The crude products were purified by preparative TLC.

Example 106

5-(4-Carboxyphenyl)-2,3-bis((3-cyclopentyloxy-4-methoxy)phenyl)thiophene

Step 1. Preparation of boronic acid 18: To a solution of 3-trimethylsilylthiophene (1.56 g) in THF (15 mL) at −78° C. was added a THF solution of LDA (pre-prepared from 1.68 mL of diisopropylamine and 4.6 mL 2.4M n-BuLi in THF) via a cannula and the resultant solution was stirred at −78° C. for 10 min, rt for 30 min and cooled to −78° C. again. Triisopropylborate (1.37 mL) was added and stirring was continued for 1 h at −78° C. and rt for 30 min. The mixture was then quenched with H$_2$O and partitioned between hexanes and H$_2$O. The aqueous phase was acidified with acetic acid to pH~5 and extracted with ethyl acetate (3×). The extracts were concentrated and the crude was recrystallized from acetone/H$_2$O to yield 18 (1.41 g) as a white powder. $^1$H NMR (400 MHz, acetone-d$_6$): δ7.79 (m, 2H), 7.25 (bs, 2H), 0.25 (s, 9H).

Step 2. Preparation of Intermediate 19: A solution of ethyl 4-bromobenzoate (460 mg), boronic acid 18 (500 mg), Pd(OAc)$_2$ (13.5 mg), PPh$_3$ (32 mg) in DMF (3 mL) and Et$_3$N (3 mL) was heated to 90° C. overnight and cooled to rt. The mixture was diluted with water and extracted with ether (3×). The extracts were combined, washed with water, brine, dried over MgSO$_4$ and concentrated. The residue was purified by flash chromatography (5% ethyl acetate in hexanes) to give compound 19 (584 mg) as a yellow oil. $^1$H NMR (400 MHz, CDCl$_3$): δ8.02 (d, 2H), 7.66 (d, 2H), 7.42 (d, 1H), 7.41 (d, 1H), 4.37 (q, 2H), 1.39 (t, 3H), 0.28 (s, 9H).

Step 3. Preparation of Intermediate 20: A solution of 19 (470 mg), NBS (550 mg) and AcOH (1 mL) in THF was heated to reflux for 2 h and cooled to rt. The mixture was treated with aqueous Na$_2$S$_2$O$_3$ and extracted with ethyl acetate. The extract was concentrated and the crude purified by flash chromatography to give compound 20. $^1$H NMR (CDCl$_3$, 400 MHz): δ8.05 (d, 2H), 7.53 (d, 2H), 7.18 (s, 1H), 4.36 (q, 2H), 1.40 (t, 3H).

Step 4. A mixture of 20 (303 mg), 3-cyclopentyloxy-4-methoxyphenylboronic acid (373 mg), Pd(PPh$_3$)$_4$ (27 mg) and Na$_2$CO$_3$(0.8 mL, 2M) in DME (7 mL) was deoxygenated under N$_2$ and heated to reflux for 5 h and worked up as usual. Purification of the crude by flash chromatography failed to give compound 21 in its pure form. As a result, the fraction containing 21 (180 mg) was dissolved in dioxane (1 mL) and H$_2$O (1 mL) containing LiOH monohydrate (46 mg) and the mixture was heated to 70° C. for 2 h and cooled to rt. The mixture was acidified with 1N HCl and then extracted with ethyl acetate. The crude product was purified by flash chromatography (60% ethyl acetate, 5% ethanol in hexanes) to afford the title compound. M.P.: see Table 1.

Example 110

3-(3-Cyclopentyloxy-4-methoxy)benzyl-2-[4-(1-hydroxy-1-methylethyl)phenyl]5-(3-pyridin-1-yl)thiophene Step 1. Preparation of Resin F: A suspension of resin C (4.3 g), lithium pyridine-3-trimethylboronate (1.81 g) (see: Fischer et al, (1974) *Recl. Trav. Chim. Pays-Bas* 93, 21) and Pd(PPh$_3$)$_4$ (199 mg) in DME (32 mL) and H$_2$O (4 mL) was deoxygenated under N$_2$ for 5 min and then heated to reflux overnight. The mixture was filtered and the residue washed with DMF (3×), DMF/H$_2$O (3×), THF (2×), CH$_2$Cl$_2$ (2×) and MeOH (3×) and dried under reduced pressure to yield resin F.

Step 2. Preparation of Resin G: To a suspension of resin F (4.3 g) in CH$_2$Cl$_2$ (30 mL) was added Br$_2$PPh$_3$ (2.18 g) and the suspension was stirred at rt for 1 h and filtered. The residue was washed with CH$_2$Cl$_2$ (3×), DMF (3×), THF (2×), ethyl acetate (2×) and ether (2×), and then dried under reduced pressure to afford resin G.

Step 3. A mixture of resin G (96 mg), 3-cyclopentyloxy-4-methoxyphenylboronic acid (54 mg), Pd(PPh$_3$)$_4$ (4.4 mg) and CsF (70 mg) was deoxygenated under N$_2$ for 5 min and heated to 80° C. for 2 h. The mixture was filtered when hot and the residue washed with DMF (3×), DMF/H$_2$O (3×), DMF, THF (2×) and MeOH (3×) and then dried under reduced pressure. To the dried resin suspended in THF (1 mL) was added MeMgBr (1 mL, 1.4M in THF/Toluene) and the mixture was stirred at rt for 2 h. The mixture was filtered and the residue washed twice with THF/H$_2$O (4:1). The filtrate and the washing solutions were combined, quenched with NH$_4$Cl (aq) and extracted with ethyl acetate (3×). The extracts were concentrated and the residue purified by preparative TLC to yield the title compound. $^1$H NMR: see Table 1.

Assays for Determining Biological Activity

Establishment of CHO-K1 Cell Lines Stably Expressing PDE IVa Enzyme

CHO-K1 cells stably expressing the prostacyclin receptor and grown under G418 selection as described previously (Y. Boie, et al, J. Biol. Chem.: 269, 12173–12178, 1994) were plated at a density of 1.75×10$^6$ cells/175 cm$^2$ in a T-175 flask (Gibco, Burlington, Vt.) containing alpha MEM media; 10% heat inactivated fetal bovine serum (FBS); 1% (v/v) penicillin/streptomycin; 25 mM Hepes, pH 7.4; and 500 µg/ml G418 (complete media). The cells were placed in an incubator for 24 hr at 37° C. and 5% CO$_2$. The cells were then washed with warmed sterile phosphate buffered saline (PBS) and incubated with 2 µg/ml DNA, and 9 µg /ml lipofectamine reagent in Opti-MEM for 7 hr. At 37° C. and 5% CO$_2$. The incubation solution was diluted 1:2 with Opti-MEM containing 20% FBS and incubated overnight. Following the overnight incubation, the media was replaced by complete media containing 500 µg/ml hygromycin B. Colonies were identified and grown in T-175 flasks for further characterization.

Measurement of Whole-Cell cAMP Content

CHO-K1 cells were plated at a density of 10$^6$ cells/175 cm$^2$ containing complete media with 500 µg/ml hygromycin. The flasks were maintained in an incubator at 37° C. with 5.0% CO$_2$ for 72 hr. The media was changed and the cells were allowed to grow overnight. The cells were washed and dissociated from the plate with PBS containing 0.5 mM EDTA. Cellular cAMP content was measured by centrifuging the cell suspension at 150 g×10 min. And resuspending the cells in a Hanks buffered salt solution at a density of 0.2×10$^6$ cells/ml. The cells were preincubated at room temperature for 15 min. and then incubated with 10 µM prostaglandin I$_2$ (PGI$_2$) and the indicated compound for an additional 10 min. Basal cAMP levels were determined by incubating the cells in 0.1% DMSO. The incubations were terminated by the addition of HCl (0.1 N final) and the cells measured for cAMP as described below.

Determinations of whole-cell cAMP content were performed by incubating 100 µl reconstituted rabbit anti-succinyl cAMP serum with 100 µl of the whole-cell reaction or known cAMP standard and 30 pmol of $^{125}$I-cAMP TME in a ScintiStrip™ well (300 µl final volume) at room temperature for 18 h. Total cpm (B$_o$) was determined in the absence of sample of cAMP standard. The reaction mixture was then aspirated out of the well, and the individual wells were counted in a Beckman LS 6000SC with the window open from 10–999 for 1 min. The data were expressed as % B/B$_o$=[(standard or sample cpm−non-specific cpm)/(B$_o$ cpm−non-specific cpm)]×100. Non-specific cpm were determined by incubating only the $^{125}$I-cAMP TME with assay buffer (50 nM acetate; pH 5.8) in the ScintiStrip™ well. All determinations were performed in triplicate.

The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the invention induced a concentration-dependent elevation of cAMP in neutrophils and/or eosinophils at concentrations of 0.1 nM to 1 μM.

Human Whole Blood Assay

Fresh blood was collected in heparinized tubes by venipuncture from healthy volunteers. These subjects had no apparent inflammatory conditions and had not taken any NSAIDs for at least 4 days prior to blood collection. Five hundred μL aliquots of human blood were initially pre-incubated at 37° C. with either 2 μL DMSO (vehicle) or 2 μL of a test compound at a final concentration of up to 100 μM. Fifteen min later, the blood was incubated with lipopolysaccharide (LPS) at 1 μg/ml (Sigma Chem, #L-2630 from E. coli, serotype 0111:B4; diluted in 0.1% w/v BSA/PBS) for 24 h at 37° C. At the end of the 24 h incubation, the blood was further incubated with an additional amount of LPS (final concentration: 1 μg/ml) for 30 min at 37° C. This was followed by incubation with n-formyl-Met-Leu-Phe (f-MLP) at 1 μM (Sigma Chem, F-3506, diluted in 1% w/v BSA/PBS) for 15 min at 37° C. The blood was immediately centrifuged at 4° C. for 10 min. at 3,300 rpms to obtain plasma. A plasma aliquot was diluted in PBS and assayed for TNF-α using a commercial ELISA kit (Cistron). An additional plasma aliquot was de-proteinized with methanol and the supernatant was assayed for LTB$_4$ using a commercial EIA kit (Cayman).

The instant compounds showed IC$_{50}$ values ranging from 1 nM to 5 μM.

Human Mononuclear Cell Assay

Fresh blood was collected from healthy volunteers by venipuncture into tubes containing 0.13M sodium citrate as anticoagulant (final 10% v/v in blood). The blood was diluted in equal parts with PBS and gently layered on top of one half volume histopaque (1.077 density) and was centrifuged at 1400 rpm for 35 min at room temperature. After centrifugation, a distinct layer of mononuclear cells (monocytes and lymphocytes) located between the blood and histopaque layers could be aspirated off using a transfer pipette. The mononuclear cells were washed in calcium and magnesium free PBS. The cell pellet was resuspended in RPMI 1640 (Gibco BRL) complete media (containing streptomycin/penicillin and HEPES buffer) at a cell density of 1×10$^6$ cells/ml. Two hundred μl aliquots of mononuclear cells were mixed with 2 μl of DMSO (vehicle) or a test compound at a final concentration of up to 10 μM in the presence of 1% or 25% heat-inactivated human serum. Fifteen min. later, the cells were incubated with LPS at a final concentration of 1 μg/ml at 37° C. for 20 h. At the end of the incubation period, the supernatant was obtained by centrifugation at 1000 rpm for 10 min and was assayed for TNF-α using a commercial ELISA kit (Cistron).

The instant compounds showed IC$_{50}$ values ranging from 0.1 nM to 5 μM.

In Vivo Inhibition of Allergen Induced Bronchoconstriction

Guinea pigs, 200 g, are sensitized with a 100 μg/ml ovalbumin in an Al$_2$O$_3$ suspension in physiological saline. Five hundred μl of this solution are injected intraperitoneally and another 500 μl are injected in 6 ganglionic regions (±75 μl/site). The animals are then housed for 4 to 6 weeks. Thirty minutes prior to the experimentation, the guinea pigs are treated with the test compound or vehicle and with mepyramine maleate, 1 mg/kg. The injection volume is 1 ml/kg of body weight.

After pre-treatment, the animals are placed in a whole body plethysmograph for conscious unrestrained guinea pigs. The animals are challenged for one minute with an aerosol containing ovalbumin in a concentration of 1% in physiological saline. The changes in pulmonary function assessed as changes in enhanced pause or Penh. Penh, a marker of bronchoconstriction, is defined as follows:

Penh=[(expiratory time/relaxation time)−1]*[(peak expiratory flow/peak inspiratory flow]

The results are expressed as the percentage of inhibition of the Penh increase versus the response obtained in a control experiment.

SPA Based PDE Activity Assay Protocol for Measuring Inhibition of Phosphodiesterase Activity Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 μl DMSO), 188 μl of substrate buffer containing [2,8-$^3$H] adenosine 3',5'-cyclic phosphate (cAMP, 100 nM), 10 mM MgCl$_2$, mM EDTA, 50 mM Tris, pH 7.5. The reaction was initiated by the addition of 10 μl of human recombinant PDE-IV isozymes, either expressed and purified from sf9 cells, or from CHO-K1 cells (the amount was controlled so that ~10% product was formed in 10 min. at 30° C). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. The IC$_{50}$ value was approximated by the non-linear regression fitting of a ten point titration using the standard 4 parameter equation.

IC$_{50}$ values were determined with 100 nM cAMP using the purified GST fusion protein of the human recombinant phosphodiesterase IVa (met-248) produced from a baculovirus/Sf-9 expression system. The instant compounds were shown to have IC$_{50}$ values of 0.01 to 1000 nM.

What is claimed is:

1. A compound of Formula I

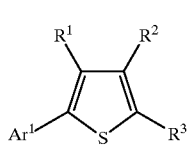

(I)

or a pharmaceutically acceptable salt thereof wherein:
Ar$^1$ is an aromatic ring selected from phenyl, quinolinyl, pyridinyl, furyl, thienyl or thiazolyl, optionally substituted with up to two substituents chosen independently from among:
a) C$_{1-6}$alkyl, optionally substituted with —OH, —CO$_2$H, CO$_2$C$_{1-3}$alkyl, and CN, b) $C_{1-3}$alkoxy,
c) $C_{1-3}$alkylthio,
d) $C_{1-3}$alkylsulfinyl,
e) $C_{1-3}$alkylsulfonyl,
f) $C_{1-3}$fluoroalkyl, optionally substituted with —OH,
g) halo,
h) —OH,
i) —CO$_2$H,
j) —CO$_2$C$_{1-3}$alkyl,
k) —CH=CH—C(Me)$_2$OH,
l) —CONR$^4$R$^5$,
m) —S(O)$_2$NR$^6$R$^7$,
n) tetrazol-5-yl, or
o) —CH=N—O—CH$_2$CO$_2$H;

R$^1$ is
—X$^1$—Y$^1$—Ar$^2$,
wherein:
X$^1$ is
—CH$_2$—;
Y$^1$ is
—S—;
Ar$^2$ is an aromatic ring selected from phenyl, naphthyl, pyrimidinyl, pyridinyl or thienyl, optionally substituted with up to two substituents chosen independently from among:
1) $C_{1-6}$alkyl,
2) $C_{1-6}$alkoxy,
3) —OH,
4) halo, or
5) CF$_3$;

R$^2$ is selected from:
a) hydrogen or
b) $C_{1-3}$alkyl;

R$^3$ is selected from phenyl, naphthyl, pyridinyl, furyl, thienyl, or ethinyl, optionally substituted with up to two substituents chosen independently from among:
a) $C_{1-3}$alkyl,
b) $C_{1-3}$fluoroalkyl,
c) $C_{1-6}$alkoxy,
d) $C_{1-3}$fluoroalkoxy,
e) $C_{1-3}$alkylthio,
f) halo,
g) —OH,
h) —NO$_2$,
i) —CH$_2$OH,
j) —NHCONR$^9$R$^{10}$,
k) —S(O)$_2$NR$^{11}$R$^{12}$,
l) —SCH$_2$(1,1-c-Pr)CH$_2$CO$_2$H,
m) 1-piperazinyl, optionally substituted with $C_{1-3}$alkyl,
n) 4-morpholinyl, or
o) —X$^2$13 Y$^2$—Ar$^3$,
wherein,
X$^2$ is
1) —CH$_2$—,
2) —C(=NOH)—, or
3) a bond;
Y$^2$ is
1) —O—,
2) —S—, or
3) a bond;
Ar$^3$ is phenyl, pyridinyl, pyrimidinyl or pyrazinyl, optionally substituted with up to two substituents chosen independently from among:
1) $C_{1-3}$alkyl, optionally substituted with —OH, or
2) —CH$_2$CO$_2$H;

R$^4$ and R$^5$ are independently selected from:
a) hydrogen,
b) $C_{1-3}$alkyl,
c) —S(O)$_2$C$_{1-3}$alkyl, or
d) —S(O)$_2$phenyl, optionally mono-substituted with $C_{1-3}$alkyl, $C_{1-3}$alkoxy, $C_{1-3}$alkylthio or halo;

R$^6$ and R$^7$ are independently chosen from among:
a) hydrogen,
b) $C_{1-4}$alkyl,
c) —CO—$C_{1-4}$alkyl, or
d) —CO-phenyl, optionally mono-substituted with $C_{1-3}$alkyl, $C_{1-3}$alkoxy, $C_{1-3}$alkylthio, or halo;

R$^8$ is chosen from among:
a) hydrogen, or
b) $C_{1-5}$alkyl;

R$^9$ and R$^{10}$ are independently chosen from among:
a) hydrogen,
b) $C_{1-4}$alkyl, or
c) phenyl; and R$^{11}$ and R$^{12}$ are independently chosen from among:
a) hydrogen, or
b) $C_{1-5}$alkyl.

2. A compound according to claim 1 wherein:
R2 is hydrogen, and the remaining substituents are defined as in claim 1.

3. A compound according to claim 1 wherein:
—X$^1$—Y$^1$— is —CH$_2$-S—,
and the remaining substituents are defined as in claim 1.

4. A compound according to claim 1 wherein:
Ar$^2$ is pyrimidinyl, optionally substituted with up to two substituents chosen independently among:
1) $C_{1-6}$alkyl,
2) $C_{1-6}$alkoxy,
3) —OH, or
4) halo,
and the remaining substituents are defined as in claim 1.

5. A compound according to claim 1 wherein
Ar$^1$ is an aromatic ring selected from phenyl, quinolinyl, pyridinyl, furyl, thienyl or thiazolyl, optionally substituted with up to two substituents chosen independently from among:
a) $C_{1-6}$alkyl, optionally substituted with —OH, —CO$_2$H, CO$_2$C$_{1-3}$alkyl, and CN,
b) $C_{1-3}$alkoxy,
c) $C_{1-3}$alkylthio,
d) $C_{1-3}$alkylsulfinyl,
e) $C_{1-3}$alkylsulfonyl,
f) $C_{1-3}$fluoroalkyl, optionally substituted with —OH,
g) halo,
h) —OH,
i) —CO$_2$H, or
j) —CO$_2$C$_{1-3}$alkyl,
Ar$^2$ is pyrimidinyl optionally substituted with up to two substituents chosen independently from among:
1) $C_{1-6}$alkyl,
2) $C_{1-6}$alkoxy,
3) —OH, or
4) halo, R$^2$ is hydrogen R$^3$ is selected from phenyl, naphthyl, pyridinyl, furyl, or thienyl, optionally substituted with up to two substituents chosen independently from among:
a) $C_{1-3}$alkyl,
b) $C_{1-3}$fluoroalkyl, c) $C_{1-6}$alkoxy,
d) $C_{1-3}$fluoroalkoxy,
e) $C_{1-3}$alkylthio,
f) halo,
g) —OH,
h) —$NO_2$,
i) —$CH_2OH$,
j) —$NHCONR^9R^{10}$,
k) —$S(O)_2NR^{11}R^{12}$,
l) —$SCH_2(1,1\text{-c-Pr})CH_2CO_2H$ or
m) —$X^2$—$Y^2$—$Ar^3$,
   wherein,
   $X^2$ is
      1) —$CH_2$—,
      2) —$C(=NOH)$—, or
      3) a bond;
   $Y^2$ is
      1) —O—,
      2) —S—, or
      3) a bond;
   $Ar^3$ is phenyl, pyridinyl, or pyrimidinyl optionally substituted with up to two substituents chosen independently from among:
      1) $C_{1-3}$alkyl, optionally substituted with —OH, or
      2) —$CH_2CO_2H$;
$R^4$ and $R^5$ are independently selected from:
   a) hydrogen,
   b) $C_{1-3}$alkyl, or
   c) —$S(O)_2C_{1-3}$alkyl;
$R^6$ and $R^7$ are independently chosen from among:
   a) hydrogen,
   b) $C_{1-4}$alkyl, or
   c) —CO—$C_{1-4}$alkyl;
$R^8$ is chosen from among:
   a) hydrogen, or
   b) $C_{1-5}$alkyl;
$R^9$ and $R^{10}$ are independently chosen from among:
   a) hydrogen, or
   b) $C_{1-4}$alkyl, and
$R^{11}$ and $R^{12}$ are independently chosen from among:
   a) hydrogen, or
   b) $C_{1-5}$alkyl.

6. A compound according to claim 1 wherein
$Ar^1$ is an aromatic ring selected from phenyl, quinolinyl, pyridinyl, furyl, thienyl or thiazolyl, optionally substituted with up to two substituents chosen independently from among:
   a) $C_{1-6}$alkyl, optionally substituted with —OH, —$CO_2H$, $CO_2C_{1-3}$alkyl, and CN,
   b) $C_{1-3}$alkoxy,
   c) $C_{1-3}$alkylthio,
   d) $C_{1-3}$alkylsulfinyl,
   e) $C_{1-3}$alkylsulfonyl,
   f) $C_{1-3}$fluoroalkyl, optionally substituted with —OH,
   g) halo,
   h) —OH,
   i) —$CO_2H$, or
   j) —$CO_2C_{1-3}$alkyl,
   $Ar^2$ is pyrimidinyl optionally substituted with up to two substituents chosen independently from among:
      1) $C_{1-6}$alkyl,
      2) $C_{1-6}$alkoxy,
      3) —OH, or
      4) halo;
$R^2$ is hydrogen;
$R^3$ is selected from phenyl, pyridinyl, furyl, or thienyl, optionally substituted with up to two substituents chosen independently from among:
   a) $C_{1-3}$alkyl,
   b) $C_{1-3}$fluoroalkyl,
   c) $C_{1-6}$alkoxy,
   d) $C_{1-3}$fluoroalkoxy,
   e) $C_{1-3}$alkylthio,
   f) halo,
   g) OH,
   h) —$NO_2$,
   i) —$CH_2OH$,
   j) —$NHCONR^9R^{10}$, or
   k) —$X^2$—$Y^2$—$Ar^3$,
      wherein,
      $X^2$ is
         1) —$CH_2$—, or
         2) a bond;
      $Y^2$ is
         1) —O—,
         2) —S—, or
         3) a bond;
      $Ar^3$ is phenyl, pyridinyl, or pyrimidinyl optionally substituted with up to two substituents chosen independently from among:
         1) $C_{1-3}$alkyl, optionally substituted with —OH, or
         2) —$CH_2CO_2H$;
$R^4$ and $R^5$ are independently selected from:
   a) hydrogen,
   b) $C_{1-3}$alkyl;
$R^6$ and $R^7$ are independently chosen from among:
   a) hydrogen, or
   b) $C_{1-4}$alkyl;
$R^8$, $R^{11}$ and $R^{12}$ are chosen from among:
   a) hydrogen, or
   b) $C_{1-5}$alkyl; and
$R^9$ and $R^{10}$ are independently chosen from among:
   a) hydrogen, or
   b) $C_{1-4}$alkyl.

7. A compound according to claim 1 selected from the group consisting of
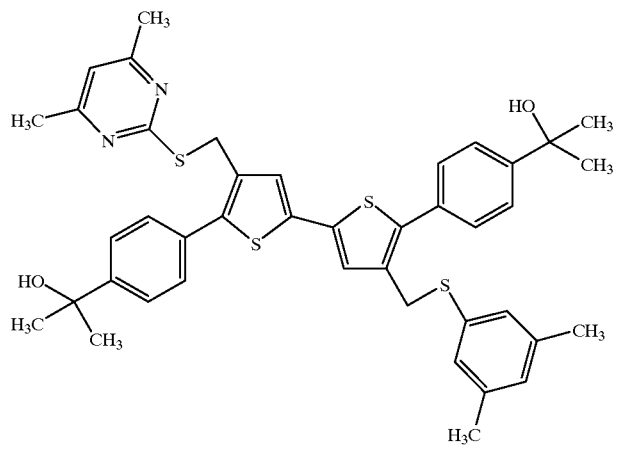
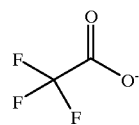
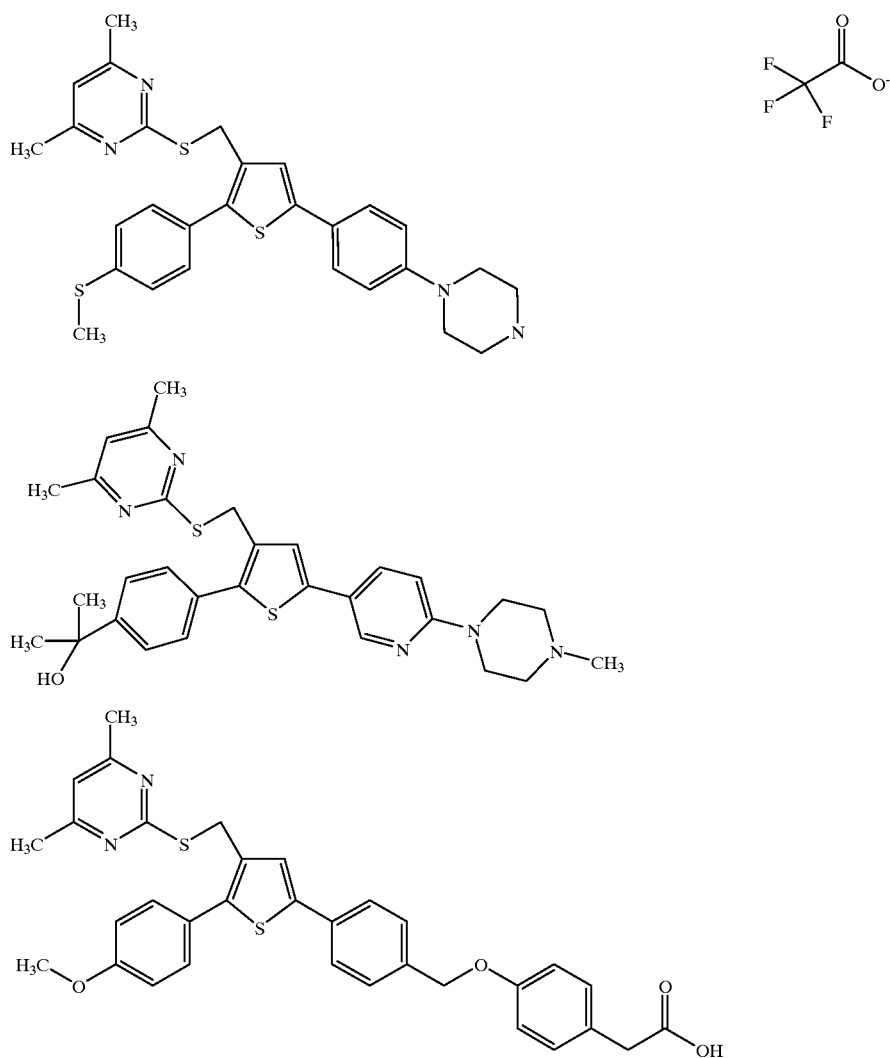

| 79 | 80 |
|---|---|
| 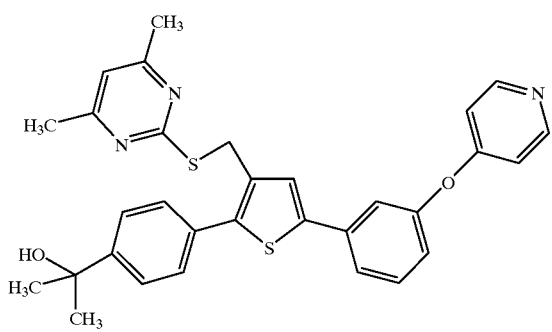 | 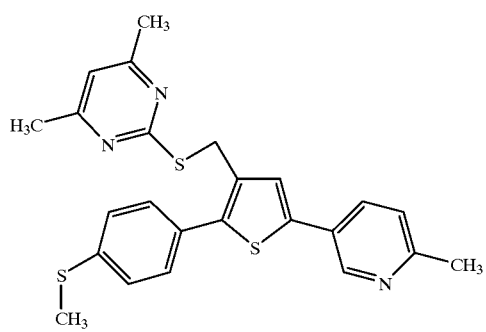 |
| 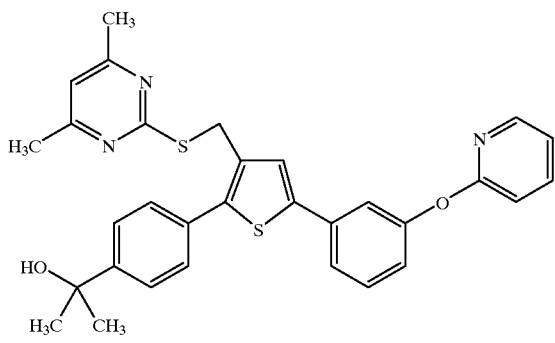 | 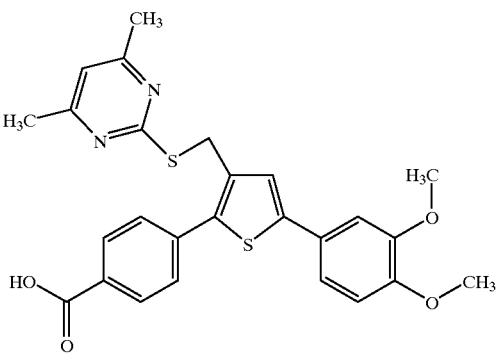 |
| 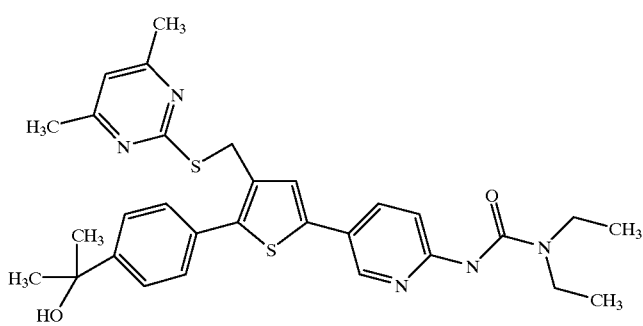 | |
| 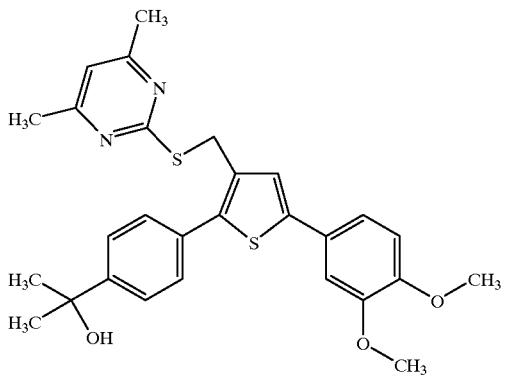 | 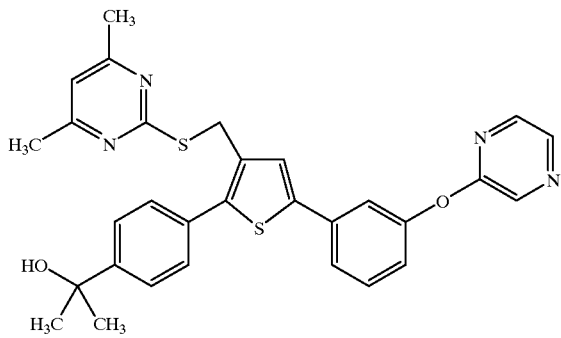 |

81
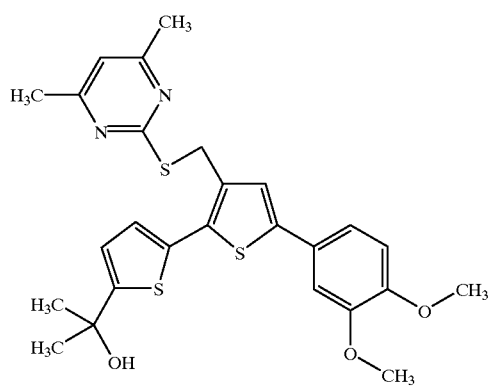
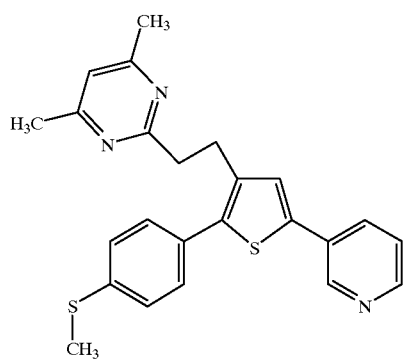
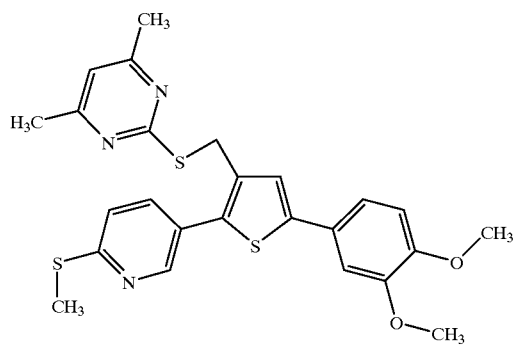
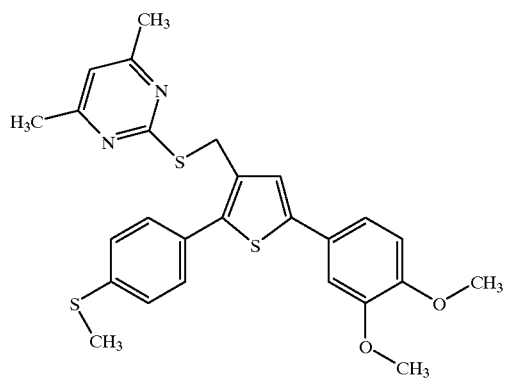
82
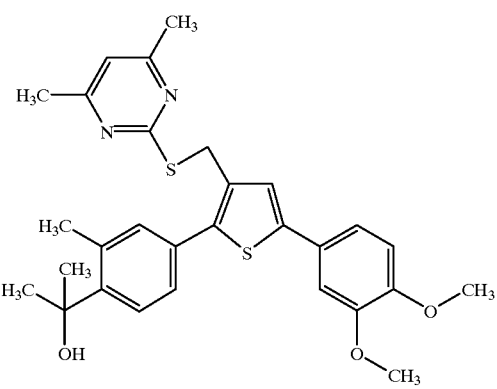
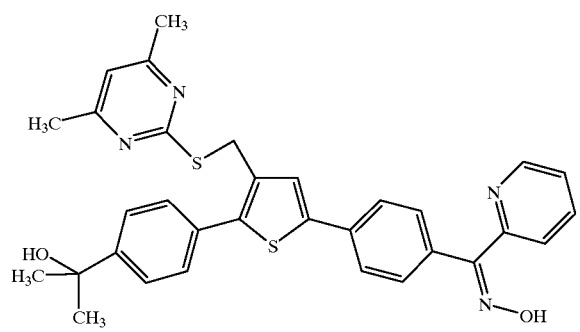
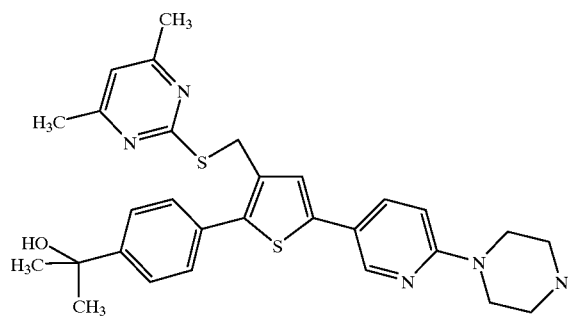
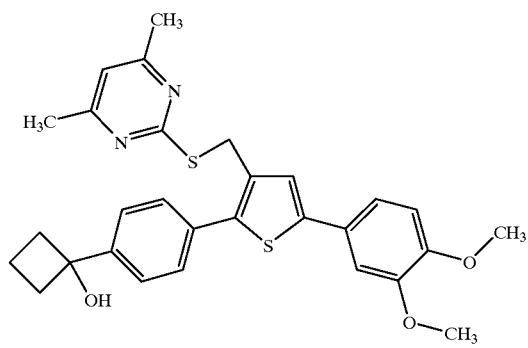

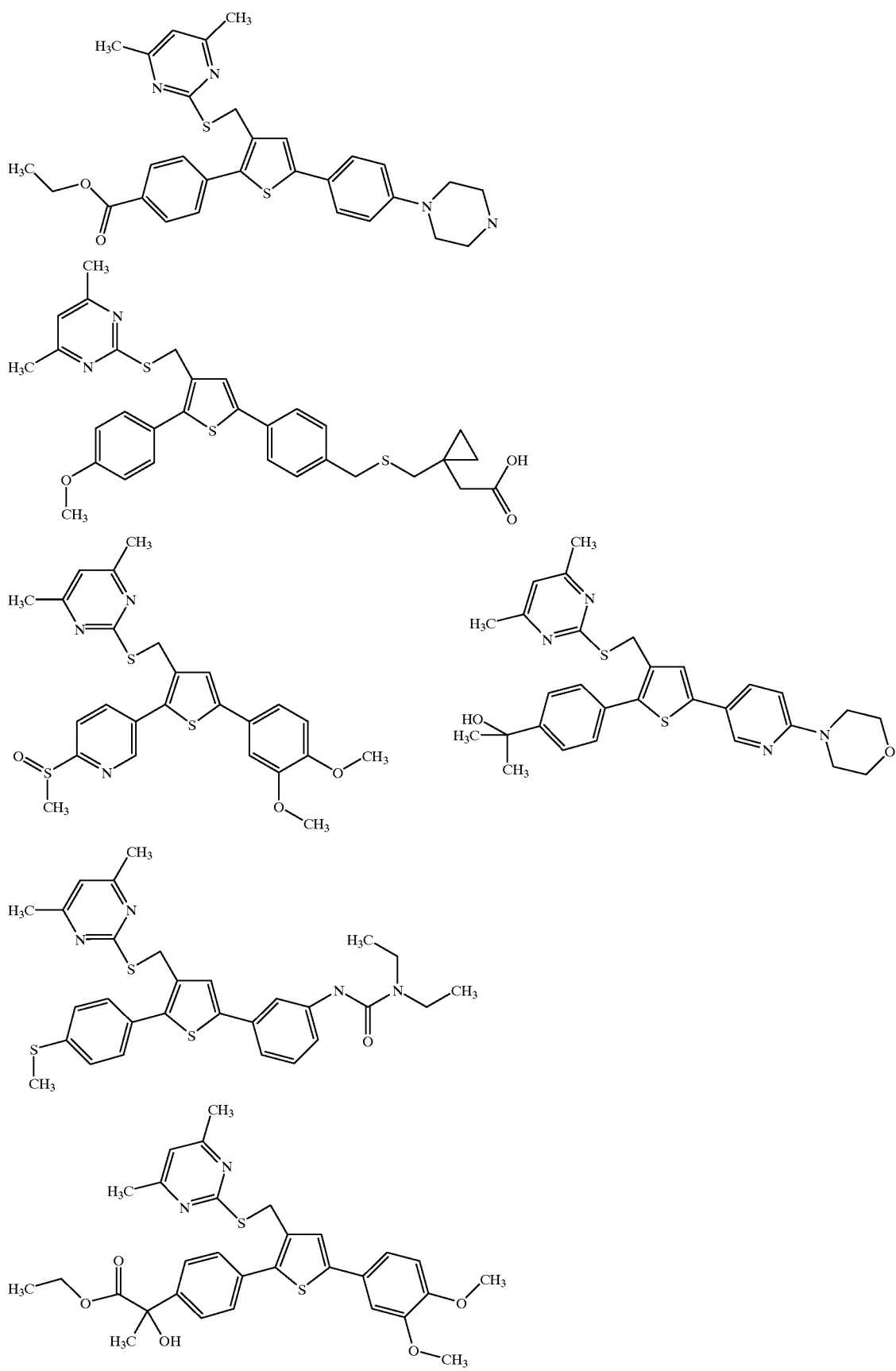

85
-continued
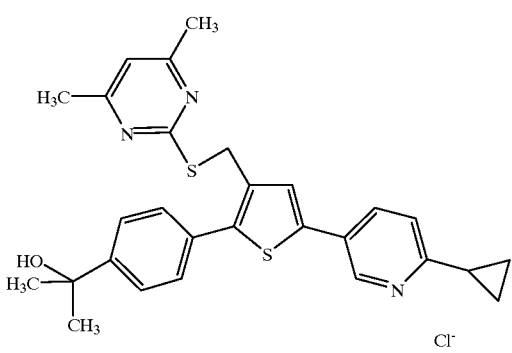
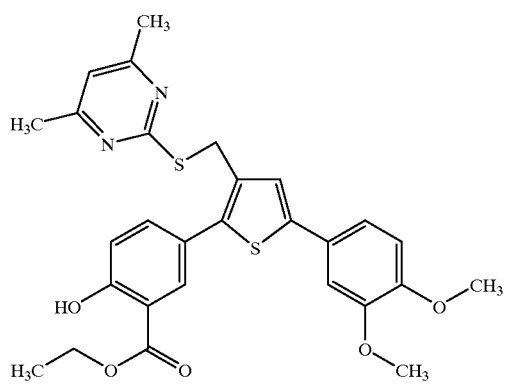
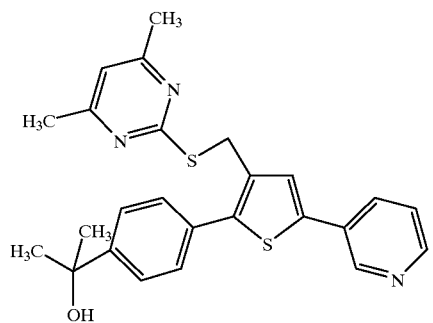
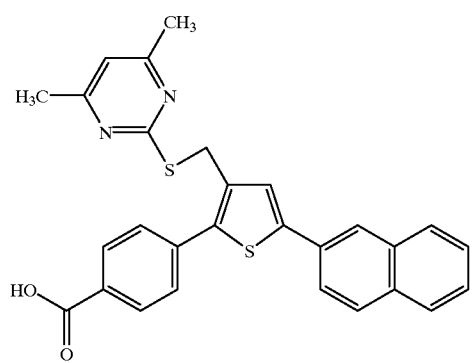
86
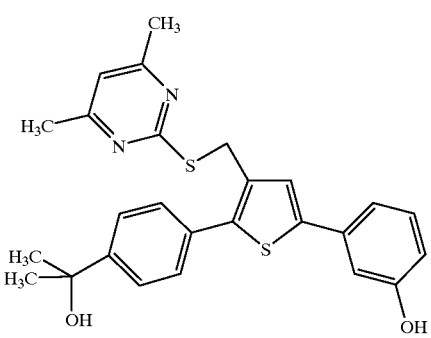
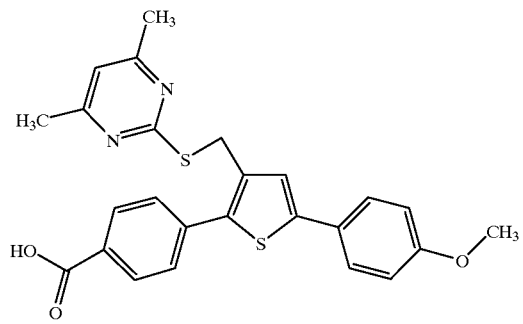
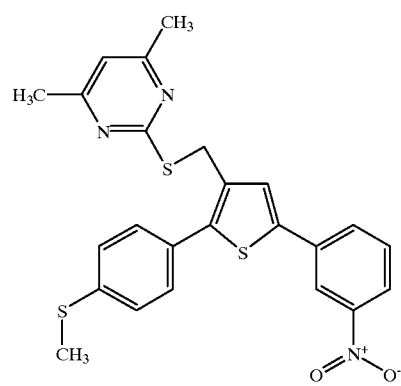
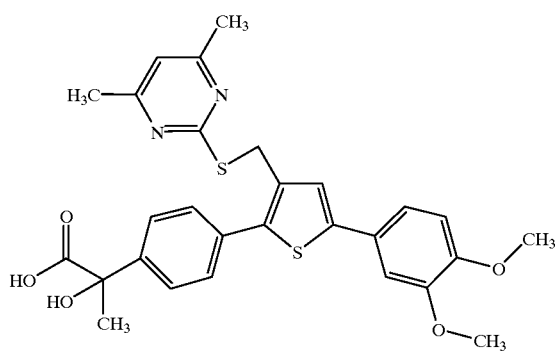

87
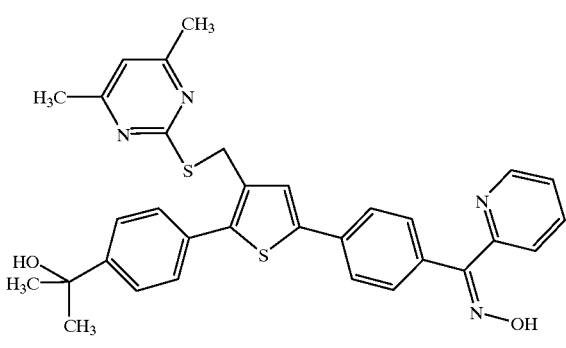
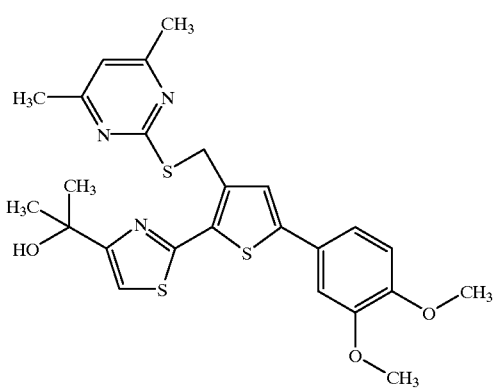
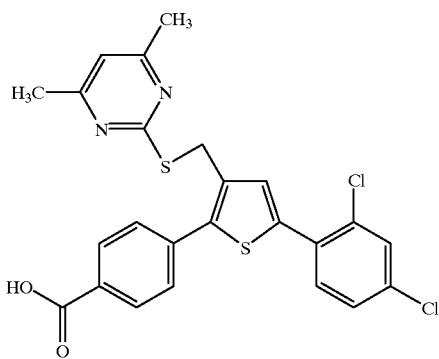
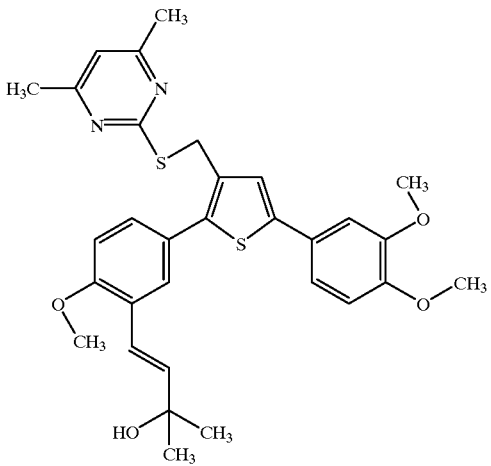
88
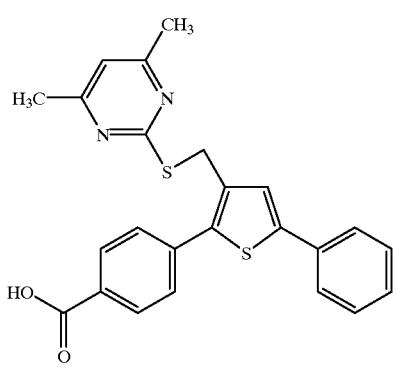
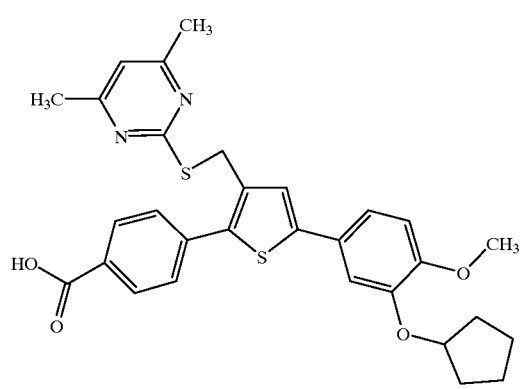
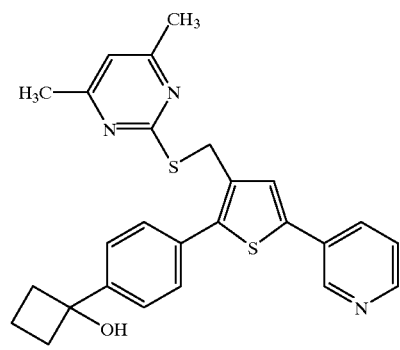
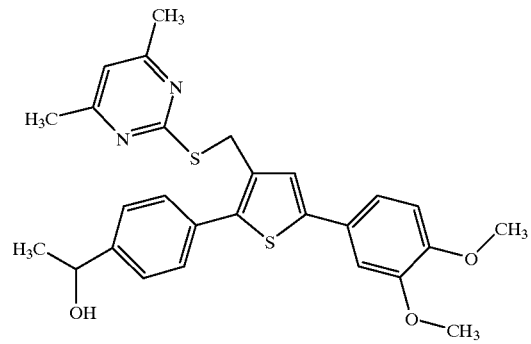

89 90
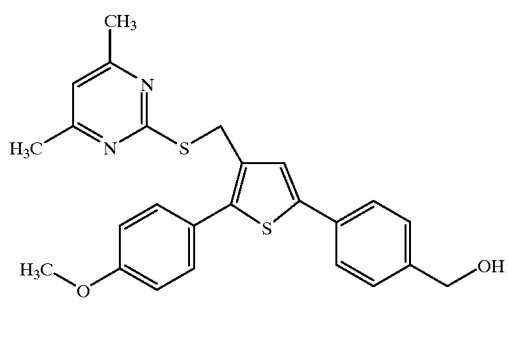 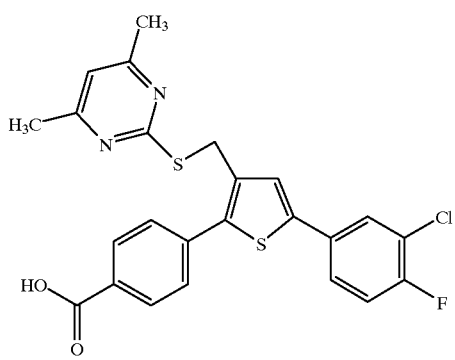
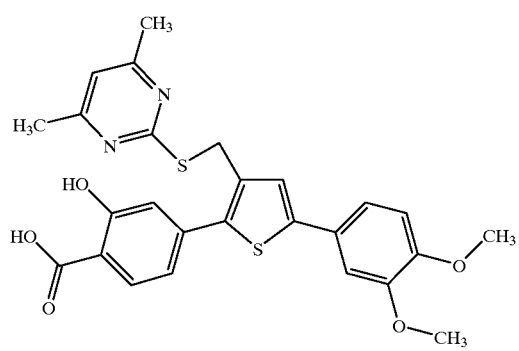 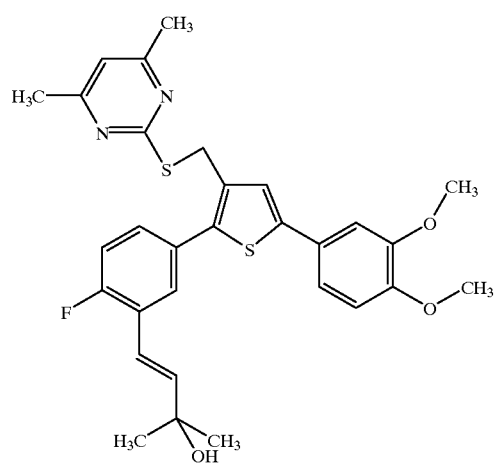
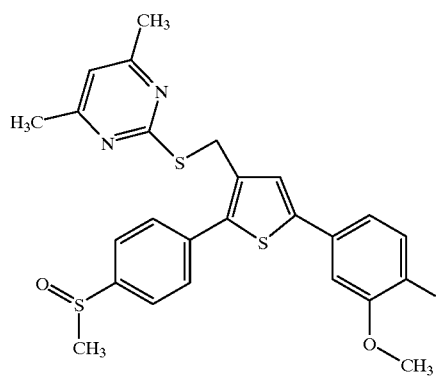 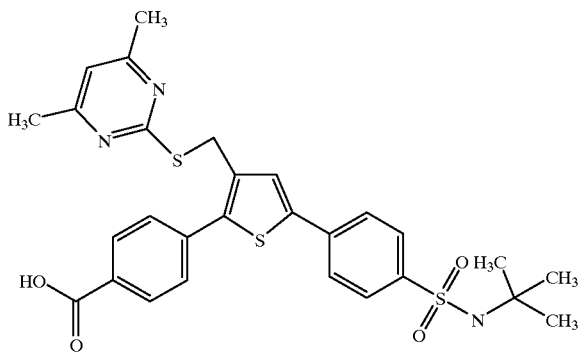
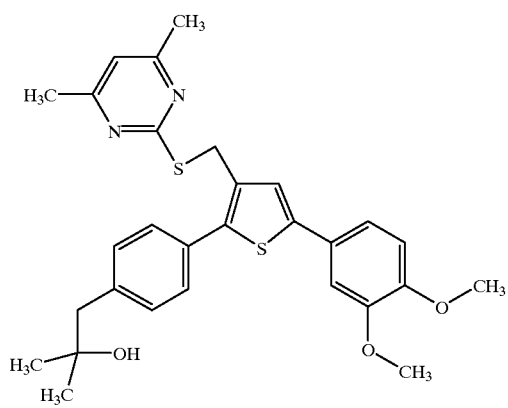 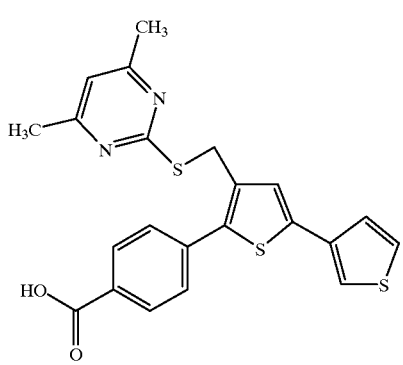

91 92
-continued
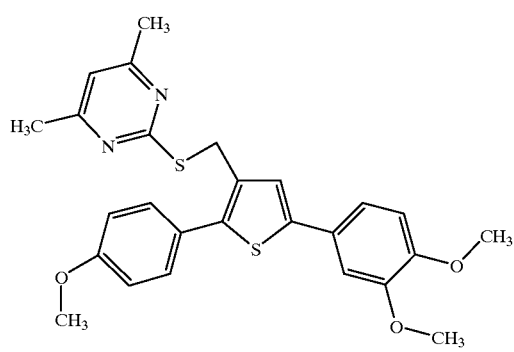
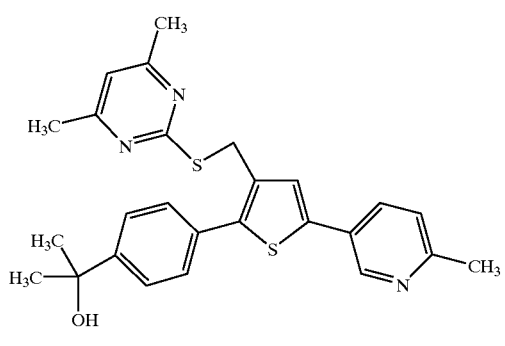
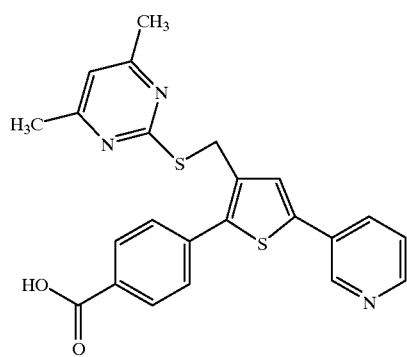
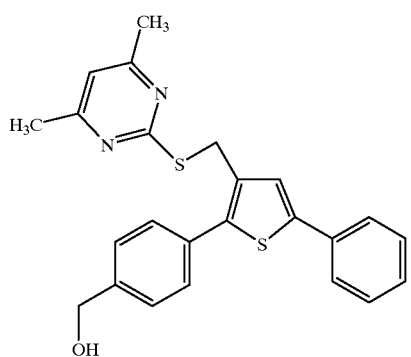
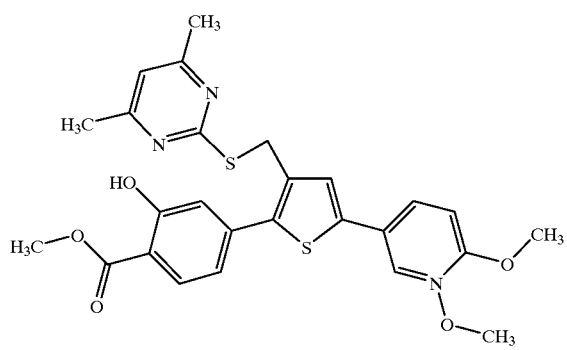
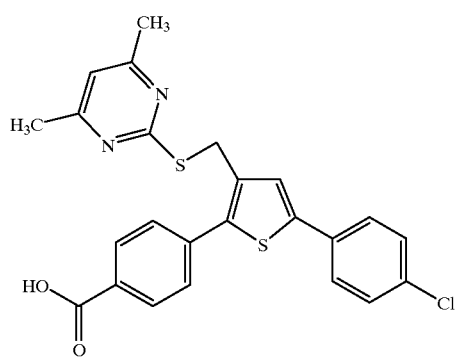
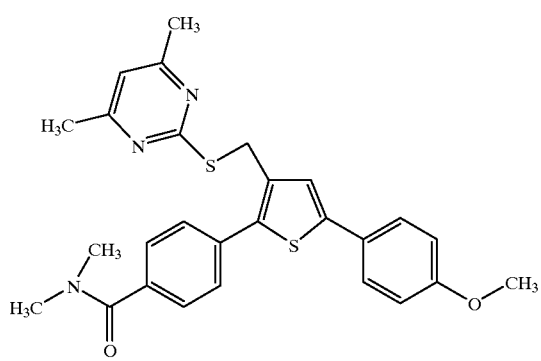
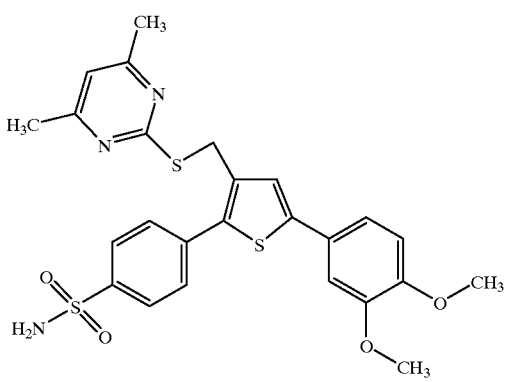

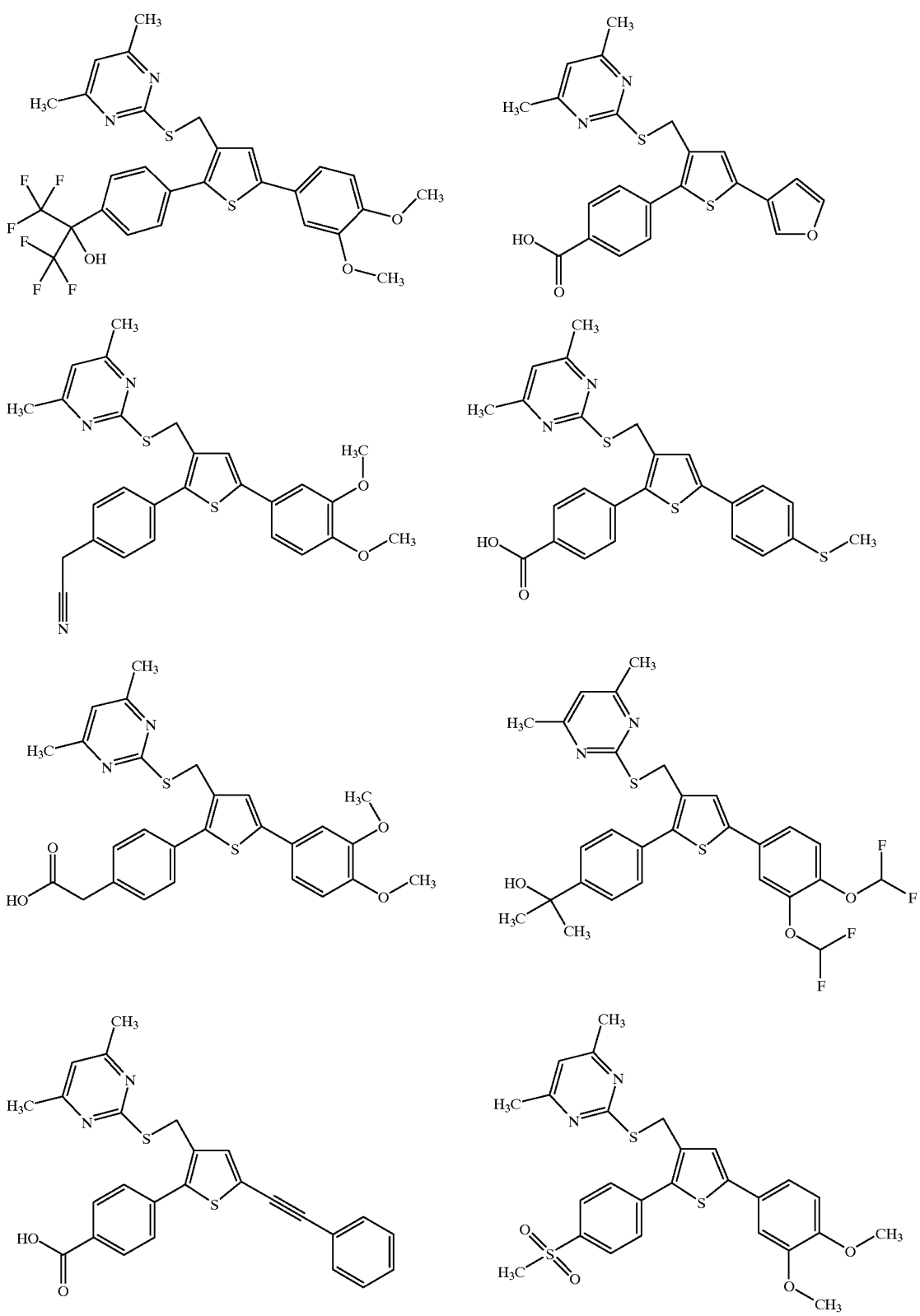

95 96
-continued
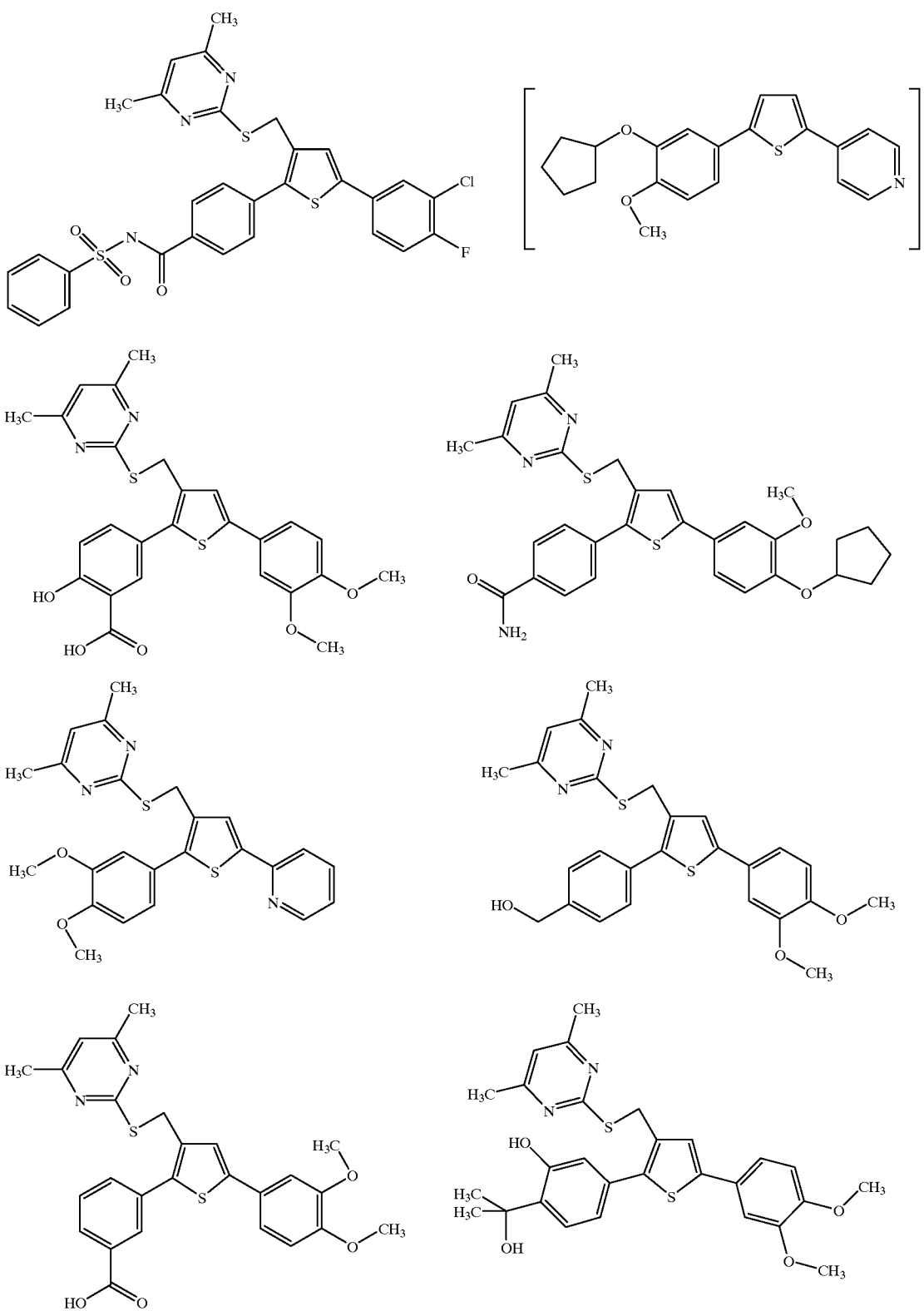

97
98
-continued
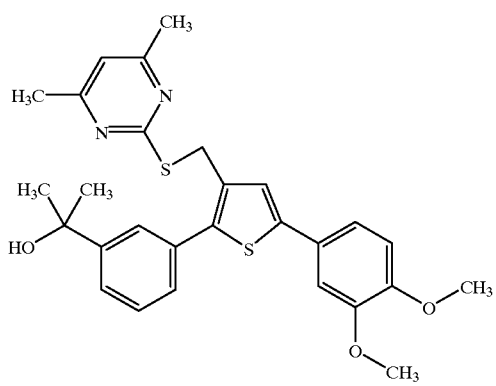
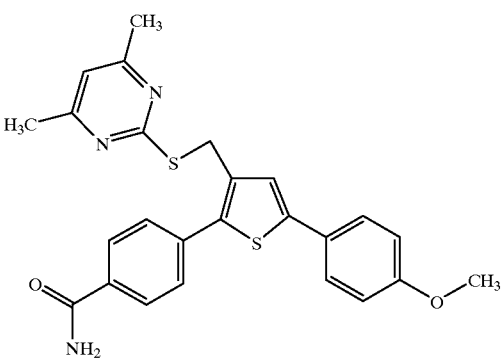
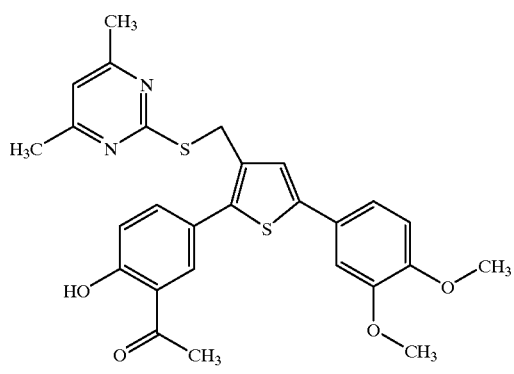
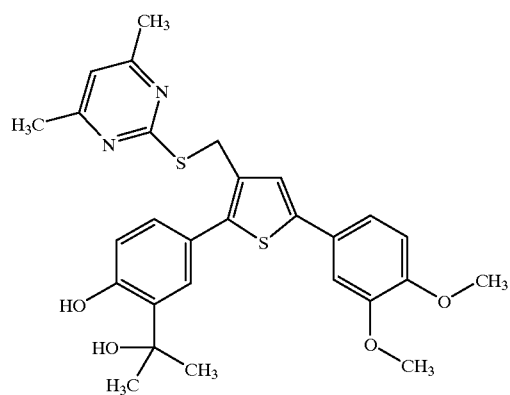
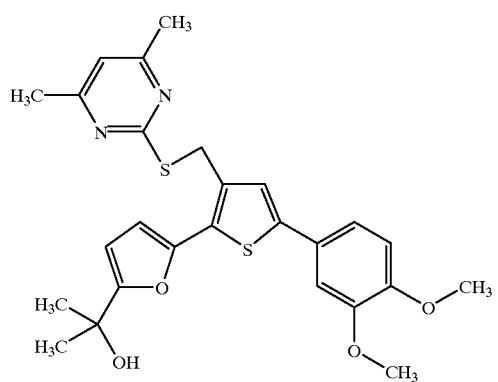
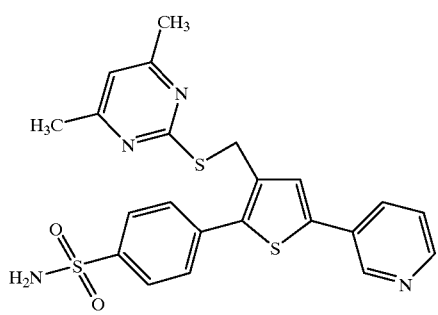
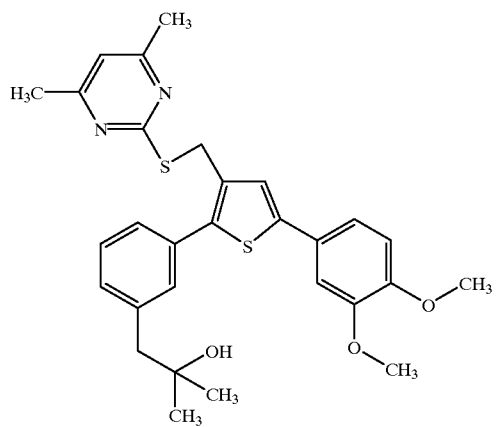
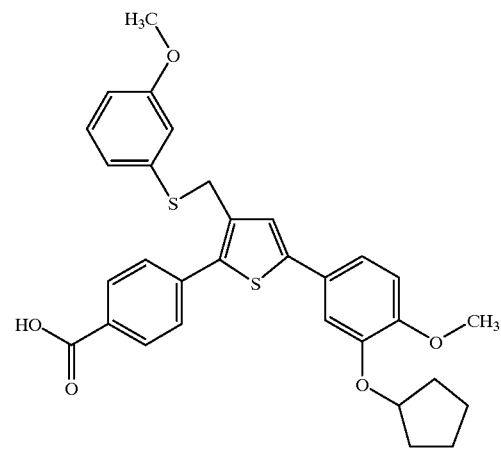

99 100
-continued
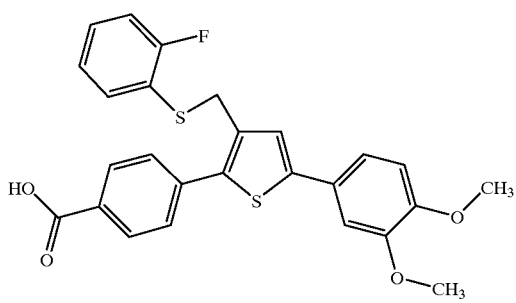 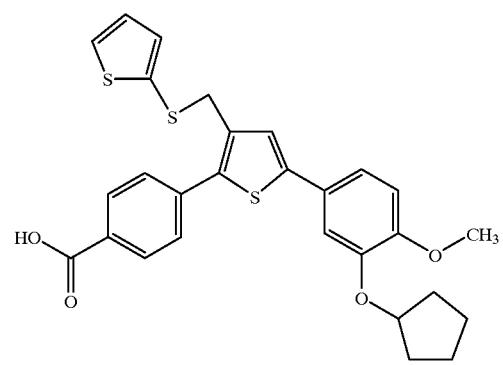
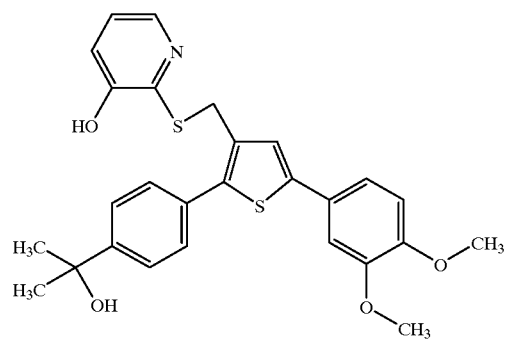 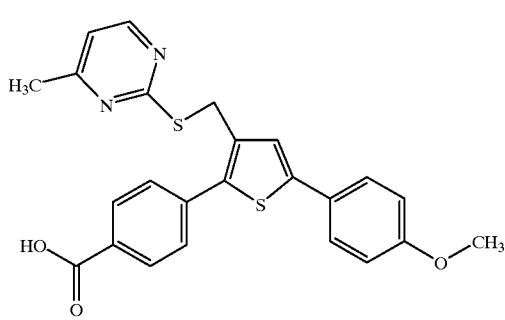
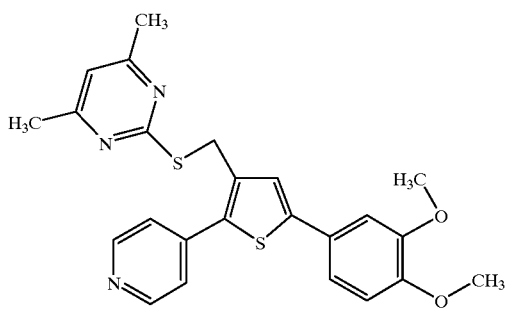 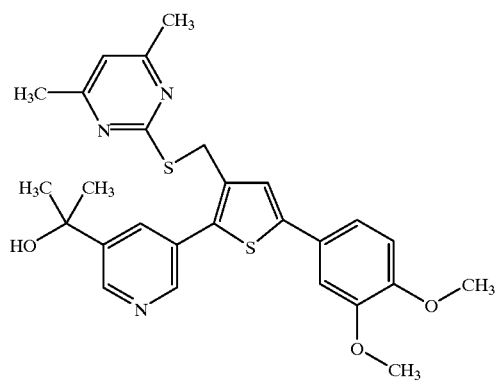
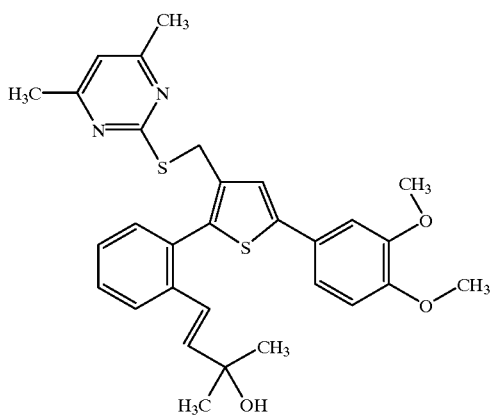 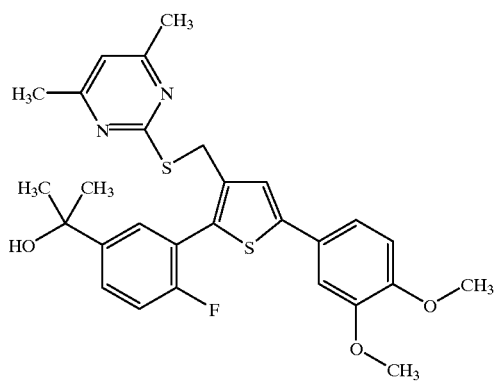

101 102
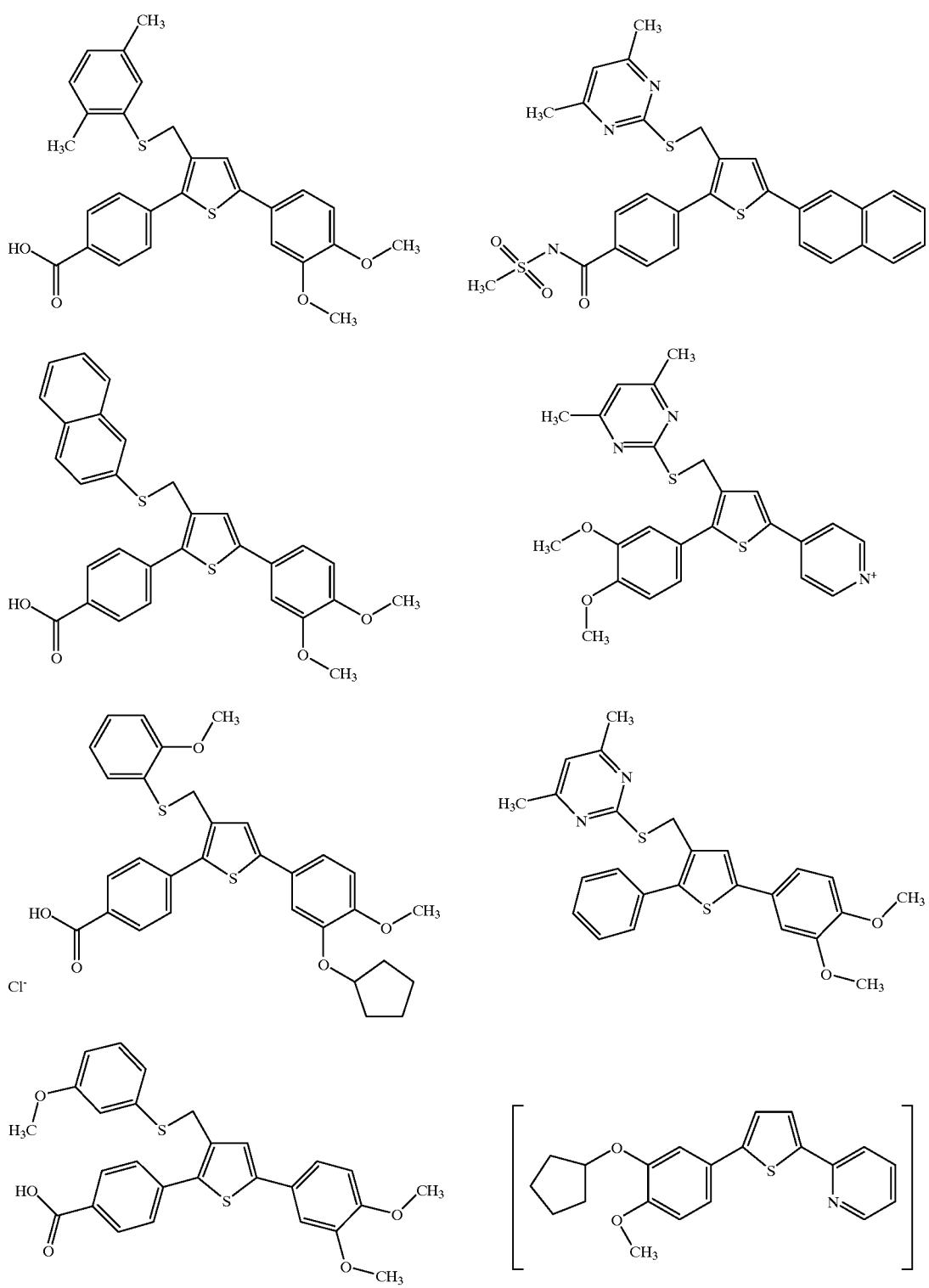

-continued
103
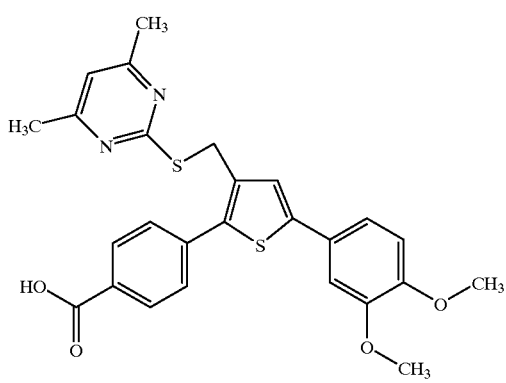
104
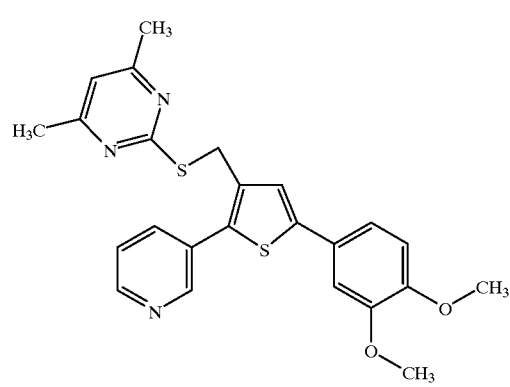
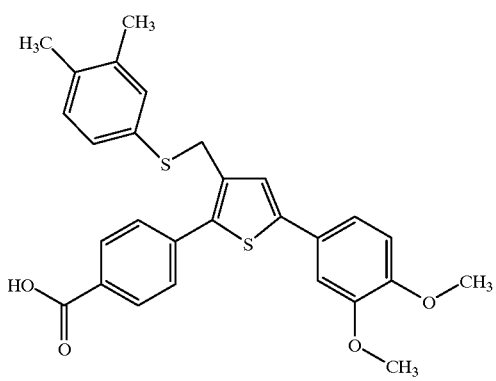
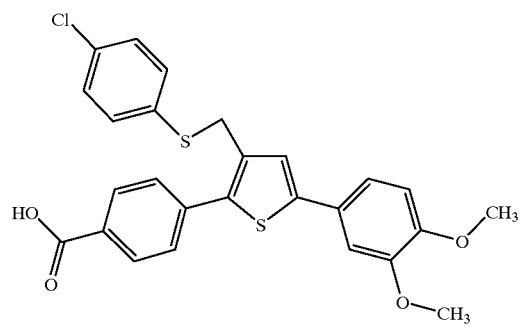
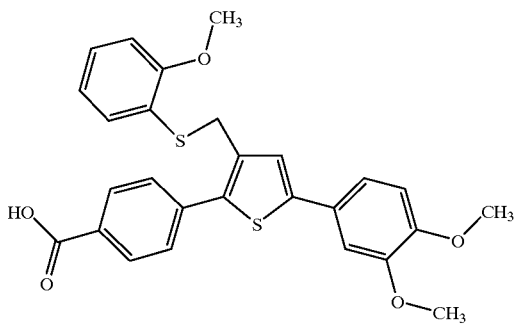
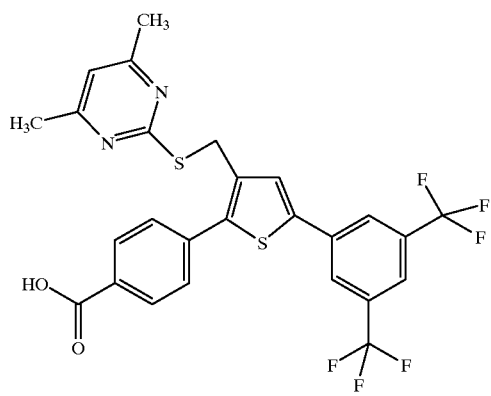
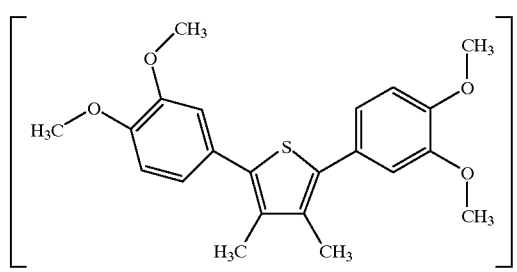
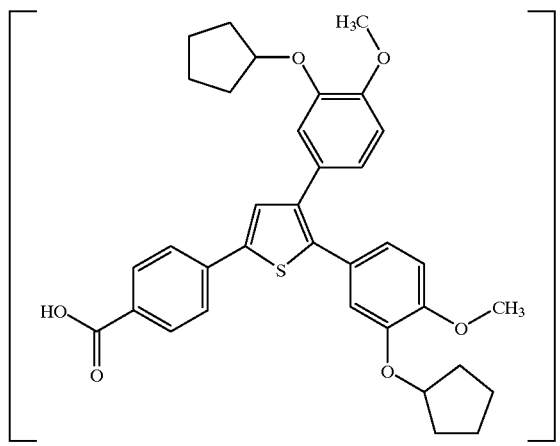

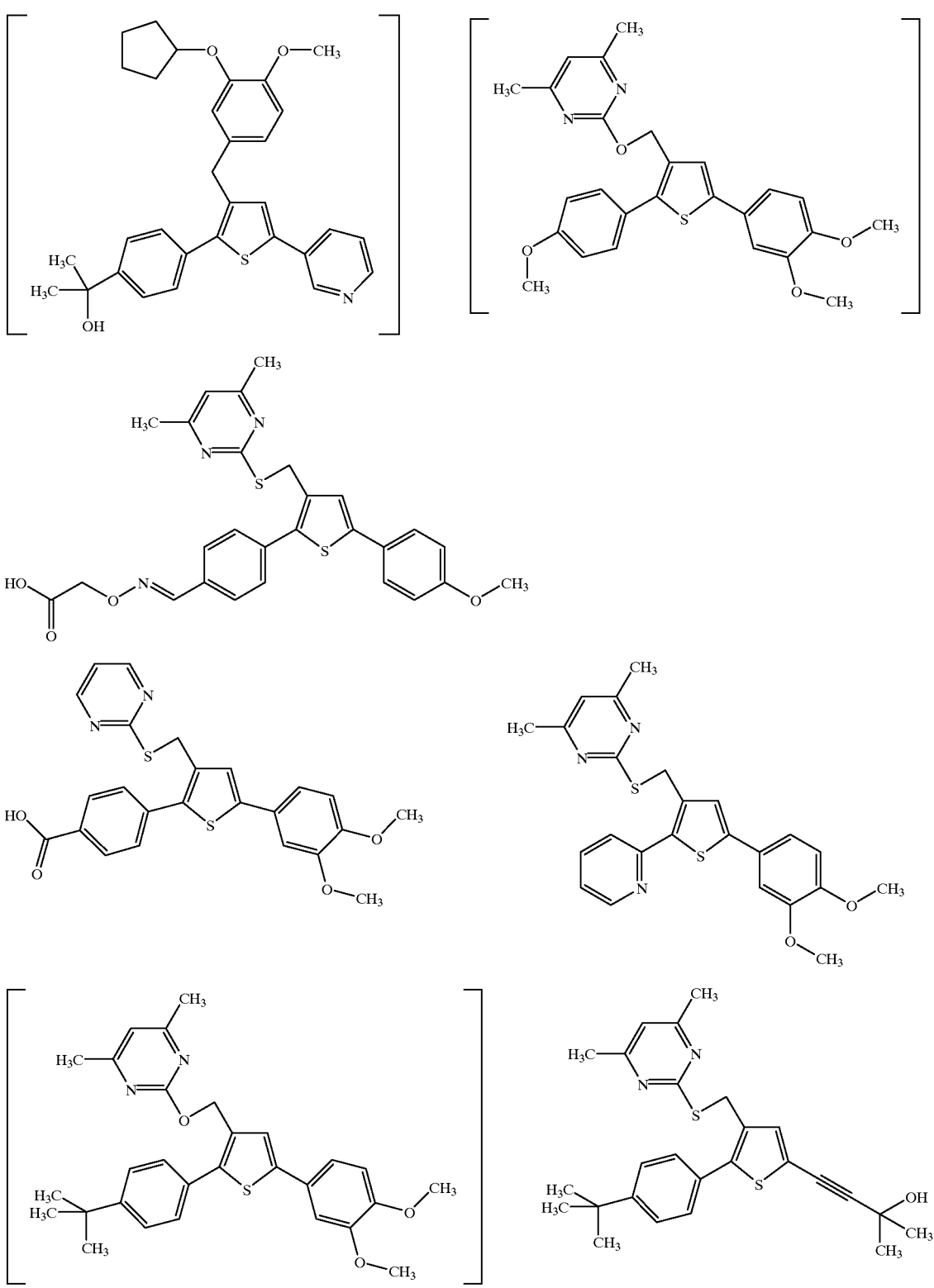

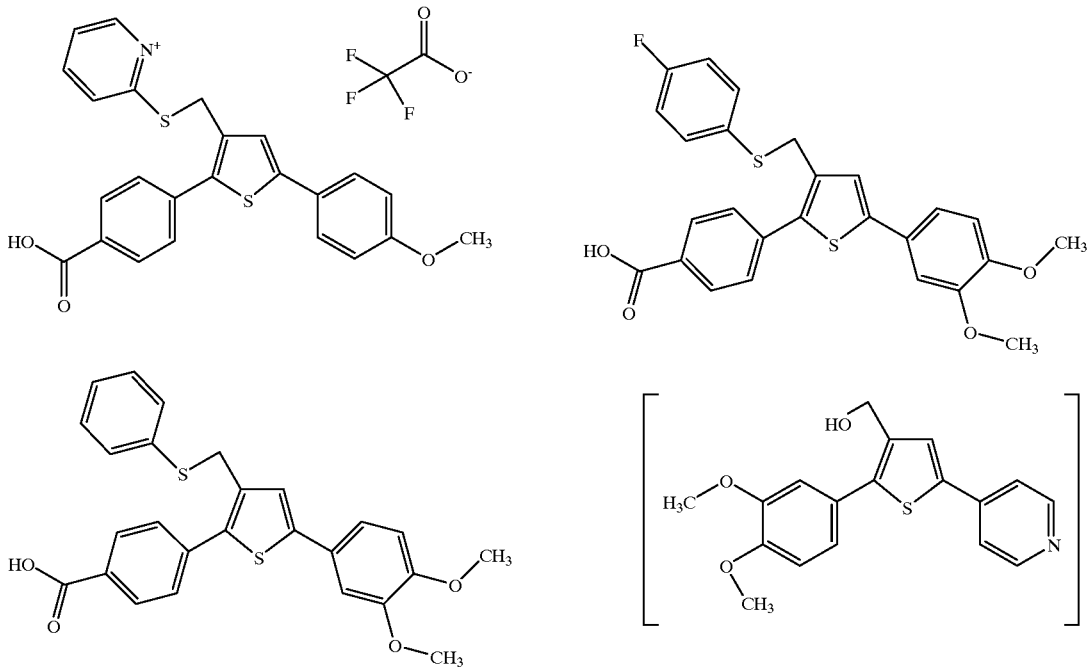

8. A pharmaceutical composition for treating asthma comprising a non-toxic therapeutically effective amount of a compound according to claim 1 and a pharmaceutically acceptable carrier.

9. A pharmaceutical composition for treating a phosphodiesterase IV mediated disease by increasing the cellular level of cAMP, comprising a non-toxic therapeutically effective amount of a compound according to claim 1 and a pharmaceutically acceptable carrier.

10. A method of treating asthma comprising administration to a patient in need of such treatment of a non-toxic therapeutically effective amount of a compound according to claim 1 and a pharmaceutically acceptable carrier.

11. A method of treating a phosphodiesterase IV mediated disease by inhibiting PDE IV comprising administration to a patient in need of such treatment of a non-toxic therapeutically effective amount of a compound according to claim 1.

* * * * *

UNITED STATES PATENT AND TRADEMARK OFFICE
CERTIFICATE OF CORRECTION

PATENT NO. : 6,034,089
DATED : 3/7/2000
INVENTOR(S) : Yongxin Han, Andre Giroux, Dwight MacDonald, Robert N. Yound Helene Perrier, and Carole Lepine It is certified that error appears in the above-identified patent and that said Letters Patent is hereby corrected as shown below:

ON THE TITLE PAGE:

Item [73] Assignee should read -- Merck Frosst Canada, Inc. --

Signed and Sealed this

Eleventh Day of July, 2000

Attest:

Q. TODD DICKINSON

*Attesting Officer*                *Director of Patents and Trademarks*